United States Patent
Benting et al.

(10) Patent No.: US 9,375,004 B2
(45) Date of Patent: *Jun. 28, 2016

(54) 5-HALOGENOPYRAZOLECARBOXAMIDES

(75) Inventors: Jürgen Benting, Leichlingen (DE);
Pierre-Yves Coqueron, Lyons (FR);
Pierre Cristau, Lyons (FR); Peter Dahmen, Neuss (DE); Philippe Desbordes, Lyons (FR); Christophe Dubost, Charbonnieres les bains (FR); Stephanie Gary, Champagne au Mont d Or (FR); Jörg Greul, Leverkusen (DE); Hiroyuki Hadano, Tochigi (JP); Jean-Pierre Vors, Saint Foy les Lyon (FR); Ulrike Wachendorff-Neumann, Neuwied (DE)

(73) Assignee: Bayer Intellectual Property GmbH, Monheim (DE)

( * ) Notice: Subject to any disclaimer, the term of this patent is extended or adjusted under 35 U.S.C. 154(b) by 180 days.

This patent is subject to a terminal disclaimer.

(21) Appl. No.: 13/884,931

(22) PCT Filed: Nov. 14, 2011

(86) PCT No.: PCT/EP2011/070041
§ 371 (c)(1),
(2), (4) Date: Jul. 23, 2013

(87) PCT Pub. No.: WO2012/065947
PCT Pub. Date: May 24, 2012

(65) Prior Publication Data
US 2013/0296269 A1 Nov. 7, 2013

Related U.S. Application Data

(60) Provisional application No. 61/416,828, filed on Nov. 24, 2010.

(30) Foreign Application Priority Data

| Nov. 15, 2010 | (EP) | 10191269 |
| Nov. 15, 2010 | (EP) | 10191270 |
| Nov. 18, 2010 | (EP) | 10191740 |
| Nov. 18, 2010 | (EP) | 10191761 |
| Jun. 9, 2011 | (EP) | 11356008 |

(51) Int. Cl.
*A01N 43/56* (2006.01)
*A01N 55/00* (2006.01)
*C07D 231/14* (2006.01)
*C07D 405/12* (2006.01)

(52) U.S. Cl.
CPC ............... *A01N 43/56* (2013.01); *A01N 55/00* (2013.01); *C07D 231/14* (2013.01); *C07D 405/12* (2013.01)

(58) Field of Classification Search
None
See application file for complete search history.

(56) References Cited

U.S. PATENT DOCUMENTS

| 3,937,840 | A | 2/1976 | Chiyomaru et al. |
| 4,245,432 | A | 1/1981 | Dannelly |
| 4,272,417 | A | 6/1981 | Barke et al. |
| 4,808,430 | A | 2/1989 | Kouno |
| 5,223,526 | A | 6/1993 | McLoughlin et al. |
| 5,416,103 | A | 5/1995 | Eicken et al. |
| 5,521,317 | A | 5/1996 | Briner |
| 5,876,739 | A | 3/1999 | Turnblad et al. |
| 5,914,344 | A | 6/1999 | Yoshikawa et al. |
| 6,054,473 | A | 4/2000 | Elbe et al. |
| 6,107,336 | A | 8/2000 | Elbe et al. |
| 7,098,227 | B2 | 8/2006 | Dunkel et al. |
| 7,329,633 | B2 | 2/2008 | Dunkel et al. |
| 7,521,397 | B2 | 4/2009 | Dunkel et al. |
| 7,598,389 | B2 | 10/2009 | Dunkel et al. |
| 7,732,375 | B2 | 6/2010 | Dunkel et al. |
| 7,799,334 | B2 | 9/2010 | Gewehr et al. |
| 7,820,708 | B2 | 10/2010 | Dunkel et al. |
| 7,879,760 | B2 | 2/2011 | Dunkel et al. |
| 8,071,824 | B2 | 12/2011 | Straub et al. |
| 8,299,047 | B2 | 10/2012 | Dunkel et al. |
| 8,344,015 | B2 | 1/2013 | Dunkel et al. |
| 2003/0176428 | A1 | 9/2003 | Schneidersmann et al. |
| 2006/0116414 | A1 | 6/2006 | Dunkel et al. |
| 2007/0004921 | A1 | 1/2007 | Dunkel et al. |
| 2007/0037858 | A1 | 2/2007 | Dunkel et al. |
| 2007/0072930 | A1 | 3/2007 | Dunkel et al. |
| 2007/0203148 | A1 | 8/2007 | Dunkel et al. |
| 2008/0015244 | A1 | 1/2008 | Dunkel et al. |
| 2008/0194835 | A1 | 8/2008 | Jorges et al. |

(Continued)

FOREIGN PATENT DOCUMENTS

| CN | 1078234 C | 1/2002 |
| CN | 101175727 A | 5/2008 |

(Continued)

OTHER PUBLICATIONS

Patani et al, Chem. Rev. 1996, 96, 3147-3176.*
International Search Report for PCT/EP2011/070041 Mailed Feb. 1, 2012.
International Search Report of PCT/EP2011/070041 dated Feb. 1, 2012.
R. Wegler „Chemie der Pflanzenschutz- und Schäd¬lingsbekämpfungsmittel, Bd. 2, Springer Verlag, 1970, S. 401-412.
Joint Research Center "Deliberate Release and Placing on the EU Market of GMOs" http://gmoinfo.jrc.it/gmp_browse.aspx.
ILSI Research Foundation, International Life Sciences Institute, GM Crop Database http://www.agbios.com/dbase.php.

*Primary Examiner* — Kamal Saeed
(74) *Attorney, Agent, or Firm* — McBee Moore Woodward Vanik IP, LLC

(57) ABSTRACT

The present invention relates to novel 5-halogenopyrazole (thio)carboxamides, their process of preparation, their use as fungicide active agents, particularly in the form of fungicide compositions, and methods for the control of phytopathogenic fungi, notably of plants, using these compounds or compositions.

21 Claims, No Drawings

(56) References Cited

U.S. PATENT DOCUMENTS

| | | |
|---|---|---|
| 2009/0076113 A1 | 3/2009 | Dunkel et al. |
| 2009/0105311 A1 | 4/2009 | Dunkel et al. |
| 2009/0118346 A1 | 5/2009 | Dunkel et al. |
| 2009/0123561 A1 | 5/2009 | Gewehr et al. |
| 2009/0151024 A1 | 6/2009 | Dietz et al. |
| 2009/0176844 A1 | 7/2009 | Dunkel et al. |
| 2009/0192172 A1 | 7/2009 | Dunkel et al. |
| 2011/0257128 A1 | 10/2011 | Dunkel et al. |
| 2013/0172367 A1 | 7/2013 | Dunkel et al. |

FOREIGN PATENT DOCUMENTS

| | | |
|---|---|---|
| CN | 101212899 A | 7/2008 |
| CN | 101237773 A | 8/2008 |
| CN | 101262764 A | 9/2008 |
| DE | 2434430 A1 | 2/1975 |
| DE | 102004041531 | 3/2006 |
| DE | 102005009458 A1 | 9/2006 |
| DE | WO 2006131230 A2 * | 12/2006 |
| EP | 0589313 A1 | 3/1994 |
| EP | 0654464 A1 | 5/1995 |
| EP | 0769489 A1 | 4/1997 |
| EP | 0824099 A1 | 2/1998 |
| JP | 6296472 A | 5/1987 |
| JP | 09132552 A | 5/1997 |
| JP | 2007-509851 A | 4/2007 |
| JP | 2007520500 A | 7/2007 |
| JP | 2008-540491 A | 11/2008 |
| JP | 2009502747 A | 1/2009 |
| JP | 2010518179 A | 5/2010 |
| WO | 8910396 A1 | 11/1989 |
| WO | 93/11117 | 6/1993 |
| WO | 9311117 A1 | 6/1993 |
| WO | 9633270 A1 | 10/1996 |
| WO | 9803486 A1 | 1/1998 |
| WO | 9803495 A1 | 1/1998 |
| WO | 0228186 A2 | 4/2002 |
| WO | 0238542 A1 | 5/2002 |
| WO | 02059086 A1 | 8/2002 |
| WO | 02080675 A1 | 10/2002 |
| WO | 03066609 A1 | 8/2003 |
| WO | 03070705 A1 | 8/2003 |
| WO | 03074491 A1 | 9/2003 |
| WO | 2004014138 A1 | 2/2004 |
| WO | 2004035589 A1 | 4/2004 |
| WO | 2005-042480 A2 | 5/2005 |
| WO | 2005040110 A1 | 5/2005 |
| WO | 2005042493 A1 | 5/2005 |
| WO | 2005042494 A1 | 5/2005 |
| WO | 2005049624 A1 | 6/2005 |
| WO | 2005/075411 A1 | 8/2005 |
| WO | 2006061215 A2 | 6/2006 |
| WO | 2006087223 A1 | 8/2006 |
| WO | 2006087343 A1 | 8/2006 |
| WO | 2006-120219 A1 | 11/2006 |
| WO | 2007/006806 A2 | 1/2007 |
| WO | 2007/017409 A1 | 2/2007 |
| WO | 2007017450 A1 | 2/2007 |
| WO | 2007024782 A2 | 3/2007 |
| WO | 2007027777 A2 | 3/2007 |
| WO | 2007/068376 A1 | 6/2007 |
| WO | 2007068373 A1 | 6/2007 |
| WO | 2007068417 A2 | 6/2007 |
| WO | 2007071656 A1 | 6/2007 |
| WO | 2008006576 A1 | 1/2008 |
| WO | 2008014905 A2 | 2/2008 |
| WO | 2008014905 A3 | 4/2008 |
| WO | 2008095890 A2 | 8/2008 |
| WO | 2008098928 A2 | 8/2008 |
| WO | 2009029383 A1 | 3/2009 |
| WO | 2009135860 A1 | 11/2009 |

* cited by examiner

5-HALOGENOPYRAZOLECARBOXAMIDES

CROSS REFERENCE TO RELATED APPLICATIONS

This application is a §371 National Stage Application of PCT/EP2011/070041, filed Nov. 14, 2011, which claims priority to European Application No. 10191270.7; filed Nov. 15, 2010; European Application No. 10191269.9, filed Nov. 15, 2010; European Application No. 10191740.9, filed Nov. 18, 2010; European Application No. 10191761.5, filed Nov. 18, 2010; U.S. Provisional Application No. 61/416,828, filed Nov. 24, 2010; and European Application No. 11356008.0, filed Jun. 9, 2011.

BACKGROUND OF THE INVENTION

1. Field of the Invention

The present invention relates to novel 5-halogenopyrazole (thio)carboxamides, their process of preparation, their use as fungicide active agents, particularly in the form of fungicide compositions, and methods for the control of phytopathogenic fungi, notably of plants, using these compounds or compositions.

2. Description of Related Art

It is already known that numerous carboxamides have fungicidal properties (cf., for example, WO-A 1998/03495, WO-A 1998/03486 and EP-A 0 589 313). Thus, 1-methyl-3-trifluoromethyl-5-fluoro- and 1,3-dimethylfluoropyrazolecarboxamides are already known (WO-A 2006/061215, WO-A 2005/042494, WO-A 2005/042493, WO-A 2008/095890, WO-A 2004/035589, WO-A 2003/074491). The activity of these compounds is good; however, in some cases, for example at low application rates, it is sometimes unsatisfactory.

SUMMARY

This invention now provides novel 1-methyl-3-dihalogenomethyl-5-halogenopyrazole(thio)carboxamides of the formula (I)

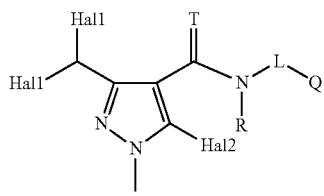

in which T represents an oxygen or sulfur atom;
R represents hydrogen, $C_1$-$C_6$-alkylsulfonyl, $C_1$-$C_4$-alkoxy-$C_1$-$C_4$-alkyl, $C_1$-$C_4$-haloalkylsulfonyl, halo-$C_1$-$C_4$-alkoxy-$C_1$-$C_4$-alkyl or formyl;
Hal1 and Hal2 independently of one another represent chlorine or fluorine;
L represents phenyl which may be substituted by up to 4 identical or different groups $R^1$;
Q represents phenyl which may be substituted by up to 5 identical or different groups $R^b$; or
Q represents halogen; nitro; cyano; isonitrile; hydroxyl; amino; sulfanyl; pentafluoro-λ6-sulfanyl; formyl; formyloxy; formylamino; optionally substituted (hydroxyimino)-$C_1$-$C_8$-alkyl; optionally substituted ($C_1$-$C_8$-alkoxyimino)-$C_1$-$C_8$-alkyl; optionally substituted ($C_2$-$C_8$-alkenyloxyimino)-$C_1$-$C_8$-alkyl; optionally substituted ($C_2$-$C_8$-alkynyloxyimino)-$C_1$-$C_8$-alkyl; optionally substituted (benzyloxyimino)-$C_1$-$C_8$-alkyl; carboxyl; carbamoyl; N-hydroxycarbamoyl; carbamate; optionally substituted $C_1$-$C_{16}$-alkyl; optionally substituted $C_2$-$C_8$-alkenyl; optionally substituted $C_2$-$C_8$-alkynyl; optionally substituted $C_1$-$C_{16}$-alkoxy; optionally substituted $C_1$-$C_8$-alkylsulfanyl; optionally substituted $C_1$-$C_8$-alkylsulfinyl; optionally substituted $C_1$-$C_8$-alkylsulfonyl; optionally substituted $C_1$-$C_8$-alkylamino; optionally substituted di-$C_1$-$C_8$-alkylamino; optionally substituted $C_2$-$C_8$-alkenyloxy; optionally substituted $C_3$-$C_8$-alkynyloxy; optionally substituted $C_3$-$C_8$-cycloalkyl; optionally substituted ($C_3$-$C_8$-cycloalkyl)-$C_1$-$C_8$-alkyl; optionally substituted ($C_3$-$C_8$-cycloalkyl)-($C_3$-$C_8$-cycloalkyl; optionally substituted ($C_3$-$C_8$-cycloalkyl)-$C_2$-$C_8$-alkenyl; optionally substituted ($C_3$-$C_8$-cycloalkyl)-$C_2$-$C_8$-alkynyl; optionally substituted tri($C_1$-$C_8$)alkylsilyl; optionally substituted tri($C_1$-$C_8$)alkylsilyl-$C_1$-$C_8$-alkyl; optionally substituted $C_1$-$C_8$-alkylcarbonyl; optionally substituted $C_1$-$C_8$-alkylcarbonyloxy; optionally substituted $C_1$-$C_8$-alkylcarbonylamino; optionally substituted $C_1$-$C_8$-alkoxycarbonyl; optionally substituted $C_1$-$C_8$-alkyloxycarbonyloxy; optionally substituted $C_1$-$C_8$-alkylcarbamoyl; optionally substituted di-$C_1$-$C_8$-alkylcarbamoyl; optionally substituted $C_1$-$C_8$-alkylaminocarbonyloxy; optionally substituted di-$C_1$-$C_8$-alkylaminocarbonyloxy; optionally substituted N—($C_1$-$C_8$-alkyl)hydroxycarbamoyl; optionally substituted $C_1$-$C_8$-alkoxycarbamoyl; optionally substituted N—($C_1$-$C_8$-alkyl)-$C_1$-$C_8$-alkoxycarbamoyl; $C_1$-$C_8$-arylalkyl which is optionally substituted by up to 6 identical or different groups $R^b$; $C_2$-$C_8$-arylalkenyl which is optionally substituted by up to 6 identical or different groups $R^b$; $C_2$-$C_8$-arylalkynyl which is optionally substituted by up to 6 identical or different groups $R^b$; aryloxy which is optionally substituted by up to 6 identical or different groups $R^b$; arylsulfanyl which is optionally substituted by up to 6 identical or different groups $R^b$; arylamino which is optionally substituted by up to 6 identical or different groups $R^b$; $C_1$-$C_8$-arylalkyloxy which is optionally substituted by up to 6 identical or different groups $R^b$; $C_1$-$C_8$-arylalkylsulfanyl which is optionally substituted by up to 6 identical or different groups $R^b$; $C_1$-$C_8$-arylalkylamino which is optionally substituted by up to 6 identical or different groups $R^b$ or a bicyclo[2.2.1]heptanyl group;

$R^1$, $R^b$ independently of one another represent halogen; nitro, cyano, $C_1$-$C_{12}$-alkyl; $C_1$-$C_6$-haloalkyl having 1 to 9 identical or different halogen atoms; $C_1$-$C_6$-alkoxy; $C_1$-$C_6$-haloalkoxy having 1 to 9 identical or different halogen atoms; $C_1$-$C_6$-alkylsulfanyl; $C_1$-$C_6$-haloalkylsulfanyl having 1 to 9 identical or different halogen atoms; $C_1$-$C_6$-alkylsulfonyl; $C_1$-$C_6$-haloalkylsulfonyl having 1 to 9 identical or different halogen atoms; $C_2$-$C_{12}$-alkenyl; $C_2$-$C_{12}$-alkynyl; $C_3$-$C_7$-cycloalkyl; phenyl; tri($C_1$-$C_8$)alkylsilyl; tri($C_1$-$C_8$)alkylsilyl-$C_1$-$C_8$-alkyl;

where, unless indicated otherwise, a group or a substituent which is substituted according to the invention may be substituted by one or more $R^b$; or Q and $R^1$ together with the carbon atoms to which they are attached form an optionally substituted 5-, 6- or 7-membered carbocyclic or saturated heterocyclic ring; or Q and L together form a radical of the formula ($W^1$),

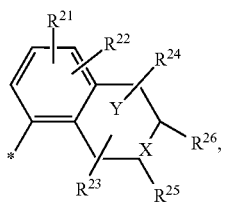

(W1)

where
the bond marked by * is attached to the amide;
X represents a single bond or a double bond;
Y represents oxygen, sulfur, $N(R^{27})$ or $(CR^{28}R^{29})(CR^{30}R^{31})_m(CR^{32}R^{33})_n$;
m represents 0 or 1;
n represents 0 or 1;
$R^{21}$ and $R^{22}$ independently of one another represent hydrogen, halogen, $C_1$-$C_4$-alkyl, $C_1$-$C_4$-alkoxy or $C_1$-$C_4$-haloalkoxy;
$R^{23}$, $R^{24}$, $R^{25}$ and $R^{26}$ independently of one another represent hydrogen, halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfanyl, $C_1$-$C_4$-haloalkylsulfanyl, hydroxymethyl, $C_{1-4}$-alkoxymethyl, C(O)CH$_3$ or C(O)OCH$_3$;
$R^{27}$ represents hydrogen, $C_1$-$C_4$-alkyl, benzyl (where the phenyl group is optionally substituted up to three times by a radical independently selected from the group consisting of halogen, $C_1$-$C_4$-alkyl, $C_1$-$C_4$-haloalkyl and $C_1$-$C_4$-alkoxy), formyl, C(O)$C_1$-$C_4$-alkyl (optionally substituted by halogen or $C_1$-$C_4$-alkoxy), C(=O)O—$C_1$-$C_6$-alkyl (optionally substituted by halogen, $C_1$-$C_4$-alkoxy or cyano) or $C_1$-$C_4$-alkoxy-($C_1$-$C_4$)-alkylene;
$R^{28}$, $R^{29}$, $R^{30}$, $R^{31}$, $R^{32}$ and $R^{33}$ independently of one another represent hydrogen, halogen, hydroxyl, $C_1$-$C_4$-alkoxy, $C_1$-$C_6$-alkyl [optionally substituted by halogen, hydroxyl, $C_1$-$C_4$-alkoxy, =O, aryl, O—C(O)—$C_1$-$C_4$-alkyl or a 3-7-membered carbocyclic ring (which is itself optionally substituted by up to three methyl groups)] or $C_2$-$C_6$-alkenyl [optionally substituted by halogen, hydroxyl, $C_1$-$C_4$-alkoxy, =O, aryl, O—C(O)—$C_1$-$C_4$-alkyl or a 3-7-membered carbocyclic ring (which is itself optionally substituted by up to three methyl groups)] or a 3-7-membered saturated ring (which is optionally substituted by up to three methyl groups and optionally contains a heteroatom selected from the group consisting of nitrogen and oxygen); or
$R^{28}$ and $R^{29}$ together with the carbon atom to which they are attached form a group C=O or a three- to five-membered carbocyclic ring (which is optionally substituted by up to three methyl groups and optionally contains up to two heteroatoms independently selected from the group consisting of nitrogen and oxygen); or
$R^{28}$ and $R^{29}$ together form a $C_1$-$C_6$-alkylidene (which is optionally substituted by up to four groups that can be the same or different and that can be selected in the list consisting of fluorine, chlorine, bromine, methyl) or a $C_3$-$C_6$-cycloalkylidene group (which is optionally substituted by up to three methyl groups).

DETAILED DESCRIPTION OF A PREFERRED EMBODIMENT

The formula (I) provides a general definition of the 1-methyl-3-dihalogenomethyl-5-halogenopyrazole(thio)carboxamides according to the invention. Preferred radical definitions for the formulae shown above and below are given below. These definitions apply to the end products of the formula (I) and likewise to all intermediates.

T preferably represents an oxygen atom.
R preferably represents hydrogen, $C_1$-$C_4$-alkylsulfonyl, $C_1$-$C_3$-alkoxy-$C_1$-$C_3$-alkyl, $C_1$-$C_4$-haloalkylsulfonyl, halo-$C_1$-$C_3$-alkoxy-$C_1$-$C_3$-alkyl having in each case 1 to 9 fluorine, chlorine and/or bromine atoms; or formyl.
R particularly preferably represents hydrogen, methylsulfonyl, ethylsulfonyl, n- or isopropylsulfonyl, n-, iso-, sec- or tert-butylsulfonyl, methoxymethyl, methoxyethyl, ethoxymethyl, ethoxyethyl, trifluoromethylsulfonyl, trifluoromethoxymethyl or formyl.
R very particularly preferably represents hydrogen, methoxymethyl, or formyl.
Hal1 preferably represents chlorine.
Hal1 preferably represents fluorine.
Hal2 preferably represents chlorine.
Hal2 preferably represents fluorine.
L preferably represents

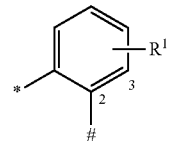

L-1

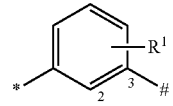

L-2 where the bond marked by * is attached to the amide while the bond marked # is attached to Q;
$R^1$ is as defined herein or
$R^1$ and Q together with the carbon atoms to which they are attached form an optionally substituted 5- or 6-membered carbocyclic or heterocyclic ring.
L particularly preferably represents L–1;
L moreover particularly preferably represents L–2;
$R^1$ preferably represents hydrogen, fluorine, chlorine, methyl or trifluoromethyl.
$R^1$ particularly preferably represents hydrogen.
$R^1$ moreover particularly preferably represents fluorine, where fluorine is particularly preferably located in the 4-, 5- or 6-position, very particularly preferably in the 4- or 6-position, in particular in the 4-position of the anilide radical [cf. formula (I) above].
$R^1$ moreover particularly preferably represents chlorine, where chlorine is particularly preferably located in the 5-position of the anilide radical [cf. formula (I) above]. Chlorine is furthermore particularly preferably located in the 4-position of the anilide radical.
$R^1$ moreover particularly preferably represents methyl, where methyl is particularly preferably located in the 3-position of the anilide radical [cf. formula (I) above].
$R^1$ moreover particularly preferably represents trifluoromethyl, where trifluoromethyl is particularly preferably located in the 4- or 5-position of the anilide radical [cf. formula (I) above].
Q and $R^1$ together with the carbon atoms to which they are attached preferably represent a 5- or 6-membered carbocyclic or saturated heterocyclic ring which is optionally mono- to tetrasubstituted by identical or different substituents.

Q and $R^1$ together with the carbon atoms to which they are attached particularly preferably represent a 5- or 6-membered carbocyclic ring which is optionally mono-, di- or trisubstituted by methyl.

Q and $R^1$ together with the carbon atoms to which they are attached particularly preferably represent a 5- or 6-membered saturated heterocyclic ring containing one oxygen atom and which is optionally mono-, di- or trisubstituted by methyl.

L particularly preferably represents L–1 wherein Q and $R^1$ together with the carbon atoms to which they are attached very particularly preferably represent a 5- or 6-membered carbocyclic ring which is optionally mono-, di- or trisubstituted by methyl L particularly preferably represents L–1 wherein Q and $R^1$ together with the carbon atoms to which they are attached very particularly preferably represent a 5- or 6-membered saturated heterocyclic ring containing one oxygen atom and which is optionally mono-, di- or trisubstituted by methyl.

Q preferably represents $Q^1$, $Q^2$, $Q^3$, $Q^4$, $Q^5$, or $Q^6$ $Q^1$ represents

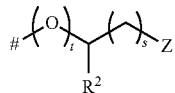

where the bond marked # is attached to L;

$R^2$ represents hydrogen, $C_1$-$C_4$-alkyl or $C_1$-$C_4$-haloalkyl.

$R^2$ particularly preferably represents hydrogen, fluorine, chlorine, methyl, ethyl, n- or isopropyl, or represents methyl, ethyl, n- or isopropyl, n-, iso-, sec- or tert-butyl, each of which is mono- or polysubstituted by identical or different substituents from the group consisting of fluorine, chlorine and bromine $R^2$ very particularly preferably represents hydrogen, fluorine, chlorine, methyl, ethyl, trifluoromethyl, difluoromethyl, fluoromethyl, trichloromethyl, dichloromethyl, chloromethyl, chlorofluoromethyl, fluorodichloromethyl, difluorochloromethyl, pentafluoroethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2-chloro-2,2-difluoroethyl, 2-dichloro-2-fluoroethyl, 2,2,2-trichloroethyl, 1-chlorobutyl, heptafluoro-n-propyl or heptafluoroisopropyl.

$R^2$ very particularly preferably represents hydrogen, methyl or ethyl.

$R^2$ especially preferably represents hydrogen or methyl.

Z represents —$CR^3R^4R^5$ or —$SiR^3R^4R^5$.

Z particularly preferably represents —$CR^3R^4R^5$.

Z moreover particularly preferably represents —$SiR^3R^4R^5$.

s represents 0, 1, 2 or 3.

s particularly preferably represents 0.

s particularly preferably represents 1.

s moreover particularly preferably represents 2.

s very particularly preferably represents 1.

t represents 0 or 1.

t particularly preferably represents 0.

t particularly preferably represents 1.

providing that $R^2$ is not hydrogen, methyl or ethyl when Z is —$CR^3R^4R^5$ and s represents 1 and t represents 0.

$R^3$, $R^4$, $R^5$ independently of one another represent hydrogen, $C_1$-$C_8$-alkyl or $C_1$-$C_6$-haloalkyl, or $R^3$ and $R^4$ together with the carbon atom to which they are attached form a 3- to 6-membered carbocyclic saturated or unsaturated ring.

$R^3$ particularly preferably represents fluorine, chlorine, bromine, methyl, ethyl, n- or isopropyl, n-, iso-, sec- or tert-butyl or represents methyl, ethyl, n- or isopropyl, n-, iso-, sec- or tert-butyl, each of which is mono- or polysubstituted by identical or different substituents from the group consisting of fluorine, chlorine and bromine.

$R^3$ particularly preferably represents fluorine, chlorine, methyl, ethyl, n- or isopropyl, n-, iso-, sec- or tert-butyl, trifluoromethyl, difluoromethyl, fluoromethyl, trichloromethyl, dichloromethyl, chloromethyl, chlorofluoromethyl, fluorodichloromethyl, difluorochloromethyl, pentafluoroethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2-chloro-2,2-difluoroethyl, 2-dichloro-2-fluoroethyl, 2,2,2-trichloroethyl, 1-chlorobutyl, heptafluoro-n-propyl or heptafluoroisopropyl.

$R^3$ especially very preferably represents chlorine, methyl, ethyl, isopropyl or trifluoromethyl.

$R^4$ particularly preferably represents fluorine, chlorine, bromine, methyl, ethyl, n- or isopropyl, n-, iso-, sec- or tert-butyl or represents methyl, ethyl, n- or isopropyl, n-, iso-, sec- or tert-butyl, each of which is mono- or polysubstituted by identical or different substituents from the group consisting of fluorine, chlorine and bromine.

$R^4$ especially preferably represents fluorine, chlorine, methyl, ethyl, n- or isopropyl, n-, iso-, sec- or tert-butyl, trifluoromethyl, difluoromethyl, fluoromethyl, trichloromethyl, dichloromethyl, chloromethyl, chlorofluoromethyl, fluorodichloromethyl, difluorochloromethyl, pentafluoroethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2-chloro-2,2-difluoroethyl, 2-dichloro-2-fluoroethyl, 2,2,2-trichloroethyl, 1-chlorobutyl, heptafluoro-n-propyl or heptafluoroisopropyl.

$R^4$ especially very preferably represents chlorine, methyl, ethyl, isopropyl or trifluoromethyl.

$R^5$ particularly preferably represents hydrogen, fluorine, chlorine, bromine, methyl, ethyl, n- or isopropyl, n-, iso-, sec- or tert-butyl or represents methyl, ethyl, n- or isopropyl, n-, iso-, sec- or tert-butyl, each of which is mono- or polysubstituted by identical or different substituents from the group consisting of fluorine, chlorine and bromine.

$R^5$ particularly preferably represents hydrogen, fluorine, chlorine, methyl, ethyl, n- or isopropyl, iso-, sec- or tert-butyl, trifluoromethyl, difluoromethyl, fluoromethyl, trichloromethyl, dichloromethyl, chloromethyl, chlorofluoromethyl, fluorodichloromethyl, difluorochloromethyl, pentafluoroethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2-chloro-2,2-difluoroethyl, 2-dichloro-2-fluoroethyl, 2,2,2-trichloroethyl, 1-chlorobutyl, heptafluoro-n-propyl or heptafluoroisopropyl.

$R^5$ especially very preferably represents hydrogen, chlorine, methyl, ethyl, isopropyl or trifluoromethyl.

$R^3$ and $R^4$ moreover together with the carbon atom to which they are attached particularly preferably form a 3- to 6-membered carbocyclic or heterocyclic saturated or unsaturated ring which is optionally substituted by halogen, methyl, ethyl, methoxy, trifluoromethyl or trifluoromethoxy, $R^3$ and $R^4$ moreover together with the carbon atom to which they are attached particularly preferably form a 3-, 5- or 6-membered carbocyclic saturated ring which is optionally substituted by methyl, ethyl or trifluoromethyl, $R^3$ and $R^4$ moreover together with the carbon atom to which they are attached especially very preferably form a 6-membered carbocyclic unsaturated ring which is optionally substituted by halogen, methyl, ethyl, methoxy, trifluoromethyl or trifluoromethoxy.

$Q^2$ represents

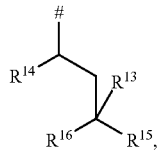

where the bond marked # is attached to L.

$R^{13}$ represents hydrogen, halogen, $C_1$-$C_8$-alkyl or $C_1$-$C_8$-haloalkyl.

$R^{13}$ particularly preferably represents fluorine, chlorine, bromine, iodine, $C_1$-$C_6$-alkyl, $C_1$-$C_6$-haloalkyl having in each case 1 to 13 fluorine, chlorine and/or bromine atoms.

$R^{13}$ very particularly preferably represents fluorine, chlorine, bromine, methyl, ethyl, n-, isopropyl, n-, iso-, sec-, tert-butyl or represents $C_1$-$C_4$-haloalkyl having in each case 1 to 9 fluorine, chlorine and/or bromine atoms.

$R^{13}$ especially very preferably represents fluorine, chlorine, methyl, ethyl or trifluoromethyl.

$R^{14}$, $R^{15}$ and $R^{16}$ independently of one another represent hydrogen, methyl or ethyl;

$R^{14}$, $R^{15}$ and $R^{16}$ independently of one another particularly preferably represent methyl or hydrogen;

$R^{14}$, $R^{15}$ very particularly preferably represent methyl or hydrogen; whereas $R^{16}$ represents hydrogen.

$Q^3$ represents

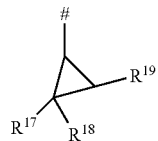

where the bond marked # is attached to L;

$R^{17}$ represents hydrogen or halogen.

$R^{18}$ represents hydrogen or halogen.

$R^{17}$ and $R^{18}$ independently of one another particularly preferably represent hydrogen, fluorine, chlorine or bromine;

$R^{17}$ and $R^{18}$ independently of one another very particularly preferably represent hydrogen or fluorine;

$R^{17}$ and $R^{18}$ especially very particularly preferably represent hydrogen;

$R^{19}$ represents optionally substituted $C_2$-$C_{12}$-alkyl, optionally substituted $C_2$-$C_{12}$-alkenyl, optionally substituted $C_2$-$C_{12}$-alkynyl, optionally substituted $C_3$-$C_{12}$-cycloalkyl, optionally substituted phenyl or heterocyclyl.

$R^{19}$ particularly preferably represents $C_2$-$C_6$-alkyl, optionally substituted $C_3$-$C_8$-cycloalkyl, optionally substituted phenyl, pyridyl, thienyl or furyl;

$R^{19}$ very particularly preferably represents ethyl, n-propyl, isopropyl, n-butyl, sec-butyl, tert-butyl, n-pentyl, neopentyl, isopentyl, n-hexyl, isohexyl, n-heptyl, cyclopropyl, cyclobutyl, cyclopentyl, cyclohexyl, cycloheptyl, cyclooctyl, a-methylcyclopropyl, 2-, 3- or 4-halo-substituted phenyl, 2-thienyl, 3-thienyl or 2-furyl;

$R^{19}$ especially very particularly preferably represents ethyl, n-propyl, isopropyl, n-butyl, sec-butyl, tert-butyl, cyclopropyl, cyclobutyl, cyclopentyl, cyclohexyl, a-methylcyclopropyl, 4-fluorophenyl, 4-bromophenyl, 4-chlorophenyl, 2-thienyl, 3-thienyl or 2-furyl.

$Q^4$ represents

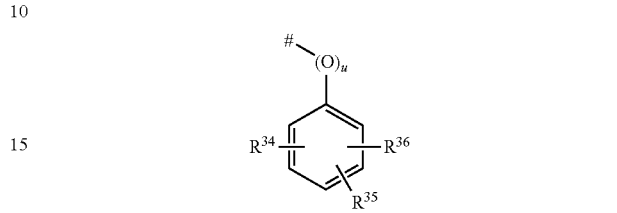

where the bond marked # is attached to L, $R^{34}$, $R^{35}$ and $R^{36}$ independently of one another represent halogen, cyano, nitro, $C_1$-$C_6$-alkyl, $C_2$-$C_6$-alkenyl, $C_1$-$C_4$-alkoxy, $C_1$-$C_4$-alkylsulfanyl, $C_1$-$C_4$-alkylsulfonyl, $C_3$-$C_6$-cycloalkyl, or represent $C_1$-$C_4$-haloalkyl, $C_1$-$C_4$-haloalkoxy, $C_1$-$C_4$-haloalkylsulfanyl or $C_1$-$C_4$-haloalkylsulfonyl having in each case 1 to 5 halogen atoms.

$R^{34}$, $R^{35}$ and $R^{36}$ independently of one another particularly preferably represent fluorine, chlorine, bromine, cyano, nitro, methyl, ethyl, n- or isopropyl, n-, i-, s- or t-butyl, methoxy, ethoxy, methylsulfanyl, ethylsulfanyl, n- or isopropylsulfanyl, cyclopropyl, trifluoromethyl, trichloromethyl, trifluoroethyl, difluoromethoxy, trifluoromethoxy, difluorochloromethoxy, trifluoroethoxy, difluoromethylsulfanyl, difluorochloromethylsulfanyl or trifluoromethylsulfanyl.

$R^{34}$, $R^{35}$ and $R^{36}$ independently of one another very particularly preferably represent fluorine, chlorine, bromine, methyl, trifluoromethyl, difluoromethoxy or trifluoromethoxy.

$R^{34}$, $R^{35}$ and $R^{36}$ independently of one another especially very preferably represent fluorine, chlorine, bromine u represents 0 or 1.

u particularly preferably represents 0.

u particularly preferably represents 1.

$Q^5$ represents

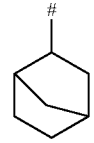

where the bond marked # is attached to L.

$Q^6$ represents

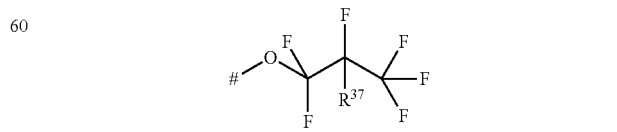

where $R^{37}$ represents hydrogen or fluorine and where the bond marked # is attached to L.

X preferably represents a single bond.

Y preferably represents oxygen, sulfur, N(R$^{27}$), CH$_2$, CH$_2$CH$_2$, CH$_2$CH$_2$CH$_2$, C(CH$_3$)$_2$, CH(CH$_3$), CH(C$_2$H5), C(CH$_3$)(C$_2$H5), CH(OCH$_3$) or C(OCH$_3$)$_2$;

Y particularly preferably represents N(R$^{27}$), oxygen, sulfur, CH$_2$, CH$_2$CH$_2$, CH$_2$CH$_2$CH$_2$, C(CH$_3$)$_2$, CH(CH$_3$) or CH(C$_2$H5);

Y very particularly preferably represents N(R$^{27}$), oxygen, sulfur, CH$_2$ or CH$_2$CH$_2$;

Y particularly preferably represents oxygen, CH$_2$ or N(R$^{27}$).

Y preferably represents oxygen, N(R$^{27}$) or (CR$^{28}$R$^{29}$)(CR$^{30}$R$^{31}$)$_m$(CR$^{32}$R$^{33}$)$_n$.

Y particularly preferably represents oxygen or (CR$^{28}$R$^{29}$)(CR$^{30}$R$^{31}$)$_m$(CR$^{32}$R$^{33}$)$_n$.

Y very particularly preferably represents (CR$^{28}$R$^{29}$)(CR$^{30}$R$^{31}$)$_m$(CR$^{32}$R$^{33}$)$_n$.

Y very particularly preferably represents (CR$^{28}$R$^{29}$).

n preferably represents 0.

m preferably represents 0.

R$^{21}$ preferably represents hydrogen, halogen or C$_1$-C$_4$-alkyl.

R$^{21}$ particularly preferably represents hydrogen or halogen.

R$^{21}$ very particularly preferably represents hydrogen.

R$^{22}$ preferably represents hydrogen or methyl.

R$^{22}$ particularly preferably represents hydrogen.

R$^{23}$ preferably represents hydrogen, C$_1$-C$_4$-alkyl, halogen, C$_1$-C$_4$-haloalkyl, C$_1$-C$_4$-alkoxy, C(O)CH$_3$ or C(O)OCH$_3$.

R$^{23}$ particularly preferably represents hydrogen, C$_1$-C$_2$-alkyl, halogen, CF$_3$, methoxy, C(O)CH$_3$ or C(O)OCH$_3$.

R$^{23}$ very particularly preferably represents hydrogen, methyl, chlorine, CF$_3$ or methoxy.

R$^{23}$ very particularly preferably represents hydrogen or methyl.

R$^{24}$ preferably represents hydrogen, C$_1$-C$_4$-alkyl, halogen, C$_1$-C$_4$-haloalkyl, C$_1$-C$_4$-alkoxy, C(O)CH$_3$ or C(O)OCH$_3$.

R$^{24}$ particularly preferably represents hydrogen, C$_1$-C$_2$-alkyl, chlorine, CF$_3$, methoxy, C(O)CH$_3$ or C(O)OCH$_3$.

R$^{24}$ very particularly preferably represents hydrogen or methyl.

R$^{25}$ preferably represents hydrogen, C$_1$-C$_4$-alkyl, C$_1$-C$_4$-alkoxy or C(O)CH$_3$.

R$^{25}$ particularly preferably represents hydrogen or methyl, methoxy or C(O)CH$_3$.

Very particularly preferably, R$^{25}$ represents hydrogen or methyl.

R$^{26}$ preferably represents hydrogen, C$_1$-C$_4$-alkyl, C$_1$-C$_4$-alkoxy or C(O)CH$_3$.

R$^{26}$ particularly preferably represents hydrogen or methyl, methoxy or C(O)CH$_3$.

R$^{26}$ very particularly preferably represents hydrogen or methyl.

R$^{27}$ preferably represents hydrogen, C$_1$-C$_4$-alkyl, benzyl (where the phenyl group is optionally substituted up to three times by a radical independently selected from the group consisting of halogen, C$_1$-C$_4$-alkyl, C$_1$-C$_4$-haloalkyl and C$_1$-C$_4$-alkoxy), formyl, C(O)C$_1$-C$_4$-alkyl or C$_1$-C$_4$-alkoxy-(C$_1$-C$_4$)-alkylene;

R$^{27}$ preferably represents hydrogen, C$_1$-C$_4$-alkyl, benzyl, formyl, C(O)CH$_3$ or C(O)OC(CH$_3$)$_3$;

R$^{27}$ particularly preferably represents hydrogen or C$_1$-C$_2$-alkyl.

R$^{27}$ preferably represents C$_1$-C$_4$-alkyl, formyl, C(O)CH$_3$ or C(O)OC$_1$-C$_6$-alkyl (optionally substituted by halogen, CN or C$_1$-C$_4$-alkoxy).

R$^{27}$ particularly preferably represents C(O)OC$_1$-C$_4$-alkyl.

R$^{28}$, R$^{29}$, R$^{30}$, R$^{31}$, R$^{32}$ and R$^{33}$ independently of one another preferably represent hydrogen, C$_1$-C$_4$-alkyl or C$_1$-C$_4$-alkoxy.

R$^{28}$, R$^{29}$, R$^{30}$, R$^{31}$, R$^{32}$ and R$^{33}$ independently of one another are preferably hydrogen, C$_1$-C$_2$-alkyl or methoxy.

R$^{28}$ and R$^{29}$ independently of one another are preferably hydrogen, halogen, C$_1$-C$_5$-alkyl, C$_1$-C$_3$-alkoxy, CH$_2$OH, CH(O), C$_3$-C$_6$-cycloalkyl, CH$_2$O—C(=O)CH$_3$, CH$_2$—C$_3$-C$_6$-cycloalkyl or benzyl; or R$^{28}$ and R$^{29}$ together with the carbon atom to which they are attached form a group C=O or a three- to five-membered carbocyclic ring; or R$^{28}$ and R$^{29}$ together form a C$_1$-C$_5$-alkylidene, a dichlorovinylidene or a C$_3$-C$_6$-cycloalkylidene group.

R$^{28}$ and R$^{29}$ independently of one another particularly preferably represent hydrogen, methyl, ethyl, n-C$_3$H$_7$, i-C$_3$H$_7$, n-C$_4$H$_9$, sec-C$_4$H$_9$, i-C$_4$H$_9$, CH(C$_2$H$_5$)$_2$, CH$_2$-cyclopropyl or cyclopentyl; or R$^{28}$ and R$^{29}$ together with the carbon atom to which they are attached form a three- to five-membered carbocyclic ring.

R$^{30}$ preferably represents hydrogen or methyl.

R$^{31}$ preferably represents hydrogen or methyl.

R$^{32}$ preferably represents hydrogen or methyl.

R$^{33}$ preferably represents hydrogen or methyl.

Preference is given to compounds of the formula (I) in which all radicals in each case have the preferred meanings mentioned above.

Particular preference is given to compounds of the formula (I) in which all radicals in each case have the particularly preferred meanings mentioned above.

Very particular preference is given to compounds of the formula (I) in which all radicals in each case have the very particularly preferred meanings mentioned above.

Special very particular preference is given to compounds of the formula (I) in which all radicals in each case have the especially very particularly preferred meanings mentioned above.

The following groups of novel (thio)carboxamides of the formulae

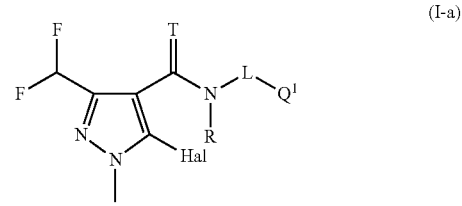

(I-a)

in which T, R, L, Q$^1$ have the meanings given above and Hal represents fluorine or chlorine;

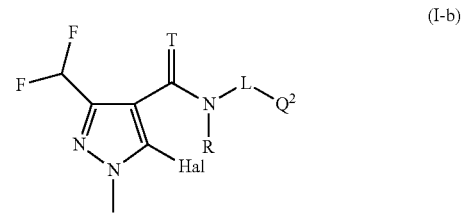

(I-b)

in which T, R, L, Q$^2$ have the meanings given above and Hal represents fluorine or chlorine;

(I-c)

in which T, R, L, Q³ have the meanings given above and Hal represents fluorine or chlorine;

(I-d)

in which T, R, L, Q⁴ have the meanings given above and Hal represents fluorine or chlorine;

(I-e)

in which T, R, L, Q⁵ have the meanings given above and Hal represents fluorine or chlorine;

(I-f)

in which T, R, L, Q⁶ have the meanings given above and Hal represents fluorine or chlorine;

(I-g)

in which T, R, R²¹, R²², R²³, R²⁴, R²⁵, R²⁶ have the meanings given above and Hal represents fluorine or chlorine;

are preferred and in each case to be understood as a subset of the compounds of the formula (I) mentioned above.

The following groups of novel (thio)carboxamides of the formulae (I-h)

in which T, R, L and Q have the meanings given above and Hal represents fluorine;

(I-i)

in which T, R, L and Q have the meanings given above and Hal represents chlorine;

are preferred and in each case to be understood as a subset of the compounds of the formula (I) mentioned above.

Very particular special preference is given to compounds of the formula (I) where T represents oxygen;
R represents hydrogen;
Hal1 represents fluorine;
L represents L-1 or L-2;
Q represents $Q^1$, $Q^2$, $Q^3$, $Q^4$, $Q^5$, or $Q^6$;
$R^1$ represents hydrogen or fluorine;
$Q^1$ represents where the bond marked # is attached to L,
$R^2$ represents hydrogen, methyl or ethyl,
Z represents —$CR^3R^4R^5$ or —$SiR^3R^4R^5$;
s represents 0, 1, 2 or 3;
t represents 0,
$R^3$, $R^4$, $R^5$ independently of one another represent hydrogen or methyl;

$Q^2$ represents

[structure with $R^{14}$, $R^{13}$, $R^{15}$, $R^{16}$ and bond marked #]

where the bond marked # is attached to L;
$R^{13, 15, 16}$ independently of one another represent hydrogen or methyl;
$R^{14}$ represents hydrogen, methyl or ethyl,
$Q^3$ represents

[cyclopropyl structure with $R^{17}$, $R^{18}$, $R^{19}$ and bond marked #]

where the bond marked # is attached to L;
$R^{17, 18}$ represents hydrogen;
$R^{19}$ represents cyclopropyl;
$Q^4$ represents

[phenyl structure with $(O)_u$, $R^{34}$, $R^{35}$, $R^{36}$ and bond marked #]

u represents 0,
$R^{34}$, $R^{35}$ and $R^{36}$ independently of one another represent F, Cl, Br or trifluoromethyl, where the bond marked # is attached to L;
$Q^5$ represents

[bicyclic structure with bond marked #]

$Q^6$ represents

[fluorinated structure with O, F atoms and bond marked #]

or Q and L together form a radical of the formula ($W^{1-A}$), where the bond marked * is attached the amide, ($W^{1-A}$)

[bicyclic aromatic structure with * marker and gem-dimethyl]

or Q and L together form a radical of the formula ($W^{1-B}$), where the bond marked * is attached to the amide, ($W^{1-B}$)

[bicyclic aromatic structure with * marker and =CCl$_2$ group]

Saturated or unsaturated hydrocarbon radicals, such as alkyl or alkenyl, can in each case be straight-chain or branched as far as this is possible, including in combination with heteroatoms, such as, for example, in alkoxy.

The aryl moiety contained in an aryl group, an arylalkyl group, an arylalkenyl group and an arylalkynyl group as well as moieties containing these terms, can be a phenyl group that can be substituted by up to 5 groups $R^b$ which can be the same or different, a naphthyl group that can be substituted by up to 6 groups $R^b$ which can be the same or different.

Optionally substituted radicals can be mono- or polysubstituted, where in the case of polysubstitution the substituents can be identical or different. Thus, the definition dialkylamino also includes an amino group which is unsymmetrically substituted by alkyl, such as, for example, methylethylamino.

Halogen-substituted radicals, such as, for example, halogenoalkyl, are mono- or polyhalogenated. In the case of polyhalogenation, the halogen atoms can be identical or different. Halogen denotes fluorine, chlorine, bromine and iodine, in particular fluorine, chlorine and bromine.

The compounds according to the invention may, if appropriate, be present as mixtures of various possible isomeric forms, in particular stereoisomers such as, for example, E and Z, threo and erythro, and also optical isomers, and, if appropriate, also of tautomers. What is claimed are both the E and the Z isomers, and also the threo and erythro, and also the optical isomers, any mixtures of these isomers, and also the possible tautomeric forms.

In the variations according to the invention of Q, up to two stereocentres (*) are present. What is claimed are all diastereomers and enantiomers, in particular of the following radicals

[structure with L, $R^{14}$, $R^{13}$, $R^{15}$, $R^{16}$ and * markers]

The abovementioned general or preferred radical definitions or illustrations can be combined as desired between the respective ranges and preferred ranges. They apply both to the end products and, correspondingly, to precursors and intermediates. In particular the compounds mentioned in groups (I-a) to (I-i) can be combined both with the general and the preferred, particularly preferred, etc., meanings, where here, too, in each case all combinations between the preferred ranges are possible.

Finally, it has been found that the novel 1-methyl-3-dihalogenomethyl-5-halogenopyrazole(thio)carboxamides of the formula (I) have very good microbicidal properties and can be used for controlling unwanted microorganisms both in crop protection and in the protection of materials.

Furthermore, it has been found that 1-methyl-3-dihalogenomethyl-5-halogenopyrazolecarboxamides of the formula (I) wherein T represents an oxygen atom, are obtained when carboxylic acid derivatives of the formula (II)

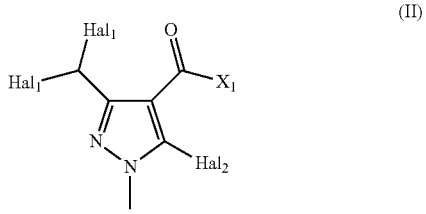

(II)

in which
$X^1$ represents halogen or hydroxyl,
Hal1 and Hal2 independently of one another represent chlorine or fluorine;
are reacted with amine derivatives of the formula (III)

(III)

in which R, L and Q have the meanings given above,
if appropriate in the presence of a catalyst, if appropriate in the presence of a condensing agent, if appropriate in the presence of an acid binder and if appropriate in the presence of a diluent.

This process for synthesizing such amides of the formula (I) has already been described sufficiently: WO-A 2006/061215, WO-A 2005/042494, WO-A 2005/042493, WO-A 2008/095890, WO-A 2004/035589, WO-A 2003/074491.

The acids and acid halides of the formula (II) used

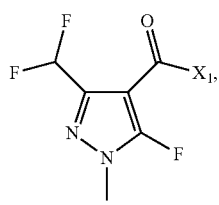

(II)

in which
$X^1$ represents halogen or hydroxyl,
are novel and are synthesized as described below:
Preference is given to compounds of the formula (II) where $X^1$ represents hydroxyl, chlorine or fluorine.

A further aspect of the invention comprises the process P1 according to the invention for synthesizing the acid chlorides of the formula (II), as shown in the reaction scheme below:

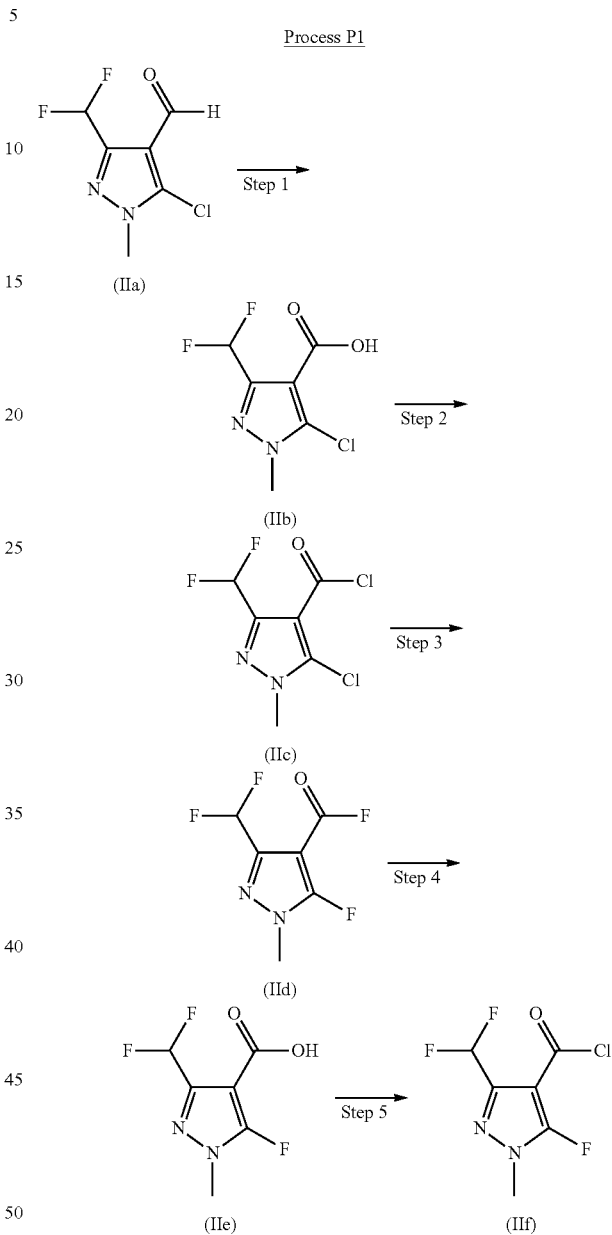

The compound of the formula (IIa), 5-chloro-3-(difluoromethyl)-1-methyl-1H-pyrazole-4-carbaldehyde, is known from WO-A 2004/014138 (Example 35).

Step 1 in process P1 according to the invention is carried out in the presence of an oxidizing agent and, if required, in the presence of a solvent.

Steps 2 and 5 in process P1 according to the invention are carried out in the presence of an acid halide former and, if required, in the presence of a solvent.

Step 3 in process P1 according to the invention is carried out in the presence of a fluorinating agent and, if required, in the presence of a solvent.

Step 4 in process P1 according to the invention is carried out in the presence of an acid or a base and, if required, in the presence of a solvent.

Suitable oxidizing agents for carrying out step 1 of process P1 according to the invention are all inorganic and organic oxidizing agents customarily used for such reactions.

Preference is given to benzyltriethylammonium permanganate, bromine, chlorine, m-chloroperbenzoic acid, chromic acid, chromium(VI) oxide, hydrogen peroxide, hydrogen peroxide/boron trifluoride, hydrogen peroxide/urea adduct, 2-hydroxyperoxyhexafluoro-2-propanol, iodine, perbenzoic acid, peroxyacetyl nitrate, potassium permanganate, potassium ruthenate, pyridinium dichromate, ruthenium(VIII) oxide, silver(I) oxide, silver(II) oxide, silver nitrite, sodium chlorite, sodium hypochlorite, 2,2,6,6-tetramethylpiperidine-1-oxyl.

Suitable acid halide formers for step 2 and step 5 of process P1 according to the invention are all organic and inorganic acid halide formers customarily used for such reactions.

Preference is given to phosgene, phosphorus trichloride, phosphorus pentachloride, phosphorus oxytrichloride; thionyl chloride; or carbon tetrachloride/triphenylphosphine.

Suitable fluorinating agents for step 3 of process P1 according to the invention are those which are customarily used for such reactions.

Preference is given to caesium fluoride; potassium fluoride; potassium fluoride/calcium difluoride and also tetrabutylammonium fluoride.

Suitable solvents for steps 1 to 5 of process P1 according to the invention are all customary inert organic solvents.

Preference is given to using optionally halogenated aliphatic, alicyclic or aromatic hydrocarbons, such as petroleum ether, hexane, heptane, cyclohexane, methylcyclohexane, benzene, toluene, xylene or decaline; chlorobenzene, dichlorobenzene, dichloromethane, chloroform, carbon tetrachloride, dichloroethane or trichloroethane; various ethers, such as diethyl ether, cyclopentyl methyl ether, diisopropyl ether, methyl t-butyl ether, methyl t-amyl ether, dioxane, tetrahydrofuran, 2-methyltetrahydrofuran, 1,2-dimethoxyethane, 1,2-diethoxyethane or anisole; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, sulfoxides, such as dimethyl sulfoxide, or sulfones, such as sulfolane.

When carrying out steps 1 to 5 of process P1 according to the invention, the reaction temperatures can be varied over a relatively wide range. In general, the steps are carried out at temperatures of 0° C. to 160° C., preferably at temperatures from 0° C. to 120° C.

As a means for controlling the temperature in process P1 according to the invention, it is also possible to use microwave technology.

Unless indicated otherwise, all steps of process P1 according to the invention are generally carried out under atmospheric pressure. However, it is also possible to operate under elevated or reduced pressure—in general between 0.1 and 10 bar.

For carrying out step 1 of process P1 according to the invention, in general an excess of oxidizing agent is employed of the aldehyde derivative of the formula (IIa). However, it is also possible to employ the components in other ratios.

For carrying out steps 2 and 5 of process P1 according to the invention, in general an excess of acid halide former is employed of the carboxylic acid derivative of the formula (IIb) or (IIe). However, it is also possible to employ the components in other ratios.

For carrying out step 3 of process P1 according to the invention, in general an excess of fluorinating agent is employed of the acid halide derivative of the formula (IIc). However, it is also possible to employ the components in other ratios.

For carrying out step 4 of process P1 according to the invention, in general an excess of acid or base is employed of the acid fluoride derivative of the formula (IId). However, it is also possible to employ the components in other ratios.

A further aspect of the invention comprises the process P2 according to the invention for synthesizing 1-methyl-3-dihalogenomethyl-5-halogenopyrazolethiocarboxamideso of the formula (I) wherein T represents an sulfur atom, as shown in the reaction scheme below:

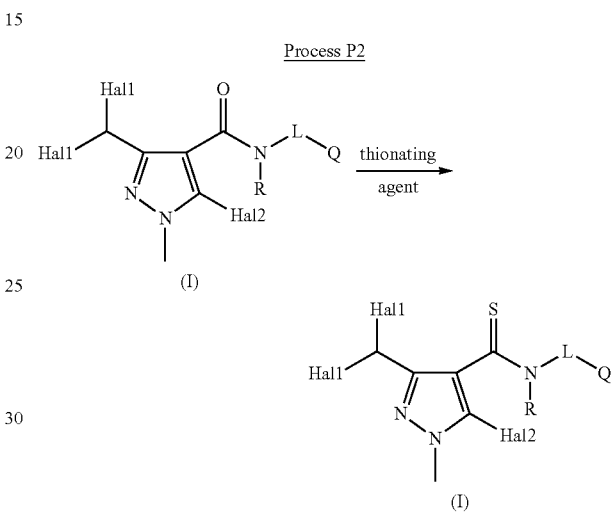

wherein Hal1, Hal2, R, L and Q are as herein-defined, in the optionally presence of a catalytic or stoichiometric or excess amount, quantity of a base such as an inorganic and organic base. Preference is given to using alkali metal carbonates, such as sodium carbonate, potassium carbonate, potassium bicarbonate, sodium bicarbonate; heterocyclic aromatic bases, such as pyridine, picoline, lutidine, collidine; and also tertiary amines, such as trimethylamine, triethylamine, tributylamine, N,N-dimethylaniline, N,N-dimethylaminopyridine or N-methyl-piperidine.

Process P2 according to the invention is performed in the presence of a thionating agent.

Starting amide derivatives of formula (I) can be prepared as previously described.

Suitable thionating agents for carrying out process P2 according to the invention can be sulfur (S), sulfhydric acid ($H_2S$), sodium sulfide ($Na_2S$), sodium hydrosulfide (NaHS), boron trisulfide ($B_2S_3$), bis(diethylaluminium) sulfide (($AlEt_2)_2S$), ammonium sulfide (($NH_4)_2S$), phosphorous pentasulfide ($P_2S_5$), Lawesson's reagent (2,4-bis(4-methoxyphenyl)-1,2,3,4-dithiadiphosphetane 2,4-disulfide) or a polymer-supported thionating reagent such as described in Journal of the Chemical Society, Perkin 1 (2001), 358.

The compounds according to the invention can be synthesized according to the process described above. Based on his expert knowledge, the person skilled in the art is able to modify the preparation processes for the compounds according to the invention in a suitable manner.

Certain amines of the formula (III)

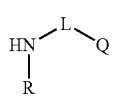

are already known:

| Amine of the formula (III) | Starting material for Example No. | can be prepared according to |
| --- | --- | --- |
| 2-(3-methylbutyl)aniline | 10 | EP-A 824099 |
| 2-(4-methylpentan-2-yl)aniline | 11, 12 | WO-A 2009/029383 |
| 2-(3,3-dimethylbutyl)aniline | 13, 14 | WO-A 2008/006576 |
| 2-(5-methylhexan-3-yl)aniline | 20 | WO-A 2002/038542 |
| 2-(4,4-dimethylpentan-2-yl)aniline | 21, 22 | WO-A 2005/042494 |
| 2-[2-(trimethylsilyl)ethyl]aniline | 24, 25 | WO-A 2005/049624 |
| 2-(1,1,2,3,3,3-hexafluoro-propoxy)aniline | 31, 32 | WO-A 2007/017450 |
| 2-[1,1'-bi(cyclopropyl)-2-yl] aniline | 46, 47, 48, 49, 50 | WO-A 2006/087223 |
| 2-(bicyclo[2.2.1]hept-2-yl)aniline | 51 | EP 96-116044 |
| 1,1,3-trimethylindane-4-amine | 64, 65 | JP 62096472; EP-A 654464 |
| 9-isopropyl-1,2,3,4-tetrahydro-1,4-methanonaphthalene-5-amine | 66, 67, 68 | WO-A 2007/068417 |
| 9-(dichloromethylene)-1,2,3,4-tetrahydro-1,4-methano naphthalen-5-amine | 71,72 | WO-A 2010/049228 |
| 4'-chloro-5-fluorobiphenyl-2-amine | 83, 84 | WO-A 2008/014905 |
| 4'-chloro-3',5-difluorobiphenyl-2-amine | 98 | DE-A 102005009458 |
| 4'-chloro-3'-fluorobiphenyl-2-amine | 99, 100, 101 | WO-A 2003/066609 |
| 3',4',5'-trifluorobiphenyl-2-amine | 104, 105, 106 | WO-A 2006/087343 |
| 3',4'-dichloro-5-fluorobiphenyl-2-amine | 116, 117 | DE-A 102004041531 |
| 4'-bromobiphenyl-2-amine | 139, 140, 141 | WO-A 2005040110 |
| 3'-fluoro-4'-(trifluoromethyl)biphenyl-2-amine | 148, 149 | WO-A 2003/066609 |
| 4'-bromo-3'-chlorobiphenyl-2-amine | 152, 153 | WO-A 2003/066609 |
| 3-isopropoxyaniline | 169, 170, 171 | DE-A 2434430 |

The compound according to the present invention can be prepared according to the general processes of preparation described above. It will nevertheless be understood that, on the basis of his general knowledge and of available publications, the skilled worker will be able to adapt this method according to the specifics of each of the compounds, which it is desired to synthesize.

In a further aspect, the present invention also relates to a fungicide composition comprising an effective and non-phytotoxic amount of an active compound of formula (I).

The expression "effective and non-phytotoxic amount" means an amount of composition according to the invention that is sufficient to control or destroy the fungi present or liable to appear on the cropsand that does not entail any appreciable symptom of phytotoxicity for the said crops. Such an amount can vary within a wide range depending on the fungus to be controlled, the type of crop, the climatic conditions and the compounds included in the fungicide composition according to the invention. This amount can be determined by systematic field trials that are within the capabilities of a person skilled in the art.

Thus, according to the invention, there is provided a fungicide composition comprising, as an active ingredient, an effective amount of a compound of formula (I) as herein defined and an agriculturally acceptable support, carrier or filler.

According to the invention, the term "support" denotes a natural or synthetic, organic or inorganic compound with that the active compound of formula (I) is combined or associated to make it easier to apply, notably to the parts of the plant. This support is thus generally inert and should be agriculturally acceptable. The support can be a solid or a liquid. Examples of suitable supports include clays, natural or synthetic silicates, silica, resins, waxes, solid fertilisers, water, alcohols, in particular butanol, organic solvents, mineral and plant oils and derivatives thereof. Mixtures of such supports can also be used.

The composition according to the invention can also comprise additional components. In particular, the composition can further comprise a surfactant. The surfactant can be an emulsifier, a dispersing agent or a wetting agent of ionic or non-ionic type or a mixture of such surfactants. Mention can be made, for example, of polyacrylic acid salts, lignosulfonic acid salts, phenolsulfonic or naphthalenesulfonic acid salts, polycondensates of ethylene oxide with fatty alcohols or with fatty acids or with fatty amines, substituted phenols (in particular alkylphenols or arylphenols), salts of sulfosuccinic acid esters, taurine derivatives (in particular alkyl taurates), phosphoric esters of polyoxyethylated alcohols or phenols, fatty acid esters of polyolsand derivatives of the above compounds containing sulfate, sulfonate and phosphate functions. The presence of at least one surfactant is generally essential when the active compound and/or the inert support are water-insoluble and when the vector agent for the application is water. Preferably, surfactant content can be comprised from 5% to 40% by weight of the composition.

Optionally, additional components can also be included, e.g. protective colloids, adhesives, thickeners, thixotropic agents, penetration agents, stabilisers, sequestering agents. More generally, the active compounds can be combined with any solid or liquid additive, that complies with the usual formulation techniques.

In general, the composition according to the invention can contain from 0.05 to 99% by weight of active compound, preferably 10 to 70% by weight.

Compositions according to the invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ULV) liquid, ultra low volume (ULV) suspension, water dispersible granules or tablets, water dispersible powder for slurry treatment, water soluble granules or tablets, water soluble powder for seed treatment and wettable powder. These compositions include not only compositions that are ready to be applied to the plant or seed to be treated by means of a suitable device, such as a spraying or dusting device, but also concentrated commercial compositions that must be diluted before application to the crop.

The compounds according to the invention can also be mixed with one or more insecticide, fungicide, bactericide, attractant, acaricide or pheromone active substance or other compounds with biological activity. The mixtures thus obtained have normally a broadened spectrum of activity. The mixtures with other fungicide compounds are particularly advantageous.

Examples of suitable fungicide mixing partners can be selected in the following lists:

(1) Inhibitors of the ergosterol biosynthesis, for example (1.1) aldimorph (1704-28-5), (1.2) azaconazole (60207-31-0), (1.3) bitertanol (55179-31-2), (1.4) bromuconazole (116255-48-2), (1.5) cyproconazole (113096-99-4), (1.6) diclobutrazole (75736-33-3), (1.7) difenoconazole (119446-68-3), (1.8) diniconazole (83657-24-3), (1.9) diniconazole-M (83657-18-5), (1.10) dodemorph (1593-77-7), (1.11) dodemorph acetate (31717-87-0), (1.12) epoxiconazole (106325-08-0), (1.13) etaconazole (60207-93-4), (1.14) fenarimol (60168-88-9), (1.15) fenbuconazole (114369-43-6), (1.16) fenhexamid (126833-17-8), (1.17) fenpropidin (67306-00-7), (1.18) fenpropimorph (67306-03-0), (1.19) fluquinconazole (136426-54-5), (1.20) flurprimidol (56425-91-3), (1.21) flusilazole (85509-19-9), (1.22) flutriafol (76674-21-0), (1.23) furconazole (112839-33-5), (1.24) furconazole-cis (112839-32-4), (1.25) hexaconazole (79983-71-4), (1.26) imazalil (60534-80-7), (1.27) imazalil sulfate (58594-72-2), (1.28) imibenconazole (86598-92-7), (1.29) ipconazole (125225-28-7), (1.30) metconazole (125116-23-6), (1.31) myclobutanil (88671-89-0), (1.32) naftifine (65472-88-0), (1.33) nuarimol (63284-71-9), (1.34) oxpoconazole (174212-12-5), (1.35) paclobutrazol (76738-62-0), (1.36) pefurazoate (101903-30-4), (1.37) penconazole (66246-88-6), (1.38) piperalin (3478-94-2), (1.39) prochloraz (67747-09-5), (1.40) propiconazole (60207-90-1), (1.41) prothioconazole (178928-70-6), (1.42) pyributicarb (88678-67-5), (1.43) pyrifenox (88283-41-4), (1.44) quinconazole (103970-75-8), (1.45) simeconazole (149508-90-7), (1.46) spiroxamine (118134-30-8), (1.47) tebuconazole (107534-96-3), (1.48) terbinafine (91161-71-6), (1.49) tetraconazole (112281-77-3), (1.50) triadimefon (43121-43-3), (1.51) triadimenol (89482-17-7), (1.52) tridemorph (81412-43-3), (1.53) triflumizole (68694-11-1), (1.54) triforine (26644-46-2), (1.55) triticonazole (131983-72-7), (1.56) uniconazole (83657-22-1), (1.57) uniconazole-p (83657-17-4), (1.58) viniconazole (77174-66-4), (1.59) voriconazole (137234-62-9), (1.60) 1-(4-chlorophenyl)-2-(1H-1,2,4-triazol-1-yl)cycloheptanol (129586-32-9), (1.61) methyl 1-(2,2-dimethyl-2,3-dihydro-1H-inden-1-yl)-1H-imidazole-5-carboxylate (110323-95-0), (1.62) N'-{5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy]phenyl}imidoformamide and (1.64) O-[1-(4-methoxyphenoxy)-3,3-dimethylbutan-2-yl] 1H-imidazole-1-carbothioate (111226-71-2).

(2) inhibitors of the respiratory chain at complex I or II, for example (2.1) bixafen (581809-46-3), (2.2) boscalid (188425-85-6), (2.3) carboxin (5234-68-4), (2.4) diflumetorim (130339-07-0), (2.5) fenfuram (24691-80-3), (2.6) fluopyram (658066-35-4), (2.7) flutolanil (66332-96-5), (2.8) fluxapyroxad (907204-31-3), (2.9) furametpyr (123572-88-3), (2.10) furmecyclox (60568-05-0), (2.11) isopyrazam (mixture of syn-epimeric racemate 1RS,4SR,9RS and anti-epimeric racemate 1RS,4SR,9SR) (881685-58-1), (2.12) isopyrazam (anti-epimeric racemate 1RS,4SR,9SR), (2.13) isopyrazam (anti-epimeric enantiomer 1R,4S,9S), (2.14) isopyrazam (anti-epimeric enantiomer 1S,4R,9R), (2.15) isopyrazam (syn epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil (55814-41-0), (2.19) oxycarboxin (5259-88-1), (2.20) penflufen (494793-67-8), (2.21) penthiopyrad (183675-82-3), (2.22) sedaxane (874967-67-6), (2.23) thifluzamide (130000-40-7), (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide (1092400-95-7) (WO 2008148570), (2.28) 5,8-difluoro-N-[2-(2-fluoro-4-{[4-(trifluoromethyl)pyridin-2-yl]oxy}phenyl)ethyl]quinazolin-4-amine (1210070-84-0) (WO2010025451), (2.29) N-[9-(dichloromethylene)-1,2,3,4-tetrahydro-1,4-methanonaphthalen-5-yl]-3-(difluoromethyl)-1-methyl-1H-pyrazole-4-carboxamide, (2.30) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide and (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide.

(3) inhibitors of the respiratory chain at complex III, for example (3.1) ametoctradin (865318-97-4), (3.2) amisulbrom (348635-87-0), (3.3) azoxystrobin (131860-33-8), (3.4) cyazofamid (120116-88-3), (3.5) coumethoxystrobin (850881-30-0), (3.6) coumoxystrobin (850881-70-8), (3.7) dimoxystrobin (141600-52-4), (3.8) enestroburin (238410-11-2) (WO 2004/058723), (3.9) famoxadone (131807-57-3) (WO 2004/058723), (3.10) fenamidone (161326-34-7) (WO 2004/058723), (3.11) fenoxystrobin (918162-02-4), (3.12) fluoxastrobin (361377-29-9) (WO 2004/058723), (3.13) kresoxim-methyl (143390-89-0) (WO 2004/058723), (3.14) metominostrobin (133408-50-1) (WO 2004/058723), (3.15) orysastrobin (189892-69-1) (WO 2004/058723), (3.16) picoxystrobin (117428-22-5) (WO 2004/058723), (3.17) pyraclostrobin (175013-18-0) (WO 2004/058723), (3.18) pyrametostrobin (915410-70-7) (WO 2004/058723), (3.19) pyraoxystrobin (862588-11-2) (WO 2004/058723), (3.20) pyribencarb (799247-52-2) (WO 2004/058723), (3.21) triclopyricarb (902760-40-1), (3.22) trifloxystrobin (141517-21-7) (WO 2004/058723), (3.23) (2E)-2-(2-{[6-(3-chloro-2-methylphenoxy)-5-fluoropyrimidin-4-yl]oxy}phenyl)-2-(methoxyimino)-N-methylethanamide (WO 2004/058723), (3.24) (2E)-2-(methoxyimino)-N-methyl-2-(2-{[({(1E)-1-[3-(trifluoromethyl)phenyl]ethylidene}amino)oxy] methyl}phenyl)ethanamide (WO 2004/058723), (3.25) (2E)-2-(methoxyimino)-N-methyl-2-{2-[(E)-({1-[3-(trifluoromethyl)phenyl]ethoxy}imino)methyl]

phenyl}ethanamide (158169-73-4), (3.26) (2E)-2-[({[(1E)-1-(3-{[(E)-1-fluoro-2-phenylethenyl]oxy}phenyl)ethylidene]amino}oxy)methyl]phenyl}-2-(methoxyimino)-N-methylethanamide (326896-28-0), (3.27) (2E)-2-{2-[4-({[(2E,3E)-4-(2,6-dichlorophenyl)but-3-en-2-ylidene]amino}oxy)methyl]phenyl}-2-(methoxyimino)-N-methylethanamide, (3.28) 2-chloro-N-(1,1,3-trimethyl-2,3-dihydro-1H-inden-4-yl)pyridine-3-carboxamide (119899-14-8), (3.29) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (3.30) methyl (2E)-2-{2-[({cyclopropyl[(4-methoxyphenyl)imino]methyl}sulfanyl)methyl]phenyl}-3-methoxyprop-2-enoate (149601-03-6), (3.31) N-(3-ethyl-3,5,5-trimethylcyclohexyl)-3-(formylamino)-2-hydroxybenzamide (226551-21-9), (3.32) 2-{2-[(2,5-dimethylphenoxy)methyl]phenyl}-2-methoxy-N-methylacetamide (173662-97-0) and (3.33) (2R)-2-{2-[(2,5-dimethylphenoxy)methyl]phenyl}-2-methoxy-N-methylacetamide (394657-24-0).

(4) Inhibitors of the mitosis and cell division, for example (4.1) benomyl (17804-35-2), (4.2) carbendazim (10605-21-7), (4.3) chlorfenazole (3574-96-7), (4.4) diethofencarb (87130-20-9), (4.5) ethaboxam (162650-77-3), (4.6) fluopicolide (239110-15-7), (4.7) fuberidazole (3878-19-1), (4.8) pencycuron (66063-05-6), (4.9) thiabendazole (148-79-8), (4.10) thiophanate-methyl (23564-05-8), (4.11) thiophanate (23564-06-9), (4.12) zoxamide (156052-68-5), (4.13) 5-chloro-7-(4-methylpiperidin-1-yl)-6-(2,4,6-trifluorophenyl)[1,2,4]triazolo[1,5-a]pyrimidine (214706-53-3) and (4.14) 3-chloro-5-(6-chloropyridin-3-yl)-6-methyl-4-(2,4,6-trifluorophenyl)pyridazine (1002756-87-7).

(5) Compounds capable to have a multisite action, like for example (5.1) bordeaux mixture (8011-63-0), (5.2) captafol (2425-06-1), (5.3) captan (133-06-2) (WO 02/12172), (5.4) chlorothalonil (1897-45-6), (5.5) copper hydroxide (20427-59-2), (5.6) copper naphthenate (1338-02-9), (5.7) copper oxide (1317-39-1), (5.8) copper oxychloride (1332-40-7), (5.9) copper(2+) sulfate (7758-98-7), (5.10) dichlofluanid (1085-98-9), (5.11) dithianon (3347-22-6), (5.12) dodine (2439-10-3), (5.13) dodine free base, (5.14) ferbam (14484-64-1), (5.15) fluorofolpet (719-96-0), (5.16) folpet (133-07-3), (5.17) guazatine (108173-90-6), (5.18) guazatine acetate, (5.19) iminoctadine (13516-27-3), (5.20) iminoctadine albesilate (169202-06-6), (5.21) iminoctadine triacetate (57520-17-9), (5.22) mancopper (53988-93-5), (5.23) mancozeb (8018-01-7), (5.24) maneb (12427-38-2), (5.25) metiram (9006-42-2), (5.26) metiram zinc (9006-42-2), (5.27) oxine-copper (10380-28-6), (5.28) propamidine (104-32-5), (5.29) propineb (12071-83-9), (5.30) sulfur and sulfur preparations including calcium polysulfide (7704-34-9), (5.31) thiram (137-26-8), (5.32) tolylfluanid (731-27-1), (5.33) zineb (12122-67-7) and (5.34) ziram (137-30-4).

(6) Compounds capable to induce a host defence, for example (6.1) acibenzolar-S-methyl (135158-54-2), (6.2) isotianil (224049-04-1), (6.3) probenazole (27605-76-1) and (6.4) tiadinil (223580-51-6).

(7) Inhibitors of the amino acid and/or protein biosynthesis, for example (7.1) andoprim (23951-85-1), (7.2) blasticidin-S (2079-00-7), (7.3) cyprodinil (121552-61-2), (7.4) kasugamycin (6980-18-3), (7.5) kasugamycin hydrochloride hydrate (19408-46-9), (7.6) mepanipyrim (110235-47-7), (7.7) pyrimethanil (53112-28-0) and (7.8) 3-(5-fluoro-3,3,4,4-tetramethyl-3,4-dihydroisoquinolin-1-yl)quinoline (861647-32-7) (WO2005070917).

(8) Inhibitors of the ATP production, for example (8.1) fentin acetate (900-95-8), (8.2) fentin chloride (639-58-7), (8.3) fentin hydroxide (76-87-9) and (8.4) silthiofam (175217-20-6).

(9) Inhibitors of the cell wall synthesis, for example (9.1) benthiavalicarb (177406-68-7), (9.2) dimethomorph (110488-70-5), (9.3) flumorph (211867-47-9), (9.4) iprovalicarb (140923-17-7), (9.5) mandipropamid (374726-62-2), (9.6) polyoxins (11113-80-7), (9.7) polyoxorim (22976-86-9), (9.8) validamycin A (37248-47-8) and (9.9) valifenalate (283159-94-4; 283159-90-0).

(10) Inhibitors of the lipid and membrane synthesis, for example (10.1) biphenyl (92-52-4), (10.2) chloroneb (2675-77-6), (10.3) dicloran (99-30-9), (10.4) edifenphos (17109-49-8), (10.5) etridiazole (2593-15-9), (10.6) iodocarb (55406-53-6), (10.7) iprobenfos (26087-47-8), (10.8) isoprothiolane (50512-35-1), (10.9) propamocarb (25606-41-1), (10.10) propamocarb hydrochloride (25606-41-1), (10.11) prothiocarb (19622-08-3), (10.12) pyrazophos (13457-18-6), (10.13) quintozene (82-68-8), (10.14) tecnazene (117-18-0) and (10.15) tolclofos-methyl (57018-04-9).

(11) Inhibitors of the melanine biosynthesis, for example (11.1) carpropamid (104030-54-8), (11.2) diclocymet (139920-32-4), (11.3) fenoxanil (115852-48-7), (11.4) phthalide (27355-22-2), (11.5) pyroquilon (57369-32-1), (11.6) tricyclazole (41814-78-2) and (11.7) 2,2,2-trifluoroethyl {3-methyl-1-[(4-methylbenzoyl)amino]butan-2-yl}carbamate (851524-22-6) (WO2005042474).

(12) Inhibitors of the nucleic acid synthesis, for example (12.1) benalaxyl (71626-11-4), (12.2) benalaxyl-M (kiralaxyl) (98243-83-5), (12.3) bupirimate (41483-43-6), (12.4) clozylacon (67932-85-8), (12.5) dimethirimol (5221-53-4), (12.6) ethirimol (23947-60-6), (12.7) furalaxyl (57646-30-7), (12.8) hymexazol (10004-44-1), (12.9) metalaxyl (57837-19-1), (12.10) metalaxyl-M (mefenoxam) (70630-17-0), (12.11) ofurace (58810-48-3), (12.12) oxadixyl (77732-09-3) and (12.13) oxolinic acid (14698-29-4).

(13) Inhibitors of the signal transduction, for example (13.1) chlozolinate (84332-86-5), (13.2) fenpiclonil (74738-17-3), (13.3) fludioxonil (131341-86-1), (13.4) iprodione (36734-19-7), (13.5) procymidone (32809-16-8), (13.6) quinoxyfen (124495-18-7) and (13.7) vinclozolin (50471-44-8).

(14) Compounds capable to act as an uncoupler, for example (14.1) binapacryl (485-31-4), (14.2) dinocap (131-72-6), (14.3) ferimzone (89269-64-7), (14.4) fluazinam (79622-59-6) and (14.5) meptyldinocap (131-72-6).

(15) Further compounds, for example (15.1) benthiazole (21564-17-0), (15.2) bethoxazin (163269-30-5), (15.3) capsimycin (70694-08-5), (15.4) carvone (99-49-0), (15.5) chinomethionat (2439-01-2), (15.6) pyriofenone (chlazafenone) (688046-61-9), (15.7) cufraneb (11096-18-7), (15.8) cyflufenamid (180409-60-3), (15.9) cymoxanil (57966-95-7), (15.10) cyprosulfamide (221667-31-8), (15.11) dazomet (533-74-4), (15.12) debacarb (62732-91-6), (15.13) dichlorophen (97-23-4), (15.14) diclomezine (62865-36-5), (15.15) difenzoquat (49866-87-7), (15.16) difenzoquat methylsulfate (43222-48-6), (15.17) diphenylamine (122-39-4), (15.18) ecomate, (15.19) fenpyrazamine (473798-59-3), (15.20) flumetover (154025-04-4), (15.21) fluoroimide (41205-21-4), (15.22) flusulfamide (106917-52-6), (15.23) flutianil (304900-25-2), (15.24) fosetyl-aluminium (39148-24-8), (15.25) fosetyl-calcium, (15.26) fosetyl-sodium (39148-16-8), (15.27) hexachlorobenzene (118-74-1), (15.28) irumamycin (81604-73-1), (15.29) methasulfocarb (66952-49-6), (15.30) methyl isothiocyanate (556-61-6), (15.31) metrafenone (220899-03-6), (15.32) mildiomycin (67527-71-3), (15.33) natamycin (7681-93-8), (15.34) nickel dimethyldithiocarbamate (15521-65-0), (15.35) nitrothal-isopropyl (10552-74-6), (15.36) octhilinone (26530-20-1), (15.37) oxamocarb (917242-12-7), (15.38) oxyfenthiin (34407-87-9), (15.39) pentachlorophenol and salts (87-86-5), (15.40) phenothrin, (15.41) phosphorous acid and its salts (13598-36-2), (15.42) propamocarb-fosetylate, (15.43) propanosine-sodium (88498-02-6), (15.44) proquinazid (189278-12-4), (15.45) pyrimorph (868390-90-3), (15.45e) (2E)-3-(4-tert-butylphenyl)-3-(2-chloropyridin-4-yl)-1-(morpholin-4-yl)prop-2-en-1-one (1231776-28-5), (15.45z) (2Z)-3-(4-tert-butylphenyl)-3-(2-chloropyridin-4-yl)-1-(morpholin-4-yl)prop-2-en-1-one (1231776-29-6), (15.46) pyrrolnitrine (1018-71-9) (EP-A 1 559 320), (15.47) tebufloquin (376645-78-2), (15.48) tecloftalam (76280-91-6), (15.49) tolnifanide (304911-98-6), (15.50) triazoxide (72459-58-6), (15.51) trichlamide (70193-21-4), (15.52) zarilamid (84527-51-5), (15.53) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate (517875-34-2) (WO2003035617), (15.54) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003319-79-6) (WO 2008013622), (15.55) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003319-80-9) (WO 2008013622), (15.56) 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003318-67-9) (WO 2008013622), (15.57) 1-(4-methoxyphenoxy)-3,3-dimethylbutan-2-yl 1H-imidazole-1-carboxylate (111227-17-9), (15.58) 2,3,5,6-tetrachloro-4-(methylsulfonyl)pyridine (13108-52-6), (15.59) 2,3-dibutyl-6-chlorothieno[2,3-d]pyrimidin-4(3H)-one (221451-58-7), (15.60) 2,6-dimethyl-1H,5H-[1,4]dithiino[2,3-c:5,6-c']dipyrrole-1,3,5,7(2H,6H)-tetrone, (15.61) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone (1003316-53-7) (WO 2008013622), (15.62) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone (1003316-54-8) (WO 2008013622), (15.63) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone (1003316-51-5) (WO 2008013622), (15.64) 2-butoxy-6-iodo-3-propyl-4H-chromen-4-one, (15.65) 2-chloro-5-[2-chloro-1-(2,6-difluoro-4-methoxyphenyl)-4-methyl-1H-imidazol-5-yl]pyridine, (15.66) 2-phenylphenol and salts (90-43-7), (15.67) 3-(4,4,5-trifluoro-3,3-dimethyl-3,4-dihydroisoquinolin-1-yl)quinoline (861647-85-0) (WO2005070917), (15.68) 3,4,5-trichloropyridine-2,6-dicarbonitrile (17824-85-0), (15.69) 3-[5-(4-chlorophenyl)-2,3-dimethyl-1,2-oxazolidin-3-yl]pyridine, (15.70) 3-chloro-5-(4-chlorophenyl)-4-(2,6-difluorophenyl)-6-methylpyridazine, (15.71) 4-(4-chlorophenyl)-5-(2,6-difluorophenyl)-3,6-dimethylpyridazine, (15.72) 5-amino-1,3,4-thiadiazole-2-thiol, (15.73) 5-chloro-N'-phenyl-N'-(prop-2-yn-1-yl)thiophene-2-sulfonohydrazide (134-31-6), (15.74) 5-fluoro-2-[(4-fluorobenzyl)oxy]pyrimidin-4-amine (1174376-11-4) (WO2009094442), (15.75) 5-fluoro-2-[(4-methylbenzyl)oxy]pyrimidin-4-amine (1174376-25-0) (WO2009094442), (15.76) 5-methyl-6-octyl[1,2,4]triazolo[1,5-a]pyrimidin-7-amine, (15.77) ethyl (2Z)-3-amino-2-cyano-3-phenylprop-2-enoate, (15.78) N'-(4-{[3-(4-chlorobenzyl)-1,2,4-thiadiazol-5-yl]oxy}-2,5-dimethylphenyl)-N-ethyl-N-methylimidoformamide, (15.79) N-(4-chlorobenzyl)-3-[3-methoxy-4-(prop-2-yn-1-yloxy)phenyl]propanamide, (15.80) N-[(4-chlorophenyl)(cyano)methyl]-3-[3-methoxy-4-(prop-2-yn-1-yloxy)phenyl]propanamide, (15.81) N-[(5-bromo-3-chloropyridin-2-yl)methyl]-2,4-dichloropyridine-3-carboxamide, (15.82) N-[1-(5-bromo-3-chloropyridin-2-yl)ethyl]-2,4-dichloropyridine-3-carboxamide, (15.83) N-[1-(5-bromo-3-chloropyridin-2-yl)ethyl]-2-fluoro-4-iodopyridine-3-carboxamide, (15.84) N-{(E)-[(cyclopropylmethoxy)imino][6-(difluoromethoxy)-2,3-difluorophenyl]methyl}-2-phenylacetamide (221201-92-9), (15.85) N-{(Z)-[(cyclopropylmethoxy)imino][6-(difluoromethoxy)-2,3-difluorophenyl]methyl}-2-phenylacetamide (221201-92-9), (15.86) N'-{4-[(3-tert-butyl-4-cyano-1,2-thiazol-5-yl)oxy]-2-chloro-5-methylphenyl}-N-ethyl-N-methylimidoformamide, (15.87) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide (922514-49-6) (WO 2007014290), (15.88) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide (922514-07-6) (WO 2007014290), (15.89) N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide (922514-48-5) (WO 2007014290), (15.90) pentyl {6-[({[(1-methyl-1H-tetrazol-5-yl)(phenyl)methylidene]amino}oxy)methyl]pyridin-2-yl}carbamate, (15.91) phenazine-1-carboxylic acid, (15.92) quinolin-8-ol (134-31-6), (15.93) quinolin-8-ol sulfate (2:1) (134-31-6) and (15.94) tert-butyl {6-[({[(1-methyl-1H-tetrazol-5-yl)(phenyl)methylene]amino}oxy)methyl]pyridin-2-yl}carbamate.

(16) Further compounds, for example (16.1) 1-methyl-3-(trifluoromethyl)-N-[2'-(trifluoromethyl)biphenyl-2-yl]-1H-pyrazole-4-carboxamide, (16.2) N-(4'-chlorobiphenyl-2-yl)-3-(difluoromethyl)-1-methyl-1H-pyrazole-4-carboxamide, (16.3) N-(2',4'-dichlorobiphenyl-2-yl)-3-(difluoromethyl)-1-methyl-1H-pyrazole-4-carboxamide, (16.4) 3-(difluoromethyl)-1-methyl-N-[4'-(trifluoromethyl)biphenyl-2-yl]-1H-pyrazole-4-carboxamide, (16.5) N-(2',5'-difluorobiphenyl-2-yl)-1-methyl-3-(trifluoromethyl)-1H-pyrazole-4-carboxamide, (16.6) 3-(difluoromethyl)-1-methyl-N-[4'-(prop-1-yn-1-yl)biphenyl-2-yl]-1H-pyrazole-4-carboxamide (known from WO 2004/058723), (16.7) 5-fluoro-1,3-dimethyl-N-[4'-(prop-1-yn-1-yl)biphenyl-2-yl]-1H-pyrazole-4-carboxamide (known from WO 2004/058723), (16.8) 2-chloro-N-[4'-(prop-1-yn-1-yl)biphenyl-2-yl]pyridine-3-carboxamide (known from WO 2004/058723), (16.9) 3-(difluoromethyl)-N-[4'-(3,3-dimethylbut-1-yn-1-yl)biphenyl-2-yl]-1-methyl-1H-pyrazole-4-carboxamide (known from WO 2004/058723), (16.10) N-[4'-(3,3-dimethylbut-1-yn-1-yl)biphenyl-2-yl]-5-fluoro-1,3-dimethyl-1H-pyrazole-4-carboxamide (known from WO 2004/058723), (16.11) 3-(difluoromethyl)-N-(4'-ethynylbiphenyl-2-yl)-1-methyl-1H-pyrazole-4-carboxamide (known from WO 2004/058723), (16.12) N-(4'-ethynylbiphenyl-2-yl)-5-fluoro-1,3-dimethyl-1H-pyrazole-4-carboxamide (known from WO 2004/058723), (16.13) 2-chloro-N-(4'-ethynylbiphenyl-2-yl)pyridine-3-carboxamide (known from WO 2004/058723), (16.14) 2-chloro-N-[4'-(3,3-dimethylbut-1-yn-1-yl)biphenyl-2-yl]pyridine-3-carboxamide (known from WO 2004/058723), (16.15) 4-(difluoromethyl)-2-methyl-N-[4'-(trifluoromethyl)biphenyl-2-yl]-1,3-thiazole-5-carboxamide (known from WO 2004/058723), (16.16) 5-fluoro-N-[4'-(3-hydroxy-3-methylbut-1-yn-1-yl)biphenyl-2-yl]-1,3-dimethyl-1H-pyrazole-4-carboxamide (known from WO 2004/058723), (16.17) 2-chloro-N-[4'-(3-hydroxy-3-methylbut-1- yn-1-yl)biphenyl-2-yl]pyridine-3-carboxamide (known from WO 2004/058723), (16.18) 3-(difluoromethyl)-N-[4'-(3-methoxy-3-methylbut-1-yn-1-yl)biphenyl-2-yl]-1-methyl-1H-pyrazole-4-carboxamide (known from WO 2004/058723), (16.19) 5-fluoro-N-[4'-(3-methoxy-3-methylbut-1-yn-1-yl)biphenyl-2-yl]-1,3-dimethyl-1H-pyrazole-4-carboxamide (known from WO 2004/058723), (16.20) 2-chloro-N-[4'-(3-methoxy-3-methylbut-1-yn-1-yl)biphenyl-2-yl]pyridine-3-carboxamide (known from WO 2004/058723), (16.21) (5-bromo-2-methoxy-4-methylpyridin-3-yl)(2,3,4-trimethoxy-6-methylphenyl)methanone (known from EP-A 1 559 320), (16.22) N-[2-(4-{[3-(4-chlorophenyl)prop-2-yn-1-yl]oxy}-3-methoxyphenyl)ethyl]-N2-(methylsulfonyl)valinamide (220706-93-4), (16.23) 4-oxo-4-[(2-phenylethyl)amino]butanoic acid and (16.24) but-3-yn-1-yl {6-[({[(Z)-(1-methyl-1H-tetrazol-5-yl)(phenyl)methylene]amino}oxy)methyl]pyridin-2-yl}carbamate.

All named mixing partners of the classes (1) to (16) can, if their functional groups enable this, optionally form salts with suitable bases or acids.

The composition according to the invention comprising a mixture of a compound of formula (I) with a bactericide compound can also be particularly advantageous. Examples of suitable bactericide mixing partners can be selected in the following list: bronopol, dichlorophen, nitrapyrin, nickel dimethyldithiocarbamate, kasugamycin, octhilinone, furancarboxylic acid, oxytetracycline, probenazole, streptomycin, tecloftalam, copper sulfate and other copper preparations.

The compounds of formula (I) and the fungicide composition according to the invention can be used to curatively or preventively control the phytopathogenic fungi of plants or crops.

Thus, according to a further aspect of the invention, there is provided a method for curatively or preventively controlling the phytopathogenic fungi of plants or crops characterised in that a compound of formula (I) or a fungicide composition according to the invention is applied to the seed, the plant or to the fruit of the plant or to the soil wherein the plant is growing or wherein it is desired to grow.

The method of treatment according to the invention can also be useful to treat propagation material such as tubers or rhizomes, but also seeds, seedlings or seedlings pricking out and plants or plants pricking out. This method of treatment can also be useful to treat roots. The method of treatment according to the invention can also be useful to treat the overground parts of the plant such as trunks, stems or stalks, leaves, flowers and fruit of the concerned plant.

According to the invention all plants and plant parts can be treated. By plants is meant all plants and plant populations such as desirable and undesirable wild plants, cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods. By plant parts is meant all above ground and below ground parts and organs of plants such as shoot, leaf, blossom and root, whereby for example leaves, needles, stems, branches, blossoms, fruiting bodies, fruits and seed as well as roots, corms and rhizomes are listed. Crops and vegetative and generative propagating material, for example cuttings, corms, rhizomes, runners and seeds also belong to plant parts.

Among the plants that can be protected by the method according to the invention, mention may be made of major field crops like corn, soybean, cotton, *Brassica* oilseeds such as *Brassica napus* (e.g. canola), *Brassica rapa*, *B. juncea* (e.g. mustard) and *Brassica carinata*, rice, wheat, sugarbeet, sugarcane, oats, rye, barley, millet, triticale, flax, vine and various fruits and vegetables of various botanical taxa such as *Rosaceae* sp. (for instance pip fruit such as apples and pears, but also stone fruit such as apricots, cherries, almonds and peaches, berry fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for instance banana trees and plantings), *Rubiaceae* sp. (for instance coffee), *Theaceae* sp., *Sterculiceae* sp., *Rutaceae* sp. (for instance lemons, oranges and grapefruit); *Solanaceae* sp. (for instance tomatoes, potatoes, peppers, eggplant), *Liliaceae* sp., *Compositiae* sp. (for instance lettuce, artichoke and chicory—including root chicory, endive or common chicory), *Umbelliferae* sp. (for instance carrot, parsley, celery and celeriac), *Cucurbitaceae* sp. (for instance cucumber—including pickling cucumber, squash, watermelon, gourds and melons), *Alliaceae* sp. (for instance onions and leek), *Cruciferae* sp. (for instance white cabbage, red cabbage, broccoli, cauliflower, brussel sprouts, pak Choi, kohlrabi, radish, horseradish, cress, Chinese cabbage), *Leguminosae* sp. (for instance peanuts, peas and beans beans—such as climbing beans and broad beans), *Chenopodiaceae* sp. (for instance mangold, spinach beet, spinach, beetroots), *Malvaceae* (for instance okra), *Asparagaceae* (for instance asparagus); horticultural and forest crops; ornamental plants; as well as genetically modified homologues of these crops.

The method of treatment according to the invention can be used in the treatment of genetically modified organisms (GMOs), e.g. plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology or RNA interference—RNAi—technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in additional effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are also suitable for mobilizing the defense system of the plant against attack by unwanted microorganisms. This may, if appropriate, be one of the reasons of the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted microorganisms, the treated plants display a substantial degree of resistance to these microorganisms. In the present case, unwanted microorganisms are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Examples of nematode resistant plants are described in e.g. U.S. patent application Ser. Nos. 11/765,491, 11/765,494, 10/926,819, 10/782,020, 12/032,479, 10/783,417, 10/782,096, 11/657,964, 12/192,904, 11/396,808, 12/166,253, 12/166,239, 12/166,124, 12/166,209, 11/762,886, 12/364,335, 11/763,947, 12/252,453, 12/209,354, 12/491,396 or 12/497,221.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability. Examples of plants with the above-mentioned traits are non-exhaustively listed in Table A.

Plants that may be treated according to the invention are hybrid plants that already express the characteristic of heterosis or hybrid vigor which results in generally higher yield, vigor, health and resistance towards biotic and abiotic stresses). Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species (WO 92/05251, WO 95/09910, WO 98/27806, WO 05/002324, WO 06/021972 and U.S. Pat. No. 6,229,072). However, genetic determinants for male sterility can also be located in the nuclear genome. Male sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar (e.g. WO 91/02069).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-resistant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., 1983, Science 221, 370-371), the CP4 gene of the bacterium *Agrobacterium* sp. (Barry et al., 1992, Curr. Topics Plant Physiol. 7, 139-145), the genes encoding a Petunia EPSPS (Shah et al., 1986, Science 233, 478-481), a Tomato EPSPS (Gasser et al., 1988, J. Biol. Chem. 263, 4280-4289), or an *Eleusine* EPSPS (WO 01/66704). It can also be a mutated EPSPS as described in for example EP 0837944, WO 00/66746, WO 00/66747 or WO02/26995. Glyphosate-tolerant plants can also be obtained by expressing a gene that encodes a glyphosate oxido-reductase enzyme as described in U.S. Pat. Nos. 5,776,760 and 5,463,175. Glyphosate-tolerant plants can also be obtained by expressing a gene that encodes a glyphosate acetyl transferase enzyme as described in for example WO 02/36782, WO 03/092360, WO 05/012515 and WO 07/024,782. Glyphosate-tolerant plants can also be obtained by selecting plants containing naturally-occurring mutations of the above-mentioned genes, as described in for example WO 01/024615 or WO 03/013226. Plants expressing EPSPS genes that confer glyphosate tolerance are described in e.g. U.S. patent application Ser. Nos. 11/517,991, 10/739,610, 12/139,408, 12/352,532, 11/312, 866, 11/315,678, 12/421,292, 11/400,598, 11/651,752, 11/681,285, 11/605,824, 12/468,205, 11/760,570, 11/762, 526, 11/769,327, 11/769,255, 11/943,801 or 12/362,774. Plants comprising other genes that confer glyphosate tolerance, such as decarboxylase genes, are described in e.g. U.S. patent application Ser. Nos. 11/588,811, 11/185,342, 12/364, 724, 11/185,560 or 12/423,926.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition, e.g. described in U.S. patent application Ser. No. 11/760,602. One such efficient detoxifying enzyme is an enzyme encoding a phosphinothricin acetyltransferase (such as the bar or pat protein from *Streptomyces* species). Plants expressing an exogenous phosphinothricin acetyltransferase are for example described in U.S. Pat. Nos. 5,561,236; 5,648,477; 5,646,024; 5,273, 894; 5,637,489; 5,276,268; 5,739,082; 5,908,810 and 7,112, 665.

Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated or chimeric HPPD enzyme as described in WO 96/38567, WO 99/24585, WO 99/24586, WO 2009/144079, WO 2002/ 046387, or U.S. Pat. No. 6,768,044. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 99/34008 and WO 02/36787. Tolerance of plants to HPPD inhibitors can also be improved by transforming plants with a gene encoding an enzyme having prephenate deshydrogenase (PDH) activity in addition to a gene encoding an HPPD-tolerant enzyme, as described in WO 2004/ 024928. Further, plants can be made more tolerant to HPPD-inhibitor herbicides by adding into their genome a gene encoding an enzyme capable of metabolizing or degrading HPPD inhibitors, such as the CYP450 enzymes shown in WO 2007/103567 and WO 2008/150473.

Still further herbicide resistant plants are plants that are made tolerant to acetolactate synthase (ALS) inhibitors. Known ALS-inhibitors include, for example, sulfonylurea, imidazolinone, triazolopyrimidines, pryimidinyoxy(thio) benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright (2002, Weed Science 50:700-712), but also, in U.S. Pat. Nos. 5,605,011, 5,378,824, 5,141,870, and 5,013,659. The production of sulfonylurea-tolerant plants and imidazolinone-tolerant plants is described in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270. Other imidazolinone-tolerant plants are also described in for example WO 2004/040012, WO 2004/ 106529, WO 2005/020673, WO 2005/093093, WO 2006/ 007373, WO 2006/015376, WO 2006/024351, and WO 2006/ 060634. Further sulfonylurea- and imidazolinone-tolerant plants are also described in for example WO 07/024,782 and U.S. Patent Application No. 61/288,958.

Other plants tolerant to imidazolinone and/or sulfonylurea can be obtained by induced mutagenesis, selection in cell cultures in the presence of the herbicide or mutation breeding as described for example for soybeans in U.S. Pat. No. 5,084, 082, for rice in WO 97/41218, for sugar beet in U.S. Pat. No. 5,773,702 and WO 99/057965, for lettuce in U.S. Pat. No. 5,198,599, or for sunflower in WO 01/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed by Crickmore et al. (1998, Microbiology and Molecular Biology Reviews, 62: 807-813), updated by Crickmore et al. (2005) at the *Bacillus thuringiensis* toxin nomenclature, online at: http://www.lifesci.sussex.ac.uk/Home/Neil_Crickmore/Bt/), or insecticidal portions thereof, e.g., proteins of the Cry protein classes Cry1Ab, Cry1Ac, Cry1B, Cry1C, Cry1D, Cry1F, Cry2Ab, Cry3Aa, or Cry3Bb or insecticidal portions thereof (e.g. EP 1999141 and WO 2007/ 107302), or such proteins encoded by synthetic genes as e.g. described in and U.S. patent application Ser. No. 12/249,016; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins (Moellenbeck et al. 2001, Nat. Biotechnol. 19: 668-72; Schnepf et al. 2006, Applied Environm. Microbiol. 71, 1765-1774) or the binary toxin made up of the Cry1A or Cry1F proteins and the Cry2Aa or Cry2Ab or Cry2Ae proteins (U.S. patent application Ser. No. 12/214,022 and EP 08010791.5); or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON89034 (WO 2007/ 027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604; or 5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/home/ Neil_Crickmore/Bt/vip.html, e.g., proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 5) to 7) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102; or 9) a secreted protein from *Bacillus thuringiensis* or *Bacillus cereus* which is insecticidal in the presence of a crystal protein from *Bacillus thuringiensis*, such as the binary toxin made up of VIP3 and Cry1A or Cry1F (U.S. Patent Appl. No. 61/126,083 and 61/195,019), or the binary toxin made up of the VIP3 protein and the Cry2Aa or Cry2Ab or Cry2Ae proteins (U.S. patent application Ser. No. 12/214,022 and EP 08010791.5).

10) a protein of 9) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein)

Of course, an insect-resistant transgenic plant, as used herein, also includes any plant comprising a combination of genes encoding the proteins of any one of the above classes 1 to 10. In one embodiment, an insect-resistant plant contains more than one transgene encoding a protein of any one of the above classes 1 to 10, to expand the range of target insect species affected when using different proteins directed at different target insect species, or to delay insect resistance development to the plants by using different proteins insecticidal to the same target insect species but having a different mode of action, such as binding to different receptor binding sites in the insect.

An "insect-resistant transgenic plant", as used herein, further includes any plant containing at least one transgene comprising a sequence producing upon expression a double-stranded RNA which upon ingestion by a plant insect pest inhibits the growth of this insect pest, as described e.g. in WO 2007/080126, WO 2006/129204, WO 2007/074405, WO 2007/080127 and WO 2007/035650.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

1) plants which contain a transgene capable of reducing the expression and/or the activity of poly(ADP-ribose) polymerase (PARP) gene in the plant cells or plants as described in WO 00/04173, WO/2006/045633, EP 04077984.5, or EP 06009836.5.

2) plants which contain a stress tolerance enhancing transgene capable of reducing the expression and/or the activity of the PARG encoding genes of the plants or plants cells, as described e.g. in WO 2004/090140.

3) plants which contain a stress tolerance enhancing transgene coding for a plant-functional enzyme of the nicotineamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphorybosyltransferase as described e.g. in EP 04077624.7, WO 2006/133827, PCT/EP07/002,433, EP 1999263, or WO 2007/107326.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications. Said transgenic plants synthesizing a modified starch are disclosed, for example, in EP 0571427, WO 95/04826, EP 0719338, WO 96/15248, WO 96/19581, WO 96/27674, WO 97/11188, WO 97/26362, WO 97/32985, WO 97/42328, WO 97/44472, WO 97/45545, WO 98/27212, WO 98/40503, WO99/58688, WO 99/58690, WO 99/58654, WO 00/08184, WO 00/08185, WO 00/08175, WO 00/28052, WO 00/77229, WO 01/12782, WO 01/12826, WO 02/101059, WO 03/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 00/22140, WO 2006/063862, WO 2006/072603, WO 02/034923, EP 06090134.5, EP 06090228.5, EP 06090227.7, EP 07090007.1, EP 07090009.7, WO 01/14569, WO 02/79410, WO 03/33540, WO 2004/078983, WO 01/19975, WO 95/26407, WO 96/34968, WO 98/20145, WO 99/12950, WO 99/66050, WO 99/53072, U.S. Pat. No. 6,734,341, WO 00/11192, WO 98/22604, WO 98/32326, WO 01/98509, WO 01/98509, WO 2005/002359, U.S. Pat. No. 5,824,790, U.S. Pat. No. 6,013,861, WO 94/04693, WO 94/09144, WO 94/11520, WO 95/35026, WO 97/20936

2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, as disclosed in EP 0663956, WO 96/01904, WO 96/21023, WO 98/39460, and WO 99/24593, plants producing alpha-1,4-glucans as disclosed in WO 95/31553, US 2002031826, U.S. Pat. No. 6,284,479, U.S. Pat. No. 5,712,107, WO 97/47806, WO 97/47807, WO 97/47808 and WO 00/14249, plants producing alpha-1,6 branched alpha-1,4-glucans, as disclosed in WO 00/73422, plants producing alternan, as disclosed in e.g. WO 00/47727, WO 00/73422, EP 06077301.7, U.S. Pat. No. 5,908,975 and EP 0728213, 3) transgenic plants which produce hyaluronan, as for example disclosed in WO 2006/032538, WO 2007/

039314, WO 2007/039315, WO 2007/039316, JP 2006304779, and WO 2005/012529.

4) transgenic plants or hybrid plants, such as onions with characteristics such as 'high soluble solids content', 'low pungency' (LP) and/or 'long storage' (LS), as described in U.S. patent application Ser. No. 12/020,360 and 61/054,026.

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics and include:

a) Plants, such as cotton plants, containing an altered form of cellulose synthase genes as described in WO 98/00549
b) Plants, such as cotton plants, containing an altered form of rsw2 or rsw3 homologous nucleic acids as described in WO 2004/053219
c) Plants, such as cotton plants, with increased expression of sucrose phosphate synthase as described in WO 01/17333
d) Plants, such as cotton plants, with increased expression of sucrose synthase as described in WO 02/45485
e) Plants, such as cotton plants, wherein the timing of the plasmodesmatal gating at the basis of the fiber cell is altered, e.g. through downregulation of fiber-selective β-1,3-glucanase as described in WO 2005/017157, or as described in EP 08075514.3 or U.S. Patent Appl. No. 61/128,938
f) Plants, such as cotton plants, having fibers with altered reactivity, e.g. through the expression of N-acetylglucosaminetransferase gene including nodC and chitin synthase genes as described in WO 2006/136351

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants contain a mutation imparting such altered oil profile characteristics and include:

a) Plants, such as oilseed rape plants, producing oil having a high oleic acid content as described e.g. in U.S. Pat. No. 5,969,169, U.S. Pat. No. 5,840,946 or U.S. Pat. No. 6,323,392 or U.S. Pat. No. 6,063,947
b) Plants such as oilseed rape plants, producing oil having a low linolenic acid content as described in U.S. Pat. No. 6,270,828, U.S. Pat. No. 6,169,190, or U.S. Pat. No. 5,965,755
c) Plant such as oilseed rape plants, producing oil having a low level of saturated fatty acids as described e.g. in U.S. Pat. No. 5,434,283 or U.S. patent application Ser. No. 12/668,303

Plants or plant cultivars (that can be obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants contain a mutation imparting such altered seed shattering characteristics and include plants such as oilseed rape plants with delayed or reduced seed shattering as described in U.S. Patent Appl. No. 61/135,230 WO09/068,313 and WO10/006,732.

Particularly useful transgenic plants which may be treated according to the invention are plants containing transformation events, or combination of transformation events, that are the subject of petitions for non-regulated status, in the United States of America, to the Animal and Plant Health Inspection Service (APHIS) of the United States Department of Agriculture (USDA) whether such petitions are granted or are still pending. At any time this information is readily available from APHIS (4700 River Road Riverdale, Md. 20737, USA), for instance on its interne site (URL http://www.aphis.usda.gov/brs/not_reg.html). On the filing date of this application the petitions for nonregulated status that were pending with APHIS or granted by APHIS were those listed in table B which contains the following information:

Petition: the identification number of the petition. Technical descriptions of the transformation events can be found in the individual petition documents which are obtainable from APHIS, for example on the APHIS website, by reference to this petition number. These descriptions are herein incorporated by reference.
Extension of Petition: reference to a previous petition for which an extension is requested.
Institution: the name of the entity submitting the petition.
Regulated article: the plant species concerned.
Transgenic phenotype: the trait conferred to the plants by the transformation event.
Transformation event or line: the name of the event or events (sometimes also designated as lines or lines) for which nonregulated status is requested.
APHIS documents: various documents published by APHIS in relation to the Petition and which can be requested with APHIS.

Additional particularly useful plants containing single transformation events or combinations of transformation events are listed for example in the databases from various national or regional regulatory agencies (see for example http://gmoinfo.jrc.it/gmp_browse.aspx and http://www.agbios.com/dbase.php).

Further particularly transgenic plants include plants containing a transgene in an agronomically neutral or beneficial position as described in any of the patent publications listed in Table C.

TABLE A

| Trait | Reference | |
|---|---|---|
| Water use efficiency | WO 2000/073475 | |
| Nitrogen use efficiency | WO 1995/009911 | WO 2007/076115 |
| | WO 1997/030163 | WO 2005/103270 |
| | WO 2007/092704 | WO 2002/002776 |
| Improved photosynthesis | WO 2008/056915 | WO 2004/101751 |
| Nematode resistance | WO 1995/020669 | WO 2003/033651 |
| | WO 2001/051627 | WO 1999/060141 |
| | WO 2008/139334 | WO 1998/012335 |
| | WO 2008/095972 | WO 1996/030517 |
| | WO 2006/085966 | WO 1993/018170 |
| Reduced pod dehiscence | WO 2006/009649 | WO 1997/013865 |
| | WO 2004/113542 | WO 1996/030529 |
| | WO 1999/015680 | WO 1994/023043 |
| | WO 1999/000502 | |
| Aphid resistance | WO 2006/125065 | WO 2008/067043 |
| | WO 1997/046080 | WO 2004/072109 |
| Sclerotinia resistance | WO 2006/135717 | WO 2005/000007 |
| | WO 2006/055851 | WO 2002/099385 |
| | WO 2005/090578 | WO 2002/061043 |
| Botrytis resistance | WO 2006/046861 | WO 2002/085105 |
| Bremia resistance | US 20070022496 | WO 2004/049786 |
| | WO 2000/063432 | |
| Erwinia resistance | WO 2004/049786 | |
| Closterovirus resistance | WO 2007/073167 | WO 2002/022836 |
| | WO 2007/053015 | |
| Stress tolerance (including drought tolerance) | WO 2010/019838 | WO2008/002480 |
| | WO 2009/049110 | WO2005/033318 |
| Tobamovirus resistance | WO 2006/038794 | |

TABLE B

Petitions of Nonregulated Status Granted or Pending by APHIS as of Mar. 31, 2010

Applicant Documents

| Petition | Extension of Petition Number *** | Institution | Regulated Article | Transgenic Phenotype | Transformation Event or Line |
|---|---|---|---|---|---|
| Petitions for Nonregulated Status Pending ||||||
| 10-070-01p | | Virginia Tech | Peanut | Sclerotinia blight resistant | N70, P39, and W171 |
| 09-349-01p | | Dow AgroSciences | Soybean | Herbicide Tolerant | DAS-68416-4 |
| 09-328-01p | | Bayer Crop Science | Soybean | Herbicide Tolerant | FG72 |
| 09-233-01p | | Dow | Corn | Herbicide Tolerant | DAS-40278-9 |
| 09-201-01p | | Monsanto | Soybean | | MON-877Ø5-6 |
| 09-183-01p | | Monsanto | Soybean | | MON-87769 |
| 09-082-01p | | Monsanto | Soybean | Lepidopteran resistant | MON 87701 |
| 09-063-01p | | Stine Seed | Corn | Glyphosate tolerant | HCEM485 |
| 09-055-01p | | Monsanto | Corn | Drought Tolerant | MON 87460 |
| 09-015-01p | | BASF Plant Science, LLC | Soybean | Herbicide Tolerant | BPS-CV127-9 Soybean |
| 08-366-01p | | ArborGen | Eucalyptus | Freeze Tolerant, Fertility Altered | ARB-FTE1-08 |
| 08-340-01p | | Bayer | Cotton | Glufosinate Tolerant, Insect Resistant | T304-40XGHB119 |
| 08-338-01p | | Pioneer | Corn | Male Sterile, Fertility Restored, Visual Marker | DP-32138-1 |
| 08-315-01p | | Florigene | Rose | Altered Flower Color | IFD-524Ø1-4 and IFD-529Ø1-9 |
| 07-253-01p | | Syngenta | Corn | Lepidopteran resistant | MIR-162 Maize |
| 07-108-01p | | Syngenta | Cotton | Lepidopteran Resistant | COT67B |
| 06-354-01p | | Pioneer | Soybean | High Oleic Acid | DP-3Ø5423-1 |
| 05-280-01p | | Syngenta | Corn | Thermostable alpha-amylase | 3272 |
| 04-110-01p | | Monsanto & Forage Genetics | Alfalfa | Glyphosate Tolerant | J101, J163 |
| 03-104-01p | | Monsanto & Scotts | Creeping bentgrass | Glyphosate Tolerant | ASR368 |
| Petitions for Nonregulated Status Granted ||||||
| 07-152-01p | | Pioneer | Corn | glyphosate & Imidazolinone tolerant | DP-098140-6 |
| 04-337-01p | | University of Florida | Papaya | Papaya Ringspot Virus Resistant | X17-2 |
| 06-332-01p | | Bayer CropScience | Cotton | Glyphosate tolerant | GHB614 |
| 06-298-01p | | Monsanto | Corn | European Corn Borer resistant | MON 89034 |
| 06-271-01p | | Pioneer | Soybean | Glyphosate & acetolactate synthase tolerant | 356043 (DP-356Ø43-5) |
| 06-234-01p | 98-329-01p | Bayer CropScience | Rice | Phosphinothricin tolerant | LLRICE601 |
| 06-178-01p | | Monsanto | Soybean | Glyphosate tolerant | MON 89788 |
| 04-362-01p | | Syngenta | Corn | Corn Rootworm Protected | MIR604 |
| 04-264-01p | | ARS | Plum | Plum Pox Virus Resistant | C5 |
| 04-229-01p | | Monsanto | Corn | High Lysine | LY038 |
| 04-125-01p | | Monsanto | Corn | Corn Rootworm Resistant | 88017 |
| 04-086-01p | | Monsanto | Cotton | Glyphosate Tolerant | MON 88913 |
| 03-353-01p | | Dow | Corn | Corn Rootworm Resistant | 59122 |
| 03-323-01p | | Monsanto | Sugar Beet | Glyphosate Tolerant | H7-1 |
| 03-181-01p | 00-136-01p | Dow | Corn | Lepidopteran Resistant & Phosphinothricin tolerant | TC-6275 |
| 03-155-01p | | Syngenta | Cotton | Lepidopteran Resistant | COT 102 |
| 03-036-01p | | Mycogen/Dow | Cotton | Lepidopteran Resistant | 281-24-236 |
| 03-036-02p | | Mycogen/Dow | Cotton | Lepidopteran Resistant | 3006-210-23 |
| 02-042-01p | | Aventis | Cotton | Phosphinothericin tolerant | LLCotton25 |
| 01-324-01p | 98-216-01p | Monsanto | Rapeseed | Glyphosate tolerant | RT200 |

TABLE B-continued

Petitions of Nonregulated Status Granted or Pending by APHIS as of Mar. 31, 2010

Applicant Documents

| Petition | Extension of Petition Number *** | Institution | Regulated Article | Transgenic Phenotype | Transformation Event or Line |
|---|---|---|---|---|---|
| 01-206-01p | 98-278-01p | Aventis | Rapeseed | Phosphinothricin tolerant & pollination control | MS1 & RF1/RF2 |
| 01-206-02p | 97-205-01p | Aventis | Rapeseed | Phosphinothricin tolerant | Topas 19/2 |
| 01-137-01p | | Monsanto | Corn | Corn Rootworm Resistant | MON 863 |
| 01-121-01p | | Vector | Tobacco | Reduced nicotine | Vector 21-41 |
| 00-342-01p | | Monsanto | Cotton | Lepidopteran resistant | Cotton Event 15985 |
| 00-136-01p | | Mycogen c/o Dow & Pioneer | Corn | Lepidopteran resistant phosphinothricin tolerant | Line 1507 |
| 00-011-01p | 97-099-01p | Monsanto | Corn | Glyphosate tolerant | NK603 |
| 99-173-01p | 97-204-01p | Monsanto | Potato | PLRV & CPB resistant | RBMT22-82 |
| 98-349-01p | 95-228-01p | AgrEvo | Corn | Phosphinothricin tolerant and Male sterile | MS6 |
| 98-335-01p | | U. of Saskatchewan | Flax | Tolerant to soil residues of sulfonyl urea herbicide | CDC Triffid |
| 98-329-01p | | AgrEvo | Rice | Phosphinothricin tolerant | LLRICE06, LLRICE62 |
| 98-278-01p | | AgrEvo | Rapeseed | Phosphinothricin tolerant & Pollination control | MS8 & RF3 |
| 98-238-01p | | AgrEvo | Soybean | Phosphinothricin tolerant | GU262 |
| 98-216-01p | | Monsanto | Rapeseed | Glyphosate tolerant | RT73 |
| 98-173-01p | | Novartis Seeds & Monsanto | Beet | Glyphosate tolerant | GTSB77 |
| 98-014-01p | 96-068-01p | AgrEvo | Soybean | Phosphinothricin tolerant | A5547-127 |
| 97-342-01p | | Pioneer | Corn | Male sterile & Phosphinothricin tolerant | 676, 678, 680 |
| 97-339-01p | | Monsanto | Potato | CPB & PVY resistant | RBMT15-101, SEMT15-02, SEMT15-15 |
| 97-336-01p | | AgrEvo | Beet | Phosphinothricin tolerant | T-120-7 |
| 97-287-01p | | Monsanto | Tomato | Lepidopteran resistant | 5345 |
| 97-265-01p | | AgrEvo | Corn | Phosphinothricin tolerant & Lep. resistant | CBH-351 |
| 97-205-01p | | AgrEvo | Rapeseed | Phosphinothricin tolerant | T45 |
| 97-204-01p | | Monsanto | Potato | CPB & PLRV resistant | RBMT21-129 & RBMT21-350 |
| 97-148-01p | | Bejo | *Cichorium intybus* | Male sterile | RM3-3, RM3-4, RM3-6 |
| 97-099-01p | | Monsanto | Corn | Glyphosate tolerant | GA21 |
| 97-013-01p | | Calgene | Cotton | Bromoxynil tolerant & Lepidopteran resistant | Events 31807 & 31808 |
| 97-008-01p | | Du Pont | Soybean | Oil profile altered | G94-1, G94-19, G-168 |
| 96-317-01p | | Monsanto | Corn | Glyphosate tolerant & ECB resistant | MON802 |
| 96-291-01p | | DeKalb | Corn | European Corn Borer resistant | DBT418 |
| 96-248-01p | 92-196-01p | Calgene | Tomato | Fruit ripening altered | 1 additional FLAVRSAVR line |
| 96-068-01p | | AgrEvo | Soybean | Phosphinothricin tolerant | W62, W98, A2704-12, A2704-21, A5547-35 |
| 96-051-01p | | Cornell U | Papaya | PRSV resistant | 55-1, 63-1 |
| 96-017-01p | 95-093-01p | Monsanto | Corn | European Corn Borer resistant | MON809 & MON810 |
| 95-352-01p | | Asgrow | Squash | CMV, ZYMV, WMV2 resistant | CZW-3 |

TABLE B-continued

Petitions of Nonregulated Status Granted or Pending by APHIS as of Mar. 31, 2010

Applicant Documents

| Petition | Extension of Petition Number *** | Institution | Regulated Article | Transgenic Phenotype | Transformation Event or Line |
|---|---|---|---|---|---|
| 95-338-01p | | Monsanto | Potato | CPB resistant | SBT02-5 & -7, ATBT04-6 &-27, -30, -31, -36 |
| 95-324-01p | | Agritope | Tomato | Fruit ripening altered | 35 1 N |
| 95-256-01p | | Du Pont | Cotton | Sulfonylurea tolerant | 19-51a |
| 95-228-01p | | Plant Genetic Systems | Corn | Male sterile | MS3 |
| 95-195-01p | | Northrup King | Corn | European Corn Borer resistant | Bt11 |
| 95-179-01p | 92-196-01p | Calgene | Tomato | Fruit ripening altered | 2 additional FLAVRSAVR lines |
| 95-145-01p | | DeKalb | Corn | Phosphinothricin tolerant | B16 |
| 95-093-01p | | Monsanto | Corn | Lepidopteran resistant | MON 80100 |
| 95-053-01p | | Monsanto | Tomato | Fruit ripening altered | 8338 |
| 95-045-01p | | Monsanto | Cotton | Glyphosate tolerant | 1445, 1698 |
| 95-030-01p | 92-196-01p | Calgene | Tomato | Fruit ripening altered | 20 additional FLAVRSAVR lines |
| 94-357-01p | | AgrEvo | Corn | Phosphinothricin tolerant | T14, T25 |
| 94-319-01p | | Ciba Seeds | Corn | Lepidopteran resistant | Event 176 |
| 94-308-01p | | Monsanto | Cotton | Lepidopteran resistant | 531, 757, 1076 |
| 94-290-01p | | Zeneca & Petoseed | Tomato | Fruit polygalacturonase level decreased | B, Da, F |
| 94-257-01p | | Monsanto | Potato | Coleopteran resistant | BT6, BT10, BT12, BT16, BT17, BT18, BT23 |
| 94-230-01p | 92-196-01p | Calgene | Tomato | Fruit ripening altered | 9 additional FLAVRSAVR lines |
| 94-228-01p | | DNA Plant Tech | Tomato | Fruit ripening altered | 1345-4 |
| 94-227-01p | 92-196-01p | Calgene | Tomato | Fruit ripening altered | Line N73 1436-111 |
| 94-090-01p | | Calgene | Rapeseed | Oil profile altered | pCGN3828-212/86- 18 & 23 |
| 93-258-01p | | Monsanto | Soybean | Glyphosate tolerant | 40-3-2 |
| 93-196-01p | | Calgene | Cotton | Bromoxynil tolerant | BXN |
| 92-204-01p | | Upjohn | Squash | WMV2 & ZYMV resistant | ZW-20 |
| 92-196-01p | | Calgene | Tomato | Fruit ripening altered | FLAVR SAVR |

NOTE:
To obtain the most up-to-date list of Crops No Longer Regulated, please look at the Current Status of Petitions. This list is automatically updated and reflects all petitions received to date by APHIS, including petitions pending, withdrawn, or approved.
Abbreviations:
CMV—cucumber mosaic virus; CPB—colorado potato beetle; PLRV—potato leafroll virus; PRSV—papaya ringspot virus; PVY—potato virus Y; WMV2—watermelon mosaic virus 2 ZYMV—zucchini yellow mosaic virus
*** Extension of Petition Number: Under 7CFR 340.6(e) a person may request that APHIS extend a determination of non-regulated status to other organisms based on their similarity of the previously deregulated article. This column lists the previously granted petition of that degregulated article.
**** Preliminary EA: The Environmental Assessment initially available for Public comment prior to finalization.

TABLE C

| Plant species | Event | Trait | Patent reference |
|---|---|---|---|
| Corn | PV-ZMGT32 (NK603) | Glyphosate tolerance | US 2007-056056 |
| Corn | MIR604 | Insect resistance (Cry3a055) | EP 1 737 290 |
| Corn | LY038 | High lysine content | U.S. Pat. No. 7,157,281 |
| Corn | 3272 | Self processing corn (alpha-amylase) | US 2006-230473 |
| Corn | PV-ZMIR13 (MON863) | Insect resistance (Cry3Bb) | US 2006-095986 |
| Corn | DAS-59122-7 | Insect resistance (Cry34Ab1/Cry35Ab1) | US 2006-070139 |
| Corn | TC1507 | Insect resistance (Cry1F) | U.S. Pat. No. 7,435,807 |
| Corn | MON810 | Insect resistance (Cry1Ab) | US 2004-180373 |
| Corn | VIP1034 | Insect resistance | WO 03/052073 |
| Corn | B16 | Glufosinate resistance | US 2003-126634 |
| Corn | GA21 | Glyphosate resistance | U.S. Pat. No. 6,040,497 |
| Corn | GG25 | Glyphosate resistance | U.S. Pat. No. 6,040,497 |
| Corn | GJ11 | Glyphosate resistance | U.S. Pat. No. 6,040,497 |
| Corn | FI117 | Glyphosate resistance | U.S. Pat. No. 6,040,497 |
| Corn | GAT-ZM1 | Glufosinate tolerance | WO 01/51654 |

TABLE C-continued

| Plant species | Event | Trait | Patent reference |
|---|---|---|---|
| Corn | MON87460 | Drought tolerance | WO 2009/111263 |
| Corn | DP-098140-6 | Glyphosate tolerance/ALS inhibitor tolerance | WO 2008/112019 |
| Wheat | Event 1 | Fusarium resistance (trichothecene 3-O-acetyltransferase) | CA 2561992 |
| Sugar beet | T227-1 | Glyphosate tolerance | US 2004-117870 |
| Sugar beet | H7-1 | Glyphosate tolerance | WO 2004-074492 |
| Soybean | MON89788 | Glyphosate tolerance | US 2006-282915 |
| Soybean | A2704-12 | Glufosinate tolerance | WO 2006/108674 |
| Soybean | A5547-35 | Glufosinate tolerance | WO 2006/108675 |
| Soybean | DP-305423-1 | High oleic acid/ALS inhibitor tolerance | WO 2008/054747 |
| Rice | GAT-OS2 | Glufosinate tolerance | WO 01/83818 |
| Rice | GAT-OS3 | Glufosinate tolerance | US 2008-289060 |
| Rice | PE-7 | Insect resistance (Cry1Ac) | WO 2008/114282 |
| Oilseed rape | MS-B2 | Male sterility | WO 01/31042 |
| Oilseed rape | MS-BN1/RF-BN1 | Male sterility/restoration | WO 01/41558 |
| Oilseed rape | RT73 | Glyphosate resistance | WO 02/36831 |
| Cotton | CE43-67B | Insect resistance (Cry1Ab) | WO 2006/128573 |
| Cotton | CE46-02A | Insect resistance (Cry1Ab) | WO 2006/128572 |
| Cotton | CE44-69D | Insect resistance (Cry1Ab) | WO 2006/128571 |
| Cotton | 1143-14A | Insect resistance (Cry1Ab) | WO 2006/128569 |
| Cotton | 1143-51B | Insect resistance (Cry1Ab) | WO 2006/128570 |
| Cotton | T342-142 | Insect resistance (Cry1Ab) | WO 2006/128568 |
| Cotton | event3006-210-23 | Insect resistance (Cry1Ac) | WO 2005/103266 |
| Cotton | PV-GHGT07 (1445) | Glyphosate tolerance | US 2004-148666 |
| Cotton | MON88913 | Glyphosate tolerance | WO 2004/072235 |
| Cotton | EE-GH3 | Glyphosate tolerance | WO 2007/017186 |
| Cotton | T304-40 | Insect-resistance (Cry1Ab) | WO2008/122406 |
| Cotton | Cot202 | Insect resistance (VIP3) | US 2007-067868 |
| Cotton | LLcotton25 | Glufosinate resistance | WO 2007/017186 |
| Cotton | EE-GH5 | Insect resistance (Cry1Ab) | WO 2008/122406 |
| Cotton | event 281-24-236 | Insect resistance (Cry1F) | WO 2005/103266 |
| Cotton | Cot102 | Insect resistance (Vip3A) | US 2006-130175 |
| Cotton | MON 15985 | Insect resistance (Cry1A/Cry2Ab) | US 2004-250317 |
| Bent Grass | Asr-368 | Glyphosate tolerance | US 2006-162007 |
| Brinjal | EE-1 | Insect resistance (Cry1Ac) | WO 2007/091277 |

Among the diseases of plants or crops that can be controlled by the method according to the invention, mention can be made of:

Powdery mildew diseases such as:
*Blumeria* diseases, caused for example by *Blumeria graminis*;
*Podosphaera* diseases, caused for example by *Podosphaera leucotricha*;
*Sphaerotheca* diseases, caused for example by *Sphaerotheca fuliginea*;
*Uncinula* diseases, caused for example by *Uncinula necator*;

Rust diseases such as:
*Gymnosporangium* diseases, caused for example by *Gymnosporangium sabinae*;
*Hemileia* diseases, caused for example by *Hemileia vastatrix*;
*Phakopsora* diseases, caused for example by *Phakopsora pachyrhizi* or *Phakopsora meibomiae*;
*Puccinia* diseases, caused for example by *Puccinia recondite*, *Puccinia graminis* or *Puccinia striiformis*;
*Uromyces* diseases, caused for example by *Uromyces appendiculatus*;

Oomycete diseases such as:
*Albugo* diseases caused for example by *Albugo candida*;
*Bremia* diseases, caused for example by *Bremia lactucae*;
*Peronospora* diseases, caused for example by *Peronospora pisi* or *P. brassicae*;
*Phytophthora* diseases, caused for example by *Phytophthora infestans*;
*Plasmopara* diseases, caused for example by *Plasmopara viticola*;
*Pseudoperonospora* diseases, caused for example by *Pseudoperonospora humuli* or *Pseudoperonospora cubensis*;
*Pythium* diseases, caused for example by *Pythium ultimum*;

Leafspot, leaf blotch and leaf blight diseases such as:
*Alternaria* diseases, caused for example by *Alternaria solani*;
*Cercospora* diseases, caused for example by *Cercospora beticola*;
*Cladiosporum* diseases, caused for example by *Cladiosporium cucumerinum*;
*Cochliobolus* diseases, caused for example by *Cochliobolus sativus* (Conidiaform: *Drechslera*, Syn: *Helminthosporium*) or *Cochliobolus miyabeanus*;
*Colletotrichum* diseases, caused for example by *Colletotrichum lindemuthanium*;
*Cycloconium* diseases, caused for example by *Cycloconium oleaginum*;
*Diaporthe* diseases, caused for example by *Diaporthe citri*;
*Elsinoe* diseases, caused for example by *Elsinoe fawcettii*;
*Gloeosporium* diseases, caused for example by *Gloeosporium laeticolor*;
*Glomerella* diseases, caused for example by *Glomerella cingulata*;
*Guignardia* diseases, caused for example by *Guignardia bidwelli*;

*Leptosphaeria* diseases, caused for example by *Leptosphaeria maculans*; *Leptosphaeria nodorum*;
*Magnaporthe* diseases, caused for example by *Magnaporthe grisea*;
*Mycosphaerella* diseases, caused for example by *Mycosphaerella graminicola*; *Mycosphaerella arachidicola*; *Mycosphaerella fijiensis*;
*Phaeosphaeria* diseases, caused for example by *Phaeosphaeria nodorum*;
*Pyrenophora* diseases, caused for example by *Pyrenophora teres*, or *Pyrenophora tritici repentis*;
*Ramularia* diseases, caused for example by *Ramularia collo-cygni*, or *Ramularia areola*;
*Rhynchosporium* diseases, caused for example by *Rhynchosporium secalis*;
*Septoria* diseases, caused for example by *Septoria apii* or *Septoria lycopercisi*;
*Typhula* diseases, caused for example by *Typhula incarnate*;
*Venturia* diseases, caused for example by *Venturia inaequalis*;
Root, Sheath and stem diseases such as:
*Corticium* diseases, caused for example by *Corticium graminearum*;
*Fusarium* diseases, caused for example by *Fusarium oxysporum*;
*Gaeumannomyces* diseases, caused for example by *Gaeumannomyces graminis*;
*Rhizoctonia* diseases, caused for example by *Rhizoctonia solani*;
*Sarocladium* diseases caused for example by *Sarocladium oryzae*;
*Sclerotium* diseases caused for example by *Sclerotium oryzae*;
*Tapesia* diseases, caused for example by *Tapesia acuformis*;
*Thielaviopsis* diseases, caused for example by *Thielaviopsis basicola*;
Ear and panicle diseases such as:
*Alternaria* diseases, caused for example by *Alternaria* spp.;
*Aspergillus* diseases, caused for example by *Aspergillus flavus*;
*Cladosporium* diseases, caused for example by *Cladosporium* spp.;
*Claviceps* diseases, caused for example by *Claviceps purpurea*;
*Fusarium* diseases, caused for example by *Fusarium culmorum*;
*Gibberella* diseases, caused for example by *Gibberella zeae*;
*Monographella* diseases, caused for example by *Monographella nivalis*;
Smut and bunt diseases such as:
*Sphacelotheca* diseases, caused for example by *Sphacelotheca reiliana*;
*Tilletia* diseases, caused for example by *Tilletia caries*;
*Urocystis* diseases, caused for example by *Urocystis occulta*;
*Ustilago* diseases, caused for example by *Ustilago nuda*;
Fruit rot and mould diseases such as:
*Aspergillus* diseases, caused for example by *Aspergillus flavus*;
*Botrytis* diseases, caused for example by *Botrytis cinerea*;
*Penicillium* diseases, caused for example by *Penicillium expansum*;
*Rhizopus* diseases caused by example by *Rhizopus stolonifer*
*Sclerotinia* diseases, caused for example by *Sclerotinia sclerotiorum*;
*Verticilium* diseases, caused for example by *Verticilium alboatrum*;
Seed and soilborne decay, mould, wilt, rot and damping-off diseases:
*Alternaria* diseases, caused for example by *Alternaria brassicicola*
*Aphanomyces* diseases, caused for example by *Aphanomyces euteiches*
*Ascochyta* diseases, caused for example by *Ascochyta lentis*
*Aspergillus* diseases, caused for example by *Aspergillus flavus*
*Cladosporium* diseases, caused for example by *Cladosporium herbarum*
*Cochliobolus* diseases, caused for example by *Cochliobolus sativus* (Conidiaform: *Drechslera, Bipolaris* Syn: *Helminthosporium*);
*Colletotrichum* diseases, caused for example by *Colletotrichum coccodes*;
*Fusarium* diseases, caused for example by *Fusarium culmorum*;
*Gibberella* diseases, caused for example by *Gibberella zeae*;
*Macrophomina* diseases, caused for example by *Macrophomina phaseolina*
*Monographella* diseases, caused for example by *Monographella nivalis*;
*Penicillium* diseases, caused for example by *Penicillium expansum*
*Phoma* diseases, caused for example by *Phoma lingam*
*Phomopsis* diseases, caused for example by *Phomopsis sojae*;
*Phytophthora* diseases, caused for example by *Phytophthora cactorum*;
*Pyrenophora* diseases, caused for example by *Pyrenophora graminea*
*Pyricularia* diseases, caused for example by *Pyricularia oryzae*;
*Pythium* diseases, caused for example by *Pythium ultimum*;
*Rhizoctonia* diseases, caused for example by *Rhizoctonia solani*;
*Rhizopus* diseases, caused for example by *Rhizopus oryzae*
*Sclerotium* diseases, caused for example by *Sclerotium rolfsii*;
*Septoria* diseases, caused for example by *Septoria nodorum*;
*Typhula* diseases, caused for example by *Typhula incarnate*;
*Verticillium* diseases, caused for example by *Verticillium dahliae*;
Canker, broom and dieback diseases such as:
*Nectria* diseases, caused for example by *Nectria galligena*;
Blight diseases such as:
*Monilinia* diseases, caused for example by *Monilinia laxa*;
Leaf blister or leaf curl diseases such as:
*Exobasidium* diseases caused for example by *Exobasidium vexans*
*Taphrina* diseases, caused for example by *Taphrina deformans*;
Decline diseases of wooden plants such as:
Esca diseases, caused for example by *Phaemoniella clamydospora*;

*Eutypa* dyeback, caused for example by *Eutypa lata;*
*Ganoderma* diseases caused for example by *Ganoderma boninense;*
*Rigidoporus* diseases caused for example by *Rigidoporus lignosus*
Diseases of Flowers and Seeds such as
*Botrytis* diseases caused for example by *Botrytis cinerea;*
Diseases of Tubers such as
*Rhizoctonia* diseases caused for example by *Rhizoctonia solani;*
*Helminthosporium* diseases caused for example by *Helminthosporium solani;*
Club root diseases such as
*Plasmodiophora* diseases, cause for example by *Plamodiophora brassicae.*
Diseases caused by Bacterial Organisms such as
*Xanthomonas* species for example *Xanthomonas campestris* pv. *oryzae;*
*Pseudomonas* species for example *Pseudomonas syringae* pv. *lachrymans;*
*Erwinia* species for example *Erwinia amylovora.*

The composition according to the invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds according to the invention or a composition according to the invention; this includes for example direct application, spraying, dipping, injection or any other suitable means.

The dose of active compound usually applied in the method of treatment according to the invention is generally and advantageously from 10 to 800 g/ha, preferably from 50 to 300 g/ha for applications in foliar treatment. The dose of active substance applied is generally and advantageously from 2 to 200 g per 100 kg of seed, preferably from 3 to 150 g per 100 kg of seed in the case of seed treatment. It is clearly understood that the doses indicated herein are given as illustrative examples of the method according to the invention. A person skilled in the art will know how to adapt the application doses, notably according to the nature of the plant or crop to be treated.

The compounds or mixtures according to the invention can also be used for the preparation of composition useful to curatively or preventively treat human or animal fungal diseases such as, for example, mycoses, dermatoses, trichophyton diseases and candidiases or diseases caused by *Aspergillus* spp., for example *Aspergillus fumigatus.*

The preparation and the use of the active compounds I-methyl-3-dihalogenomethyl-5-halogenopyrazole(thio)carboxamides of the formula (I) according to the invention and the intermediates is illustrated by the examples below.

Procedure for Synthesizing Amides of the Formula (I) According to the Invention from Compounds of the Formula (II) and Compounds of the Formula (III)

5-Chloro-3-(difluoromethyl)-1-methyl-N-[2-(4-methylpentan-2-yl)phenyl]-1H-pyrazole-4-carboxamide (Example 14)

0.458 g (2.00 mmol) of 5-chloro-3-(difluoromethyl)-1-methyl-1H-pyrazole-4-carbonyl chloride is added to a mixture of 0.322 g (1.81 mmol) of 2-(4-methylpentan-2-yl) aniline and 0.377 g (2.72 mmol) of potassium carbonate in 30 mL of acetonitrile, and the mixture is stirred at 20° C. overnight. After the reaction has ended, the mixture is extracted with water/ethyl acetate. The organic phase is dried with sodium sulfate and concentrated under reduced pressure. The crude product is purified by column chromatography (mobile phase: cyclohexane/ethyl acetate gradient). This gives 0.580 g (78% of theory) of 5-chloro-3-(difluoromethyl)-1-methyl-N-[2-(4-methylpentan-2-yl)phenyl]-1H-pyrazole-4-carboxamide having a content of 94% according to LC-MS and a logP (acidic) of 4.01.

$^1$H NMR (400 MHz, DMSO-d) δ ppm: 0.7-0.80 (m, 1H); 1.10-1.20 (m, 1H); 1.30-1.50 (m, 1H); 3.10-3.20 (m, 1H); 3.90-4.00 (s, 1H); 7.10-7.40 (m, 1H)

Procedure for Synthesizing the Carboxylic Acid Derivatives of the Formula (II) According to the Invention According to Process P1

5-Chloro-3-(difluoromethyl)-1-methyl-1H-pyrazole-4-carboxylic acid (Example IIb)

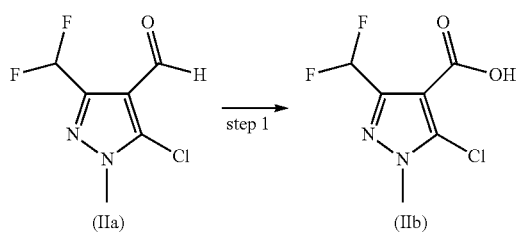

In a 500 mL round-bottom flask, 6.0 g (31 mmol) of 5-chloro-3-(difluoromethyl)-1-methyl-1H-pyrazole-4-carbaldehyde were taken up in 30 mL of toluene. A solution of 2.4 g (62 mmol) of sodium hydroxide in 6 mL of water was added to the reaction mixture, followed by 103 mL of a 30% strength solution of hydrogen peroxide in water. During the addition, the temperature was kept below 37° C. The reaction mixture was then stirred at 50° C. for 7 h. After cooling, the organic phase was extracted with 100 mL of water. The aqueous phase was acidified to pH 2 using dilute hydrochloric acid. The white precipitate formed was filtered off, washed twice with 20 mL of water and dried. This gave 3.2 g of 5-chloro-3-(difluoromethyl)-1-methyl-1H-pyrazole-4-carboxylic acid as a white solid.

$^1$H NMR (400 MHz, DMSO-d$_6$) δ ppm: 3.78 (s, 3H); 7.12 (t, 1H, $J_{HF}$=53.60 Hz); 13.19 (s, 1H);
IR (KBr): 1688 cm$^{-1}$ (C=O); 2200-3200 cm$^{-1}$ broad;

5-Chloro-3-(difluoromethyl)-1-methyl-1H-pyrazole-4-carbonyl chloride (Example IIe)

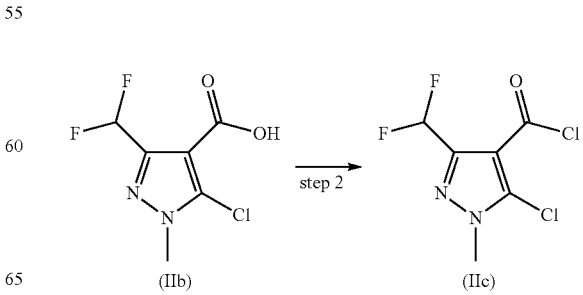

3.2 g of 5-chloro-3-(difluoromethyl)-1-methyl-1H-pyrazole-4-carboxylic acid and 44.3 mL of thionyl chloride were heated under reflux for 5 h. After cooling, the reaction mixture was concentrated under reduced pressure, giving 3.5 g of 5-chloro-3-(difluoromethyl)-1-methyl-1H-pyrazole-4-carbonyl chloride as a yellow oil.

$^1$H NMR (400 MHz, CHCl$_3$-d$_6$) δ ppm: 3.97 (s, 3H); 7.00 (t, J=52.01 Hz, 1H);

IR (TQ): 1759 and 1725 cm$^{-1}$ (C=O);

3-(Difluoromethyl)-5-fluoro-1-methyl-1H-pyrazole-4-carbonyl fluoride (Example IId)

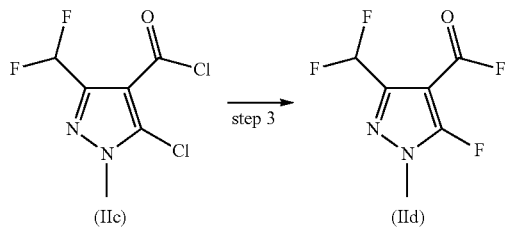

At 100° C., a solution of 5.0 g (22 mmol) of 5-chloro-3-(difluoromethyl)-1-methyl-1H-pyrazole-4-carbonyl chloride in 15 mL of toluene was added to a dried solution of 4.0 g (70 mmol) of potassium fluoride in 21 mL of tetrahydrothiophene-1,1-dioxide. The reaction mixture was then stirred at 190-200° C. for 22 h. Removal of the solvent under reduced pressure gave 8 g of a solution (25% molar) of 3-(difluoromethyl)-5-fluoro-1-methyl-1H-pyrazole-4-carbonyl fluoride in tetrahydrothiophene-1,1-dioxide.

$^1$H NMR (250 MHz, CHCl$_3$-d$_6$) δ ppm: 3.87 (s, 3H); 6.79 (t, J=53.75 Hz, 1H);

$^{19}$F NMR (250 MHz, CHCl$_3$-d$_6$) δ ppm: 45.37 (s, COF); −117.5 (d, J=28.2 Hz); −131.6 (m);

5-Fluoro-3-(difluoromethyl)-1-methyl-1H-pyrazole-4-carboxylic acid (Example IIe)

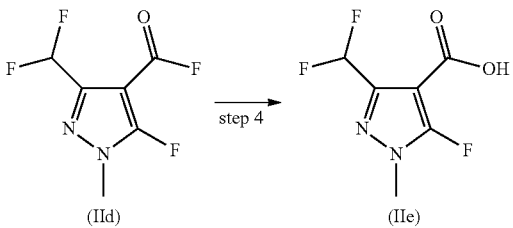

67.5 g of a solution (10% molar) of 3-(difluoromethyl)-5-fluoro-1-methyl-1H-pyrazole-4-carbonyl fluoride in tetrahydrothiophene-1,1-dioxide were added dropwise to 400 mL of an aqueous 1N NaOH solution. During the addition, the temperature was kept below 20° C. After 2 h of stirring at room temperature, the mixture was carefully acidified to pH 2 using concentrated hydrochloric acid. The white precipitate formed was filtered off, washed with water and dried. This gave 6 g of 5-fluoro-3-(difluoromethyl)-1-methyl-1H-pyrazole-4-carboxylic acid as a white solid.

$^1$H NMR (400 MHz, DMSO-d$_6$) δ ppm: 3.90 (s, 3H); 7.22 (t, 1H, J$_{HF}$=53.55 Hz); 13.33 (s, 1H);

5-Fluoro-3-(difluoromethyl)-1-methyl-1H-pyrazole-4-carbonyl chloride (Example IIf)

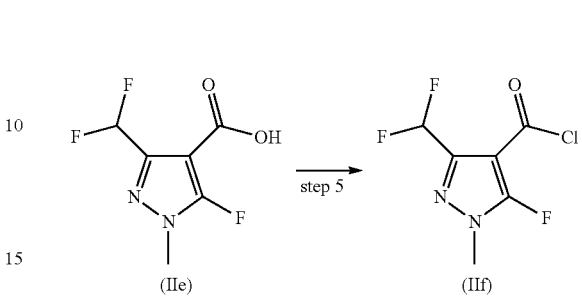

9.1 g of 5-fluoro-3-(difluoromethyl)-1-methyl-1H-pyrazole-4-carboxylic acid and 75.5 mL of thionyl chloride were heated under reflux for 1.5 h. After cooling, the reaction mixture was concentrated under reduced pressure, giving 10 g of 5-fluoro-3-(difluoromethyl)-1-methyl-1H-pyrazole-4-carbonyl chloride as a yellow oil.

GC-MS (M$^{+\cdot}$)=212; fragments: (M$^{+\cdot}$-Cl)=177 and (M$^{+\cdot}$-F)=193;

The following amines of the formula (III), as shown above, are novel and are synthesized as described below:

Preparation of 5-fluoro-4'-(trifluoromethyl)biphenyl-2-amine (amine of Example 118)

Under argon, a mixture of 9.0 g (37.9 mmol) of 4-fluoro-2-(4,4,5,5-tetramethyl-1,3,2-dioxaborolan-2-yl)aniline, 10.25 g (45.5 mmol) of 4-bromobenzotrifluoride, 1.39 g (1.89 mmol) of 1,1'-bis(diphenyl-phosphino)ferrocenepalladium (II) chloride and 20.11 g (189 mmol) of sodium carbonate in 200 mL of DMSO and 70 mL of water is stirred at 90° C. overnight. After the reaction has ended, the mixture is cooled to room temperature, water is added and the mixture is extracted with ethyl acetate. The organic phase is once more washed with water, dried with sodium sulfate and concentrated under reduced pressure. The crude product is purified by column chromatography (mobile phase: cyclohexane/ethyl acetate gradient). This gives 5.28 g (53% of theory) of 5-fluoro-4'-(trifluoromethyl)biphenyl-2-amine having a content of 97% according to LC-MS and a logP (acidic) of 3.52.

$^1$H NMR (400 MHz, CD3CN-d) δ ppm: 4.00-4.10 (s, 1H); 6.78-6.80 (m, 1H); 6.90-7.00 (m, 1H), 7.60-7.70 (m, 1H), 7.80-7.90 (m, 1H)

General Procedure for Synthesizing Thioamides of the Formula (I) According to the Invention from Amides of the Formula (I) According to Process P2

In a 13 mL Chemspeed™ vial is weighed 0.27 mmol of phosphorous pentasulfide (P$_2$S$_5$). 3 mL of a 0.18 molar solution of the amide (I) (0.54 mmol) in dioxane is added and the mixture is heated at reflux for two hours. The temperature is then cooled to 80° C. and 2.5 mL of water are added. The mixture is heated at 80° C. for one more hour. 2 mL of water are then added and the reaction mixture is extracted twice by 4 mL of dichloromethane. The organic phase is deposited on a basic alumina cartridge (2 g) and eluted twice by 8 mL of dichloromethane. The solvents are removed and the crude thioamide derivative is analyzed by LCMS and NMR. Insufficiently pure compounds are further purified by preparative LCMS.

The following examples of compounds according to formula (I) are listed in Table 1 below:

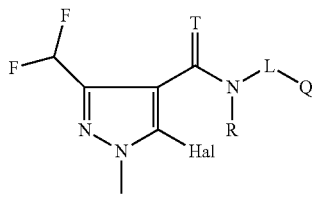
(I)

where R represents hydrogen and L has the following meaning in Table 1 below:

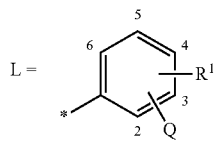

where the bond marked by * is attached to the amide;
or

Q and R¹ together with the carbon atoms to which they are attached form an optionally substituted 5-, 6- or 7-membered carbocyclic or saturated heterocyclic ring;
or L and Q together form a radical of the formula W1

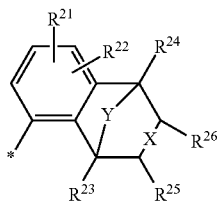
(W1)

where the bond marked by * is attached to the amide;

TABLE 1

| Ex. | Hal | T | R¹ | position of Q | Q | logP | Mass (M + H) |
|---|---|---|---|---|---|---|---|
| 1 | F | O | | 2- | isopropyl | 2.82 | 312 |
| 2 | Cl | O | | 2- | isopropyl | 3.02 | 328 |
| 3 | F | O | | 2- | tert-butyl | 2.98 | 326 |
| 4 | Cl | O | | 2- | tert-butyl | 3.21 | 342 |
| 5 | Cl | O | | 2- | 3-methylbut-2-en-1-yl | 3.35 | |
| 6 | F | O | | 2- | 3-methylbut-2-en-1-yl | 3.20 | |
| 7 | F | O | | 2- | 3-methylbutyl | 3.60 | |
| 8 | F | O | | 2- | pentan-2-yl | 3.55 | 340 |
| 9 | Cl | O | | 2- | pentan-2-yl | 3.77 | 356 |
| 10 | F | O | 4-fluoro | 2- | 3-methylbutyl | 3.67 | 358 |
| 11 | F | O | | 2- | 4-methylpentan-2-yl | 3.85 | 354 |
| 12 | Cl | O | | 2- | 4-methylbutyl | 4.01 | |
| 13 | F | O | | 2- | 3,3-dimethylbutyl | 3.83 | |
| 14 | Cl | O | | 2- | 3,3-dimethylbutyl | 4.10 | |
| 15 | F | O | 6-methyl | 2- | 3,3-dimethylbutyl | 3.85 | 368 |
| 16 | F | O | 3-methyl | 2- | 3,3-dimethylbutyl | 4.06 | 368 |

TABLE 1-continued

| Ex. | Hal | T | R¹ | position of Q | Q | logP | Mass (M + H) |
|---|---|---|---|---|---|---|---|
| 17 | F | O | 5-methyl | 2- | 3,3-dimethylbutyl | 4.29 | 368 |
| 18 | F | O | 5-chloro | 2- | 3,3-dimethylbutyl | 4.51 | 388 |
| 19 | F | O | | 2- | 3-methoxy-3-methylbut-1-yn-1-yl | 3.34 | |
| 20 | F | O | | 2- | 5-methylhexan-3-yl | 4.28 | |
| 21 | F | O | | 2- | 4,4-dimethylpentan-2-yl | 4.04 | |
| 22 | Cl | O | | 2- | 4,4-dimethylpentan-2-yl | 4.31 | |
| 23 | F | O | | 2- | 3-methoxy-3-methylbutyl | 2.74 | |
| 24 | Cl | O | | 2- | 2-(trimethylsilyl)ethyl | 4.36 | |
| 25 | Cl | S | | 2- | 2-(trimethylsilyl)ethyl | 4.56 | 402 |
| 26 | F | O | | 2- | prop-2-yn-1-yloxy | 2.71 | 324 |
| 27 | F | O | | 2- | 2,2-dimethylpropoxy | 4.08 | |
| 28 | F | O | 4-fluoro | 2- | 2,2-dimethylpropoxy | 4.08 | |
| 29 | F | O | | 2- | 1,1,2,2-tetrafluoroethoxy | 3.08 | 386 |
| 30 | Cl | O | | 2- | 1,1,2,2-tetrafluoroethoxy | 3.31 | 402 |
| 31 | Cl | O | | 2- | 1,1,2,3,3,3-hexafluoropropoxy | 3.71 | 452 |
| 32 | F | O | | 2- | 1,1,2,3,3,3-hexafluoropropoxy | 3.48 | 436 |
| 33 | F | O | 3-chloro | 2- | (2,2-difluoroethyl)sulfanyl | 3.53 | 400 |
| 34 | F | O | 5-fluoro | 2- | (2,2-difluoroethyl)sulfanyl | 3.33 | 384 |
| 35 | F | O | 5-(trifluoromethyl) | 2- | (2,2-difluoroethyl)sulfanyl | | 434 |
| 36 | F | O | | 2- | (trifluoromethyl)sulfanyl | 3.37 | 370 |
| 37 | F | O | | 2- | (2,2,2-trifluoroethyl)sulfanyl | 3.29 | 384 |
| 38 | F | O | 5-methyl | 2- | (2,2,2-trifluoroethyl)sulfanyl | 3.69 | 398 |
| 39 | F | O | 3-chloro | 2- | (2,2,2-trifluoroethyl)sulfanyl | 3.73 | 418 |
| 40 | F | O | 5-chloro | 2- | (2,2,2-trifluoroethyl)sulfanyl | 3.92 | 418 |
| 41 | F | O | | 2- | [(2,2-dichlorocyclopropyl)methyl]sulfanyl | 3.27 | 424 |
| 42 | F | O | | 2- | (heptafluoropropyl)sulfanyl | 4.25 | 470 |
| 43 | F | O | | 2- | bromo | 2.82 | 348 |
| 44 | Cl | O | | 2- | bromo | 3.13 | 364 |
| 45 | F | O | | 2- | cyclopropyl | 2.96 | 310 |
| 46 | F | O | | 2- | 1,1'-bi(cyclopropyl)-2-yl | 3.67 | 350 |
| 47 | Cl | O | | 2- | 1,1'-bi(cyclopropyl)-2-yl | 3.76 isomer A | |
| 48 | Cl | O | | 2- | 1,1'-bi(cyclopropyl)-2-yl | 3.85 isomer B | |
| 49 | Cl | S | | 2- | 1,1'-bi(cyclopropyl)-2-yl | 3.79 isomer A | 382 |
| 50 | Cl | S | | 2- | 1,1'-bi(cyclopropyl)-2-yl | 3.81 isomer B | 382 |
| 51 | F | O | | 2- | bicyclo[2.2.1]hept-2-yl | 3.78 | |
| 52 | F | O | | 2- | 3-methylcyclohexyl | 3.23 | 366 |
| 53 | Cl | O | | 2- | 3-methylcyclohexyl | 4.29 | 382 |
| 54 | F | O | | | 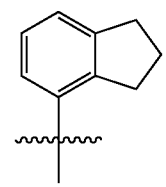 [SMILES: *c1cccc2c1CCC2] | 2.94 | 310 |

TABLE 1-continued

| Ex. | Hal | T | R¹ | position of Q | Q | logP | Mass (M+H) |
|---|---|---|---|---|---|---|---|
| 55 | Cl | O | | | (2,3-dihydro-1H-inden-4-yl) | 3.19 | 326 |
| 56 | F | O | | | (5,6,7,8-tetrahydronaphthalen-1-yl) | 3.08 | 324 |
| 57 | Cl | O | | | (5,6,7,8-tetrahydronaphthalen-1-yl) | 3.31 | 340 |
| 58 | Cl | O | | | (2,3-dihydrobenzo[b][1,4]dioxin-5-yl) | 2.70 | 344 |
| 59 | F | O | | | (2,3-dihydrobenzo[b][1,4]dioxin-5-yl) | 2.44 | 328 |
| 60 | H | O | | | (1,1,3-trimethyl-1,3-dihydroisobenzofuran) | | |
| 61 | Cl | O | | | (1,1,3-trimethyl-1,3-dihydroisobenzofuran) | | |
| 62 | F | O | | | (2,2-difluorobenzo[d][1,3]dioxol-4-yl) | 2.77 | 350 |
| 63 | Cl | O | | | (2,2-difluorobenzo[d][1,3]dioxol-4-yl) | 3.00 | 366 |
| 64 | F | O | | | (1,1,3-trimethyl-2,3-dihydro-1H-inden-4-yl) | 3.69 | 352 |
| 65 | Cl | O | | | (1,1,3-trimethyl-2,3-dihydro-1H-inden-4-yl) | 4.04 | 368 |
| 66 | F | O | | | (isopropyl-methanobenzene) | 4.41 | 378 |
| 67 | Cl | O | | | (isopropyl-methanobenzene) | 4.55 | |
| 68 | Cl | S | | | (isopropyl-methanobenzene) | 4.71 | 410 |
| 69 | F | O | | | (trifluoromethyl-tetrahydronaphthalenyl) | 3.27 | 392 |
| 70 | Cl | O | | | (trifluoromethyl-tetrahydronaphthalenyl) | 3.46 | 408 |

TABLE 1-continued

| Ex. | Hal | T | R¹ | position of Q | Q | logP | Mass (M+H) |
|---|---|---|---|---|---|---|---|
| 71 | Cl | O | | | 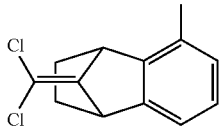 | 4.21 | 432 |
| 72 | F | O | | | 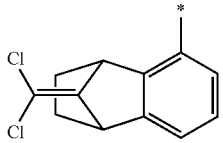 | 3.99 | 416 |
| 73 | F | O | | 2- | phenyl | 3.25 | 346 |
| 74 | Cl | O | | 2- | phenyl | 3.59 | 362 |
| 75 | F | O | | 2- | 2-methylphenyl | 3.74 | 360 |
| 76 | Cl | O | | 2- | 2-methylphenyl | 4.14 | 376 |
| 77 | F | O | 4-fluoro | 2- | 4-fluorophenyl | 3.16 | |
| 78 | Cl | O | | 2- | 4-fluorophenyl | 3.40 | |
| 79 | Cl | O | 4-fluoro | 2- | 4-fluorophenyl | 3.41 | |
| 80 | F | O | | 2- | 4-fluorophenyl | 3.20 | |
| 81 | F | O | | 2- | 3,5-dimethylphenyl | 4.11 | 374 |
| 82 | Cl | O | | 2- | 3,5-dimethylphenyl | 4.51 | 390 |
| 83 | Cl | O | 4-fluoro | 2- | 4-chlorophenyl | 3.76 | |
| 84 | F | O | 4-fluoro | 2- | 4-chlorophenyl | 3.46 | |
| 85 | F | O | | 2- | 4-chlorophenyl | 3.57 | 380 |
| 86 | F | O | | 2- | 3-chlorophenyl | 3.55 | 380 |
| 87 | Cl | O | | 2- | 3-chlorophenyl | 3.87 | 396 |
| 88 | Cl | O | | 2- | 4-chlorophenyl | 3.85 | 396 |
| 89 | Cl | O | | 2- | 3,4-difluorophenyl | 3.40 | |
| 90 | F | O | | 2- | 3,4-difluorophenyl | 3.20 | |
| 91 | F | O | | 2- | 3,5-difluorophenyl | 3.31 | 382 |
| 92 | Cl | O | | 2- | 3,5-difluorophenyl | 3.55 | 398 |
| 93 | F | O | | 2- | 3-isopropylphenyl | 4.30 | 388 |
| 94 | F | O | | 2- | 3-isopropylphenyl | 4.30 | 388 |
| 95 | Cl | O | | 2- | 3-isopropylphenyl | 4.76 | 404 |
| 96 | F | O | | 2- | 4-isopropylphenyl | 4.44 | 388 |
| 97 | Cl | O | | 2- | 4-isopropylphenyl | 4.86 | 404 |
| 98 | Cl | O | 4-fluoro | 2- | 4-chloro-3-fluorophenyl | 3.74 | |
| 99 | Cl | O | | 2- | 4-chloro-3-fluorophenyl | 3.71 | |
| 100 | F | O | | 2- | 4-chloro-3-fluorophenyl | 3.45 | |
| 101 | Cl | S | | 2- | 4-chloro-3-fluorophenyl | 3.92 | 430 |
| 102 | F | O | | 2- | 3-chloro-4-fluorophenyl | 3.60 | 398 |
| 103 | Cl | O | | 2- | 3-chloro-4-fluorophenyl | 3.85 | 414 |
| 104 | F | O | | 2- | 3,4,5-trifluorophenyl | 3.30 | |
| 105 | Cl | O | | 2- | 3,4,5-trifluorophenyl | 3.52 | |
| 106 | F | S | | 2- | 3,4,5-trifluorophenyl | 3.65 | 416 |
| 107 | F | O | | 2- | 2,4,5-trifluorophenyl | 3.25 | 400 |
| 108 | Cl | O | | 2- | 2,4,5-trifluorophenyl | 3.46 | 416 |
| 109 | F | O | | 2- | 4-tert-butylphenyl | 4.73 | 402 |
| 110 | Cl | O | | 2- | 4-tert-butylphenyl | 5.14 | 418 |
| 111 | F | O | | 2- | isopropoxyphenyl | 3.96 | 404 |
| 112 | Cl | O | | 2- | 3-isopropoxyphenyl | 4.36 | 420 |
| 113 | F | O | | 2- | 4-isopropoxyphenyl | 4.01 | 404 |
| 114 | Cl | O | | 2- | 4-isopropoxyphenyl | 4.36 | 420 |
| 115 | F | O | 6-fluoro | 2- | 3,4-dichlorophenyl | 3.50 | 432 |
| 116 | F | O | 4-fluoro | 2- | 3,4-dichlorophenyl | 3.89 | 432 |
| 117 | Cl | O | 4-fluoro | 2- | 3,4-dichlorophenyl | 4.04 | |
| 118 | F | O | 4-fluoro | 2- | 4-(trifluoromethyl)phenyl | 3.60 | |
| 119 | F | O | | 2- | 4-(trifluoromethyl)phenyl | 3.69 | 414 |
| 120 | Cl | O | | 2- | 4-(trifluoromethyl)phenyl | 3.94 | 430 |
| 121 | F | O | | 2- | 2,3-dichlorophenyl | 3.76 | 414 |
| 122 | Cl | O | | 2- | 2,3-dichlorophenyl | 4.06 | 430 |
| 123 | F | O | | 2- | 2,4-dichlorophenyl | 3.89 | 414 |
| 124 | Cl | O | | 2- | 2,4-dichlorophenyl | 4.24 | 430 |
| 125 | F | O | | 2- | 3,4-dichlorophenyl | 3.85 | 414 |
| 126 | Cl | O | | 2- | 3,4-dichlorophenyl | 4.14 | 430 |
| 127 | F | O | | 2- | 3,5-dichlorophenyl | 4.01 | 414 |
| 128 | Cl | O | | 2- | 3,5-dichlorophenyl | 4.31 | 430 |
| 129 | F | O | | 2- | 4-[(1E)-N-methoxy ethanimidoyl]phenyl | 3.78 | 417 |
| 130 | Cl | O | | 2- | 4-[(1E)-N-methoxy ethanimidoyl]phenyl | 4.11 | 433 |
| 131 | F | O | | 2- | 4-isobutoxyphenyl | 4.61 | 418 |
| 132 | Cl | O | | 2- | 3-(trimethoxysilyl)phenyl | 5.25 | 434 |
| 133 | F | O | | 2- | 3-(trimethylsilyl)phenyl | 4.83 | 418 |
| 134 | F | O | | 2- | 4-(trimethylsilyl)phenyl | 4.98 | 418 |
| 135 | Cl | O | | 2- | 4-isobutoxyphenyl | 4.96 | 434 |
| 136 | Cl | O | | 2- | 4-(trimethylsilyl)phenyl | 5.39 | 434 |
| 137 | F | O | | 2- | biphenyl-4-yl | 4.27 | |
| 138 | Cl | O | | 2- | biphenyl-4-yl | 4.61 | |
| 139 | F | O | | 2- | 4-bromophenyl | 3.56 | |
| 140 | Cl | O | | 2- | 4-bromophenyl | 3.88 | |
| 141 | Cl | S | | 2- | 4-bromophenyl | 3.96 | 456 |
| 142 | F | O | | 2- | 3-(trifluoromethoxy)phenyl | 3.83 | 430 |
| 143 | Cl | O | | 2- | 3-(trifluoromethoxy)phenyl | 4.11 | 446 |
| 144 | Cl | O | | 2- | 4-(trifluoromethoxy)phenyl | 4.19 | 446 |
| 145 | F | O | | 2- | 4-(trifluoromethoxy)phenyl | 3.92 | 430 |
| 146 | F | O | | 2- | 4-[(E)-(isopropoxy-imino)methyl]phenyl | 4.31 | 431 |
| 147 | Cl | O | | 2- | 4-[(E)-(isopropoxy-imino)methyl]phenyl | 4.63 | 447 |
| 148 | Cl | O | | 2- | 3-fluoro-4-(trifluoromethyl)phenyl | 3.77 | |
| 149 | F | O | | 2- | 3-fluoro-4-(trifluoromethyl)phenyl | 3.46 | |
| 150 | F | O | 4-fluoro | 2- | 3-fluoro-4-(trifluoromethyl)phenyl | 3.66 | |
| 151 | Cl | S | | 2- | 3-fluoro-4-(trifluoromethyl)phenyl | 4.06 | 464 |
| 152 | F | O | | 2- | 4-bromo-3-chlorophenyl | 3.83 | |
| 153 | Cl | O | | 2- | 4-bromo-3-chlorophenyl | 4.19 | |
| 154 | Cl | O | | 2- | 4-bromo-2-chlorophenyl | 4.16 | |
| 155 | F | O | | 2- | 4-bromo-2-chlorophenyl | 3.85 | |
| 156 | F | O | | 2- | 4-[(1E)-N-tert-butoxy ethanimidoyl]phenyl | 5.17 | 459 |
| 157 | Cl | O | | 2- | 4-[(1E)-N-tert-butoxy ethanimidoyl]phenyl | 5.54 | 475 |
| 158 | F | O | | 2- | benzyloxy | 3.67 | 376 |
| 159 | Cl | O | | 2- | benzyloxy | 3.99 | 392 |
| 160 | F | O | | 2- | 2-methylphenoxy | 3.96 | 376 |
| 161 | Cl | O | | 2- | 2-methylphenoxy | 4.29 | 392 |
| 162 | F | O | | 2- | (2,5-dichlorobenzyl)oxy | 4.56 | 444 |
| 163 | Cl | O | | 2- | (2,4-dichlorobenzyl)oxy | 4.81 | 460 |
| 164 | F | O | | 2- | (4-chlorophenyl)sulfanyl | 4.34 | 412 |
| 165 | Cl | O | | 2- | (4-chlorophenyl)sulfanyl | 4.63 | 428 |
| 166 | F | O | | 3- | isopropoxymethyl | 2.72 | |
| 167 | F | O | 4-ethoxy | 3- | ethoxy | 2.54 | 358 |
| 168 | Cl | O | 4-ethoxy | 3- | ethoxy | 2.70 | 374 |
| 169 | Cl | O | | 3- | isopropoxy | 2.98 | |
| 170 | F | O | | 3- | isopropoxy | 2.88 | 328 |
| 171 | Cl | S | | 3- | isopropoxy | 3.41 | 360 |
| 172 | F | O | 4,6-dichloro | 3- | isopropoxy | 4.41 | 396 |
| 173 | Cl | O | 4,6-dichloro | 3- | isopropoxy | 4.68 | 412 |
| 174 | Cl | O | | 3- | propoxy | 3.25 | 344 |
| 175 | F | O | | 3- | propoxy | 3.04 | 328 |
| 176 | F | O | | 3- | (2-methylprop-2-en-1-yl)oxy | 3.15 | 340 |

TABLE 1-continued

| Ex. | Hal | T | R¹ | position of Q | Q | logP | Mass (M+H) |
|---|---|---|---|---|---|---|---|
| 177 | Cl | O | | 3- | (2-methylprop-2-en-1-yl)oxy | 3.33 | 356 |
| 178 | Cl | O | 4-methyl | 3- | sec-butoxy | 4.06 | 372 |
| 179 | F | O | 4-methyl | 3- | sec-butoxy | 3.85 | 356 |
| 180 | F | O | | 3- | 2-methoxyethoxy | 2.15 | 344 |
| 181 | Cl | O | | 3- | trifluoromethoxy | 3.25 | |
| 182 | F | O | | 3- | 2,2-dimethylpropoxy | 3.96 | 356 |
| 183 | Cl | O | | 3- | 2,2-dimethylpropoxy | 4.19 | |
| 184 | Cl | O | 4-methyl | 3- | 2-ethoxyethoxy | 3.13 | 388 |
| 185 | F | O | 4-methyl | 3- | 2-ethoxyethoxy | 2.96 | 372 |
| 186 | F | O | | 3- | 2,2,2-trifluoroethoxy | 2.88 | 368 |
| 187 | Cl | O | | 3- | 2,2,2-trifluoroethoxy | 3.06 | 384 |
| 188 | Cl | O | | 3- | 1,1,2,2-tetrafluoroethoxy | 3.09 | |
| 189 | F | O | | 3- | bromo | 2.82 | 348 |
| 190 | Cl | O | | 3- | bromo | 3.04 | 364 |
| 191 | F | O | | 3- | cyclopropyl | 2.90 | 310 |
| 192 | F | O | | | 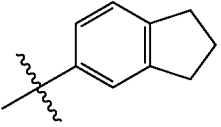 [SMILES: *c1ccc2c(c1)CCC2] | 2.96 | 310 |
| 193 | Cl | O | | | 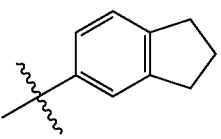 [SMILES: *c1ccc2c(c1)CCC2] | 3.17 | 326 |
| 194 | F | O | | | 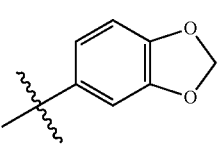 [SMILES: *c1ccc2c(c1)OCO2] | 2.05 | 314 |
| 195 | Cl | O | | | 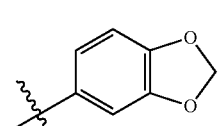 | 2.20 | 330 |
| 196 | F | O | | | 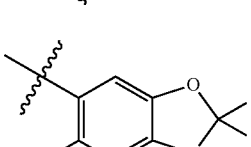 | 3.58 | 428 |
| 197 | F | O | | | 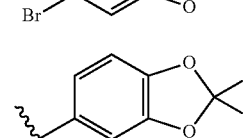 | 2.94 | 350 |
| 198 | Cl | O | | | 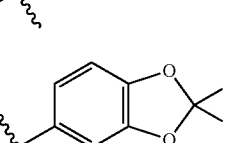 | 3.11 | 366 |
| 199 | F | O | | | 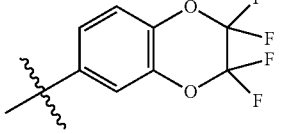 | 3.58 | 400 |
| 200 | Cl | O | | | 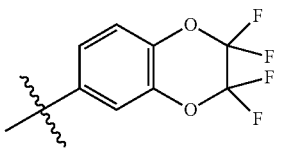 [SMILES: *c1ccc2c(c1)OC(F)(F)C(F)(F)O2] | 3.76 | 416 |
| 201 | F | O | | 3- | 2-methylphenyl | 3.63 | 360 |
| 202 | Cl | O | | 3- | 2-methylphenyl | 3.83 | 376 |
| 203 | F | O | | 3- | 4-fluorophenyl | 3.39 | 364 |
| 204 | Cl | O | | 3- | 4-fluorophenyl | 3.59 | 380 |
| 205 | F | O | | 3- | 3,5-dimethylphenyl | 4.11 | 374 |
| 206 | Cl | O | | 3- | 3,5-dimethylphenyl | 4.34 | 390 |
| 207 | F | O | | 3- | 4-chlorophenyl | 3.83 | 380 |
| 208 | Cl | O | | 3- | 4-chlorophenyl | 4.04 | 396 |
| 209 | F | O | | 3- | 3,5-difluorophenyl | 3.62 | 382 |
| 210 | Cl | O | | 3- | 3,5-difluorophenyl | 3.83 | 398 |
| 211 | F | O | | 3- | mesityl | 4.34 | 388 |
| 212 | Cl | O | | 3- | mesityl | 4.56 | 404 |
| 213 | Cl | O | | 3- | 3-isopropylphenyl | 4.61 | 404 |
| 214 | F | O | | 3- | 3-isopropylphenyl | 4.41 | 388 |
| 215 | F | O | | 3- | 4-isopropylphenyl | 4.46 | 388 |
| 216 | Cl | O | | 3- | 4-isopropylphenyl | 4.68 | 404 |
| 217 | F | O | | 3- | 3-chloro-4-fluorophenyl | 3.89 | 398 |
| 218 | Cl | O | | 3- | 3-chloro-4-fluorophenyl | 4.11 | 414 |
| 219 | F | O | | 3- | 4-tert-butylphenyl | 4.73 | 402 |
| 220 | Cl | O | | 3- | 4-tert-butylphenyl | 4.93 | 418 |
| 221 | F | O | | 3- | 3-isopropoxyphenyl | 3.99 | 404 |
| 222 | Cl | O | | 3- | isopropoxyphenyl | 4.21 | 420 |
| 223 | F | O | | 3- | 4-isopropoxyphenyl | 3.96 | 404 |
| 224 | Cl | O | | 3- | 4-isopropoxyphenyl | 4.19 | 420 |
| 225 | F | O | | 3- | 4-(trifluoromethyl)phenyl | 3.99 | 414 |
| 226 | Cl | O | | 3- | 4-(trifluoromethyl)phenyl | 4.19 | 430 |
| 227 | F | O | | 3- | 2,3-dichlorophenyl | 3.99 | 414 |
| 228 | Cl | O | | 3- | 2,3-dichlorophenyl | 4.21 | 430 |
| 229 | F | O | | 3- | 2,4-dichlorophenyl | 4.21 | 414 |
| 230 | Cl | O | | 3- | 2,4-dichlorophenyl | 4.39 | 430 |
| 231 | F | O | | 3- | 3,5-dichlorophenyl | 4.39 | 414 |
| 232 | Cl | O | | 3- | 3,5-dichlorophenyl | 4.73 | 430 |
| 233 | F | O | | 3- | 4-[(1E)-N-methoxyethanimidoyl]phenyl | 3.89 | 417 |
| 234 | Cl | O | | 3- | 4-[(1E)-N-methoxyethanimidoyl]phenyl | 4.11 | 433 |
| 235 | F | O | | 3- | 4-isobutoxyphenyl | 4.61 | 418 |
| 236 | Cl | O | | 3- | 4-isobutoxyphenyl | 4.83 | 434 |
| 237 | F | O | | 3- | 3-(trimethylsilyl)phenyl | 4.96 | 418 |
| 238 | Cl | O | | 3- | 3-(trimethylsilyl)phenyl | 5.17 | 434 |
| 239 | F | O | | 3- | 4-(trimethylsilyl)phenyl | 5.03 | 418 |
| 240 | Cl | O | | 3- | 4-(trimethylsilyl)phenyl | 5.25 | 434 |
| 241 | Cl | O | | 3- | 3-(trifluoromethoxy)phenyl | 4.31 | 446 |
| 242 | F | O | | 3- | 3-(trifluoromethoxy)phenyl | 4.11 | 430 |
| 243 | F | O | | 3- | 4-(trifluoromethoxy)phenyl | 4.14 | 430 |
| 244 | Cl | O | | 3- | 4-(trifluoromethoxy)phenyl | 4.34 | 446 |
| 245 | F | O | | 3- | 4-[(E)-(isopropoxyimino)methyl]phenyl | 4.46 | 431 |
| 246 | Cl | O | | 3- | 4-[(E)-(isopropoxyimino)methyl]phenyl | 4.66 | 447 |
| 247 | F | O | | 3- | 4-[(1E)-N-tert-butoxyethanimidoyl]phenyl | 5.28 | 459 |
| 248 | Cl | O | | 3- | 4-[(1E)-N-tert-butoxyethanimidoyl]phenyl | 5.51 | 475 |
| 249 | F | O | | 3- | phenylethynyl | 3.83 | 370 |
| 250 | F | O | | 3- | phenoxy | 3.35 | 362 |

TABLE 1-continued

| Ex. | Hal | T | R¹ | position of Q | Q | logP | Mass (M+H) |
|---|---|---|---|---|---|---|---|
| 251 | Cl | O | | 3- | phenoxy | 3.56 | 378 |
| 252 | F | O | | 3- | benzyloxy | 3.35 | 376 |
| 253 | Cl | O | | 3- | benzyloxy | 3.55 | 392 |
| 254 | F | O | | 3- | 4-chloro-2-methyl-phenoxy | 4.19 | 410 |
| 255 | Cl | O | | 3- | 3-(trifluoromethyl)-phenoxy | 3.89 | |
| 256 | Cl | O | | 3- | phenylsulfanyl | 3.85 | 394 |
| 257 | F | O | | 3- | phenylsulfanyl | 3.65 | 378 |
| 258 | F | O | | 3- | (4-tert-butylphenyl)sulfanyl | 4.98 | 434 |
| 259 | Cl | O | | 3- | (4-tert-butylphenyl)sulfanyl | 5.17 | 450 |
| 260 | F | O | 2-bromo | 4- | trifluoromethoxy | 3.76 | 432 |
| 261 | F | O | | 4- | chloro | 2.70 | 304 |
| 262 | F | O | | 4- | cyclohexyl | 4.21 | 352 |
| 263 | Cl | O | | 4- | cyclohexyl | 4.44 | 368 |
| 264 | F | O | | 4- | phenyl | 3.33 | 346 |
| 265 | Cl | O | | 4- | phenyl | 3.50 | 362 |
| 266 | F | O | | 4- | 3,5-dichlorophenyl | 4.51 | 414 |
| 267 | Cl | O | | 4- | 3,5-dichlorophenyl | 4.72 | 430 |
| 268 | F | O | | 4- | phenoxy | 3.29 | 362 |

In table 1, unless otherwise specified, M+H (ApcI+) means the molecular ion peak plus 1 a.m.u. (atomic mass unit) as observed in mass spectroscopy via positive atmospheric pressure chemical ionisation.

In table 1, the logP values were determined in accordance with EEC Directive 79/831 Annex V.A8 by HPLC (High Performance Liquid Chromatography) on a reversed-phase column (C 18), using the method described below:

Temperature: 40° C.; Mobile phases: 0.1% aqueous formic acid and acetonitrile; linear gradient from 10% acetonitrile to 90% acetonitrile.

Calibration was carried out using unbranched alkan-2-ones (comprising 3 to 16 carbon atoms) with known logP values (determination of the logP values by the retention times using linear interpolation between two successive alkanones). lambda-max-values were determined using UV-spectra from 200 nm to 400 nm and the peak values of the chromatographic signals.

NMR Data of Selected Examples

NMR Peak List Method

The $^1$H-NMR data of selected examples are stated in the form of $^1$H-NMR peak lists. For each signal peak, the δ value in ppm and the signal intensity in brackets are listed:

Example 7
Solvent: DMSO-d$_6$ 9.17 (0.68) 7.4152 (0.77) 7.4089 (0.8) 7.3959 (0.58) 7.3922 (0.94) 7.2585 (0.62) 7.2533 (0.49) 7.2499 (0.43) 7.2429 (0.93) 7.2373 (1.84) 7.2075 (0.39) 7.1949 (1.3) 7.189 (1.1) 7.1863 (1.5) 7.179 (2.89) 7.1704 (1.11) 7.1641 (0.9) 7.1028 (2.61) 6.9682 (1.3) 3.82 (5.25) 3.8184 (5.6) 3.1628 (2.02) 2.6131 (1.42) 2.5991 (0.8) 2.593 (1.48) 2.5868 (0.84) 2.5725 (1.51) 2.4962 (1.53) 2.4915 (3.18) 2.4868 (4.48) 2.4821 (3.14) 2.4774 (1.5) 1.9732 (0.99) 1.5728 (0.59) 1.5563 (0.78) 1.5398 (0.68) 1.5234 (0.4) 1.4572 (0.99) 1.4412 (1) 1.4368 (1.29) 1.4315 (0.67) 1.429 (0.58) 1.426 (0.5) 1.4212 (0.71) 1.4166 (1.33) 1.4002 (0.71) 1.1771 (0.56) 0.902 (0.49) 0.8933 (16) 0.8861 (0.83) 0.8769 (15.18) −0.0002 (0.89)

Example 20
Solvent: DMSO-d$_6$ 7.2566 (0.33) 7.2516 (0.53) 7.0922 (0.56) 3.8215 (1.36) 3.1139 (16) 2.497 (1.54) 2.4923 (3.1) 2.4876 (4.32) 2.4829 (3.04) 2.4783 (1.48) 1.4039 (1.25) 0.7981 (1.26) 0.7825 (1.26) 0.7787 (1.37) 0.7627 (1.09) 0.7547 (0.75) 0.7363 (1.47) 0.7178 (0.63)

Example 21
Solvent: DMSO-d$_6$ 7.3243 (0.32) 7.2542 (0.34) 7.2216 (0.32) 7.2179 (0.57) 7.0831 (0.69) 6.9485 (0.35) 3.8242 (1.55) 3.1099 (16) 2.4966 (1.63) 2.4919 (3.38) 2.4872 (4.79) 2.4825 (3.36) 2.4778 (1.61) 1.404 (0.8) 1.1724 (1.75) 1.1552 (1.73) 0.7641 (11.7) −0.0002 (0.49)

Example 47
Solvent: DMSO-d$_6$ 3.8241 (1.06) 3.1861 (16) 2.4035 (1.2) 2.399 (2.44) 2.3944 (3.3) 2.3898 (2.33) 2.3853 (1.09)

Example 48
Solvent: DMSO-d$_6$ 9.1452 (1.96) 7.9118 (1.8) 7.8939 (1.74) 7.3808 (1.61) 7.2776 (1.57) 7.2573 (2.47) 7.2463 (3.77) 7.2363 (1.91) 7.2171 (1.16) 7.1689 (0.47) 7.1568 (0.37) 7.1528 (0.36) 7.1393 (1.55) 7.1369 (1.62) 7.1209 (2.13) 7.1179 (2.21) 7.1119 (1.93) 7.1023 (0.86) 7.0993 (0.8) 3.9369 (16) 3.9289 (2.51) 3.3502 (0.38) 3.3449 (0.39) 3.2889 (469.82) 2.6726 (0.59) 2.6681 (0.84) 2.6633 (0.6) 2.538 (1.72) 2.5213 (2.68) 2.508 (45.02) 2.5034 (90.3) 2.4989 (121.97) 2.4943 (85.88) 2.4898 (39.6) 2.3304 (0.54) 2.3256 (0.77) 2.3209 (0.52) 2.1463 (0.54) 2.1255 (1.12) 2.1101 (1.18) 2.0888 (0.58) 2.067 (6.46) 1.2371 (0.33) 1.0633 (0.43) 1.0565 (0.59) 1.0425 (1.03) 1.0281 (0.7) 1.021 (0.68) 1.0062 (0.38) 0.986 (0.95) 0.974 (1.21) 0.9648 (1.53) 0.9529 (1.74) 0.9436 (0.64) 0.9316 (0.66) 0.8315 (0.87) 0.818 (1.95) 0.8128 (1.18) 0.8047 (1.72) 0.7913 (0.65) 0.7361 (0.41) 0.7177 (0.48) 0.343 (0.32) 0.2205 (0.54) 0.2143 (0.51) 0.2012 (0.67) 0.1957 (1.27) 0.191 (0.79) 0.1846 (1.02) 0.1777 (0.72) 0.1722 (0.83) 0.166 (0.72) 0.1108 (1.6) 0.0993 (2.19) 0.0875 (1.35) 0.0757 (1.6) 0.0697 (0.99) 0.0556 (1.04) 0.0475 (0.71) 0.0366 (0.96) 0.0316 (1.69) 0.0249 (4.06) 0.0133 (2.5) −0.0002 (10.98) −0.0086 (0.47)

Example 51
Solvent: DMSO-d$_6$ 7.3881 (0.34) 7.3824 (0.32) 7.2949 (0.35) 7.2422 (0.4) 7.2094 (0.38) 7.2046 (0.35) 7.1975 (0.39) 7.1914 (0.56) 7.1792 (0.35) 7.1076 (0.87) 6.973 (0.42) 3.8262 (1.77) 3.8245 (1.9) 3.1108 (16)

-continued 2.4965 (1.77) 2.4918 (3.65) 2.4871 (5.14) 2.4824 (3.6) 2.4777 (1.73) 2.3221 (0.34) 1.5419 (0.33)
1.4961 (0.35) 1.4038 (2.61) −0.0002 (0.45)
Example 64
Solvent: DMSO-$d_6$ 7.1014 (0.44) 3.817 (0.87) 3.8155 (0.94) 3.1159 (16) 2.4972 (1.18) 2.4925 (2.45) 2.4878 (3.46)
2.4831 (2.41) 2.4783 (1.15) 1.31 (1.86) 1.1947 (1.17) 1.1831 (1.84) 1.1774 (1.24)
Example 83
Solvent: $CD_3CN$ 8.0192 (1.27) 7.9626 (1.29) 7.9536 (1.49) 7.9478 (1.47) 7.9389 (1.23) 7.4808 (3.8) 7.4671 (5.62)
7.4168 (5.8) 7.403 (3.73) 7.2059 (0.88) 7.2009 (1) 7.1916 (1.63) 7.1867 (1.67) 7.1773 (0.89) 7.1725
(0.85) 7.1461 (1.28) 7.1352 (1.86) 7.1303 (1.57) 7.1199 (1.83) 7.1151 (1.44) 7.0566 (2.3) 6.9673
(1.15) 3.9226 (0.39) 3.8193 (16) 2.1506 (4.77) 1.9652 (2.84) 1.9484 (20.37) 1.9448 (32.12) 1.9409
(40.18) 1.937 (28.45) 1.933 (15.11) −0.0002 (35.82) −0.0062 (4.1)
Example 84
Solvent: $CD_3CN$ 7.9044 (2.06) 7.8908 (2.16) 7.8822 (2.28) 7.8685 (2.22) 7.7972 (1.22) 7.7232 (0.32) 7.6789 (0.33)
7.5068 (0.36) 7.4865 (0.95) 7.481 (5.51) 7.4757 (2.47) 7.4648 (3.51) 7.4593 (11.86) 7.4538 (2.17)
7.4429 (0.49) 7.4249 (2.16) 7.4193 (11.75) 7.4139 (3.34) 7.403 (2.43) 7.3977 (5.56) 7.392 (0.84)
7.2259 (0.34) 7.2033 (0.49) 7.1987 (1.47) 7.1911 (1.87) 7.1776 (2.18) 7.1697 (3.04) 7.1581 (3.16)
7.1481 (5.06) 7.1407 (2.38) 7.1248 (3.3) 7.1174 (2.28) 7.0237 (5.4) 6.8892 (2.72) 3.8081 (0.51)
3.7227 (15.17) 3.7211 (16) 3.7195 (15.12) 3.6934 (0.68) 3.4188 (0.4) 2.1534 (124.66) 2.1192 (0.48)
2.1126 (0.43) 2.1064 (0.44) 2.1002 (0.33) 1.971 (1.81) 1.9633 (21.79) 1.9572 (3.05) 1.9514 (16.88)
1.9452 (31.19) 1.939 (43.59) 1.9328 (29.79) 1.9267 (15.11) 1.4366 (1.47) 1.2035 (0.54) −0.0002
(2.66)
Example 99
Solvent: DMSO-$d_6$ 9.6517 (0.69) 7.9518 (2.2) 7.6275 (0.42) 7.6072 (0.82) 7.5869 (0.48) 7.5687 (0.46) 7.5494 (0.63)
7.4665 (0.4) 7.4588 (0.76) 7.4534 (0.6) 7.4467 (0.33) 7.4403 (0.37) 7.4319 (0.52) 7.4271 (0.52)
7.3919 (1.2) 7.3878 (1.17) 7.375 (0.46) 7.3723 (0.43) 7.2808 (0.47) 7.2768 (0.45) 7.2602 (0.42)
7.2562 (0.4) 6.9797 (0.63) 3.8689 (3.58) 3.3104 (38.74) 2.8902 (16) 2.7316 (13.48) 2.5395 (0.33)
2.5046 (5.58) 2.5004 (6.79) 2.4963 (4.77)
Example 100
Solvent: DMSO-$d_6$ 9.5007 (3.42) 7.6265 (2.91) 7.6062 (5.78) 7.5983 (2.67) 7.5859 (3.72) 7.5791 (3.26) 7.4753 (1.95)
7.471 (3.51) 7.467 (3.21) 7.4586 (2.49) 7.453 (2.98) 7.4504 (2.16) 7.4454 (3.04) 7.4399 (3.63)
7.4333 (2.52) 7.4192 (1.13) 7.4141 (1.84) 7.4002 (5.45) 7.3948 (4.45) 7.3915 (4.57) 7.3884 (4.22)
7.3744 (2.61) 7.3716 (2.82) 7.3553 (0.9) 7.3522 (0.86) 7.2805 (2.63) 7.2767 (2.67) 7.2598 (2.4)
7.2559 (2.47) 7.1409 (1.71) 7.0067 (3.75) 6.8725 (1.84) 3.8703 (0.36) 3.7784 (16) 3.3787 (207.86)
3.3662 (305.43) 3.3031 (0.91) 2.8584 (1.76) 2.8451 (1.71) 2.6736 (0.37) 2.5435 (0.32) 2.5266 (1.12)
2.5135 (22.04) 2.509 (44.66) 2.5044 (59.48) 2.4998 (43.05) 2.4952 (20.84) 2.3312 (0.37) 2.0721
(0.74) 1.9888 (0.89) 1.3974 (7.13) 1.2353 (0.41) 1.175 (0.52) 0.008 (0.48) −0.0002 (12) −0.0085
(0.42)
Example 104
Solvent: DMSO-$d_6$ 9.4875 (3.76) 7.6262 (2.62) 7.6065 (3.27) 7.4835 (1.4) 7.4784 (1.62) 7.466 (2.27) 7.4612 (2.61)
7.4464 (1.62) 7.4414 (1.9) 7.4195 (1.55) 7.4146 (2.02) 7.4004 (5.35) 7.3956 (4.41) 7.3842 (5.56)
7.3662 (5.64) 7.3602 (4.01) 7.3481 (2.3) 7.3429 (3.3) 7.1458 (1.96) 7.0115 (4.18) 6.8773 (2.07)
4.0568 (0.34) 4.039 (0.98) 4.0212 (0.95) 4.0036 (0.39) 3.8755 (0.79) 3.8351 (0.66) 3.7821 (16)
3.3075 (667.45) 3.1916 (0.34) 3.1788 (0.32) 2.6737 (0.78) 2.669 (0.96) 2.6646 (0.75) 2.5392 (3.16)
2.5043 (93.24) 2.5001 (114.34) 2.496 (80.71) 2.3354 (0.44) 2.3314 (0.64) 2.3267 (0.82) 2.069 (0.41)
1.9865 (3.87) 1.1927 (1.05) 1.1749 (2.1) 1.1571 (1.03) −0.0002 (3.74)
Example 148
Solvent: DMSO-$d_6$ 9.7687 (2.75) 7.8144 (1.19) 7.7946 (2.46) 7.7748 (1.34) 7.6797 (0.43) 7.5523 (1.24) 7.5418 (2.1)
7.5356 (3.31) 7.5324 (3.04) 7.523 (1.75) 7.5174 (2.45) 7.5121 (2.08) 7.507 (2.29) 7.5016 (2.2)
7.4867 (0.82) 7.4816 (1.07) 7.4542 (3.1) 7.4395 (3.79) 7.4345 (4.58) 7.4317 (4.44) 7.4279 (2.94)
7.4153 (1.71) 7.4116 (1.88) 7.396 (0.61) 7.3921 (0.61) 7.0802 (1.5) 6.9457 (3.11) 6.8112 (1.53)
4.0404 (0.51) 4.0226 (0.44) 3.8654 (16) 3.2999 (176.57) 2.5388 (0.33) 2.5221 (0.54) 2.5089 (9.51)
2.5043 (19.03) 2.4998 (25.61) 2.4952 (18.11) 2.4907 (8.45) 1.986 (1.9) 1.3985 (15.78) 1.1933 (0.53)
1.1755 (1.05) 1.1577 (0.52) −0.0002 (0.53)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

The $^1$H-NMR peak lists are similar to classical $^1$H-NMR prints and contain therefore usually all peaks, which are listed at classical NMR-interpretation. Additionally they can show like classical $^1$H-NMR prints signals of solvents, stereoisomers of the target compounds, which are also object of the invention, and/or peaks of impurities. To show compound signals in the delta-range of solvents and/or water the usual peaks of solvents, for example peaks of DMSO in DMSO-d6 and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%). Such stereoisomers and/or impurities can be typical for the specific preparation process. Therefore their peaks can help to recognize the reproduction of our preparation process via "side-products-fingerprints". An expert, who calculates the peaks of the target compounds with known methods (MestreC, ACD-simulation, but also with empirically evaluated expectation values), can isolate the peaks of the target compounds as needed optionally using additional intensity filters. This isolation would be similar to relevant peak picking at classical $^1$H-NMR interpretation.

USE EXAMPLES

Example A

*Alternaria* Test (Tomato)/Preventive

Solvent: 49 parts by weight of N,N-dimethylformamide
Emulsifier: 1 part by weight of alkylarylpolyglycolether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. One day after this treatment, the plants are inoculated with an aqueous spore suspension of *Alternaria solani*. The plants remain for one day in an incubation cabinet at approximately 22° C. and a relative atmospheric humidity of 100%. Then the plants are placed in an incubation cabinet at approximately 20° C. and a relative atmospheric humidity of 96%.

The test is evaluated 7 days after the inoculation. 0% means an efficacy which corresponds to that of the untreated control while an efficacy of 100% means that no disease is observed.

In this test, the following compounds from table A according to the invention, show at an active compound concentration of 500 ppm, an efficacy of 70% or more:

TABLE A

| Example | Efficacy |
|---------|----------|
| 3 | 94 |
| 7 | 95 |
| 8 | 95 |
| 9 | 95 |
| 11 | 100 |
| 13 | 100 |
| 19 | 80 |
| 20 | 90 |
| 21 | 95 |
| 23 | 70 |
| 28 | 70 |
| 31 | 100 |
| 32 | 95 |
| 46 | 100 |
| 51 | 95 |
| 53 | 100 |
| 54 | 70 |
| 64 | 95 |
| 65 | 80 |
| 66 | 100 |
| 68 | 80 |
| 70 | 78 |
| 71 | 80 |
| 72 | 70 |
| 73 | 90 |
| 74 | 78 |
| 75 | 94 |
| 77 | 95 |
| 78 | 90 |
| 79 | 90 |
| 80 | 95 |
| 83 | 94 |
| 84 | 94 |
| 85 | 95 |
| 86 | 95 |
| 87 | 95 |
| 88 | 94 |
| 89 | 94 |
| 90 | 90 |
| 100 | 80 |
| 101 | 80 |
| 106 | 90 |
| 107 | 100 |
| 108 | 100 |
| 115 | 95 |
| 116 | 100 |
| 118 | 100 |
| 125 | 95 |
| 126 | 89 |
| 137 | 95 |
| 141 | 70 |
| 149 | 100 |
| 150 | 89 |
| 151 | 95 |
| 152 | 94 |
| 153 | 90 |
| 154 | 95 |
| 155 | 95 |
| 174 | 70 |
| 254 | 70 |

Example B

*Sphaerotheca* Test (Cucumber)/Preventive

Solvent: 49 parts by weight of N,N-dimethylformamide
Emulsifier: 1 part by weight of alkylarylpolyglycolether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. One day after this treatment, the plants are inoculated with an aqueous spore suspension of *Sphaerotheca fuliginea*. Then the plants are placed in a greenhouse at approximately 23° C. and a relative atmospheric humidity of approximately 70%.

The test is evaluated 7 days after the inoculation. 0% means an efficacy which corresponds to that of the untreated control, while an efficacy of 100% means that no disease is observed.

In this test, the following compounds from table B according to the invention, show at an active compound concentration of 500 ppm, an efficacy of 75% or more:

TABLE B

| Example | Efficacy |
|---------|----------|
| 3 | 98 |
| 9 | 100 |
| 11 | 100 |
| 13 | 100 |
| 21 | 95 |
| 31 | 91 |
| 46 | 94 |
| 51 | 96 |
| 53 | 100 |

TABLE B-continued

| Example | Efficacy |
|---|---|
| 64 | 100 |
| 66 | 100 |
| 68 | 98 |
| 69 | 98 |
| 70 | 90 |
| 71 | 100 |
| 72 | 100 |
| 73 | 75 |
| 77 | 95 |
| 78 | 75 |
| 79 | 95 |
| 80 | 98 |
| 83 | 100 |
| 85 | 98 |
| 87 | 95 |
| 88 | 100 |
| 89 | 100 |
| 90 | 95 |
| 100 | 100 |
| 101 | 95 |
| 106 | 98 |
| 107 | 88 |
| 108 | 93 |
| 116 | 98 |
| 118 | 100 |
| 125 | 98 |
| 126 | 100 |
| 137 | 100 |
| 138 | 100 |
| 141 | 95 |
| 149 | 100 |
| 150 | 100 |
| 151 | 98 |
| 152 | 95 |
| 153 | 100 |
| 154 | 100 |

Example C

*Venturia* Test (Apples)/Preventive

Solvent: 24.5 parts by weight of acetone 24.5 parts by weight of N,N-dimethylformamide Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous conidia suspension of the causal agent of apple scab (*Venturia inaequalis*) and then remain for 1 day in an incubation cabinet at approximately 20° C. and a relative atmospheric humidity of 100%.

The plants are then placed in a greenhouse at approximately 21° C. and a relative atmospheric humidity of approximately 90%.

The test is evaluated 10 days after the inoculation. 0% means an efficacy which corresponds to that of the untreated control, while an efficacy of 100% means that no disease is observed.

In this test, the following compounds from table C according to the invention, show at an active compound concentration of 100 ppm, an efficacy of 75% or more:

TABLE C

| Example | Efficacy |
|---|---|
| 8 | 100 |
| 9 | 100 |
| 11 | 100 |
| 12 | 100 |
| 13 | 100 |
| 14 | 100 |
| 21 | 100 |
| 22 | 100 |
| 23 | 100 |
| 24 | 100 |
| 28 | 100 |
| 46 | 100 |
| 47 | 100 |
| 48 | 100 |
| 51 | 100 |
| 53 | 100 |
| 64 | 99 |
| 65 | 98 |
| 66 | 100 |
| 67 | 100 |
| 68 | 98 |
| 69 | 100 |
| 71 | 100 |
| 72 | 100 |
| 83 | 100 |
| 84 | 100 |
| 85 | 100 |
| 86 | 100 |
| 88 | 100 |
| 89 | 100 |
| 98 | 100 |
| 99 | 100 |
| 100 | 99 |
| 104 | 100 |
| 105 | 100 |
| 106 | 100 |
| 108 | 100 |
| 115 | 100 |
| 116 | 100 |
| 117 | 100 |
| 118 | 100 |
| 125 | 100 |
| 126 | 75 |
| 137 | 100 |
| 139 | 100 |
| 140 | 100 |
| 148 | 100 |
| 149 | 100 |
| 150 | 100 |
| 152 | 100 |
| 153 | 95 |
| 154 | 100 |
| 155 | 100 |
| 169 | 96 |

Example D

*Uromyces* Test (Beans)/Preventive

Solvent: 24.5 parts by weight of acetone 24.5 parts by weight of N,N-dimethylformamide Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous spore suspension of the causal agent of bean rust (*Uromyces appendiculatus*) and then remain for 1 day in an incubation cabinet at approximately 20° C. and a relative atmospheric humidity of 100%.

The plants are then placed in a greenhouse at approximately 21° C. and a relative atmospheric humidity of approximately 90%.

The test is evaluated 10 days after the inoculation. 0% means an efficacy which corresponds to that of the untreated control, while an efficacy of 100% means that no disease is observed.

In this test, the following compounds from table D according to the invention, show at an active compound concentration of 100 ppm, an efficacy of 70% or more:

TABLE D

| Example | Efficacy |
|---|---|
| 8 | 100 |
| 9 | 100 |
| 11 | 100 |
| 12 | 100 |
| 13 | 100 |
| 14 | 100 |
| 21 | 100 |
| 22 | 100 |
| 23 | 90 |
| 24 | 100 |
| 28 | 94 |
| 46 | 100 |
| 47 | 100 |
| 48 | 100 |
| 51 | 100 |
| 53 | 100 |
| 64 | 100 |
| 65 | 100 |
| 66 | 100 |
| 67 | 100 |
| 68 | 100 |
| 69 | 95 |
| 71 | 100 |
| 72 | 100 |
| 83 | 100 |
| 84 | 99 |
| 85 | 100 |
| 86 | 100 |
| 88 | 100 |
| 89 | 100 |
| 98 | 100 |
| 99 | 100 |
| 100 | 99 |
| 104 | 100 |
| 105 | 100 |
| 106 | 100 |
| 108 | 100 |
| 115 | 100 |
| 116 | 100 |
| 117 | 100 |
| 118 | 95 |
| 125 | 100 |
| 126 | 96 |
| 137 | 99 |
| 139 | 100 |
| 140 | 100 |
| 148 | 100 |
| 148 | 100 |
| 149 | 100 |
| 150 | 98 |
| 152 | 100 |
| 153 | 100 |
| 154 | 100 |
| 155 | 100 |
| 169 | 100 |
| 181 | 100 |
| 188 | 100 |
| 255 | 73 |

Under the same conditions, total protection is observed at a dose of 100 ppm with compounds 104 and 105, whereas 100% of plant damages is observed with the compound of example 9.12 disclosed in patent application WO-2006/087343 as in table D2.

TABLE D2

| Example | dose (ppm) | Efficacy |
|---|---|---|
| 104 from this invention | 100 | 100 |
| 105 from this invention | 100 | 100 |
| 9.12 from WO-2006/087343 | 100 | —[a] | note
[a]100% of plant damages

Example 9.12 disclosed in international patent WO-2006/087343 corresponds to 3-(difluoromethyl)-1-methyl-N-(3',4',5'-trifluorobiphenyl-2-yl)-1H-pyrazole-4-carboxamide [commun name: fluxapyroxad].

These results show that the compounds according to the invention have a better biological activity than the structurally closest compounds disclosed in WO-2006/087343.

Example E

Botrytis Test (Beans)/Preventive

Solvent: 24.5 parts by weight of acetone
24.5 parts by weight of N,N-dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound. After the spray coating has dried on, 2 small pieces of agar covered with growth of Botrytis cinerea are placed on each leaf. The inoculated plants are placed in a darkened chamber at 20° C. and a relative atmospheric humidity of 100%.

2 days after the inoculation, the size of the lesions on the leaves is evaluated. 0% means an efficacy which corresponds to that of the untreated control, while an efficacy of 100% means that no disease is observed.

In this test, the following compounds from table E according to the invention, show at an active compound concentration of 100 ppm, an efficacy of 75% or more:

TABLE E

| Example | Efficacy |
|---|---|
| 8 | 98 |
| 11 | 95 |
| 12 | 99 |
| 13 | 94 |
| 14 | 99 |
| 21 | 100 |
| 22 | 100 |
| 24 | 78 |
| 46 | 99 |
| 51 | 100 |
| 53 | 94 |
| 64 | 95 |
| 66 | 99 |
| 67 | 99 |
| 68 | 91 |
| 69 | 100 |
| 71 | 94 |
| 72 | 100 |
| 83 | 100 |
| 84 | 99 |
| 85 | 100 |
| 86 | 100 |
| 88 | 92 |
| 89 | 100 |
| 98 | 100 |
| 99 | 97 |

TABLE E-continued

| Example | Efficacy |
|---|---|
| 100 | 99 |
| 104 | 100 |
| 105 | 100 |
| 108 | 99 |
| 115 | 94 |
| 116 | 100 |
| 117 | 99 |
| 118 | 100 |
| 125 | 100 |
| 139 | 100 |
| 140 | 98 |
| 148 | 100 |
| 149 | 99 |
| 150 | 100 |
| 152 | 100 |
| 153 | 75 |
| 154 | 78 |
| 155 | 100 |

Example F

*Fusarium Nivale* (Var. *Majus*)-Test (Wheat)/Preventive

Solvent: 49 parts by weight of N,N-dimethylacetamide
Emulsifier: 1 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application.

After the spray coating has been dried, the plants are slightly injured by using a sandblast and afterwards they are sprayed with a conidia suspension of *Fusarium nivale* (var. *majus*).

The plants are placed in the greenhouse under a translucent incubation cabinet at a temperature of approximately 10° C. and a relative atmospheric humidity of approximately 100%.

The test is evaluated 5 days after the inoculation. 0% means an efficacy which corresponds to that of the untreated control, while an efficacy of 100% means that no disease is observed.

In this test, the following compounds from table F according to the invention, show at an active compound concentration of 500 ppm, an efficacy of 70% or more:

TABLE F

| Example | Efficacy |
|---|---|
| 9 | 100 |
| 12 | 86 |
| 13 | 100 |
| 14 | 100 |
| 22 | 86 |
| 24 | 86 |
| 25 | 88 |
| 47 | 86 |
| 48 | 86 |
| 55 | 83 |
| 64 | 75 |
| 65 | 86 |
| 66 | 86 |
| 67 | 100 |
| 68 | 93 |
| 71 | 94 |

TABLE F-continued

| Example | Efficacy |
|---|---|
| 72 | 100 |
| 85 | 100 |
| 86 | 71 |
| 88 | 100 |
| 89 | 100 |
| 98 | 86 |
| 99 | 100 |
| 100 | 90 |
| 101 | 100 |
| 105 | 100 |
| 115 | 86 |
| 118 | 71 |
| 126 | 100 |
| 139 | 93 |
| 140 | 86 |
| 148 | 86 |
| 149 | 93 |
| 150 | 86 |
| 151 | 100 |
| 152 | 100 |
| 153 | 93 |
| 169 | 71 |
| 170 | 86 |
| 176 | 100 |
| 193 | 75 |
| 208 | 100 |
| 212 | 75 |
| 255 | 100 |

Under the same conditions, good (at least 70%) protection to total protection is observed at a dose of 250 ppm and 500 ppm of active ingredient with compounds 66 and 67, whereas average (less than 50%) protection to good (at least 70%) protection is observed with the compound of example 15.202 disclosed in patent application WO-2004/035589 as in table F2.

TABLE F2

| Example | dose (ppm) | Efficacy |
|---|---|---|
| 66 from this invention | 500 | 86 |
|  | 250 | 93 |
| 67 from this invention | 500 | 100 |
|  | 250 | 71 |
| 15.202 (syn/anti 9/1) from WO-2004/035589 | 500 | 50 |
|  | 250 | 50 |
| 15.202 (syn/anti 3/7) from WO-2004/035589 | 500 | 83 |
|  | 250 | 50 |

Example 15.202 disclosed in international patent WO-2004/035589 corresponds to 3-(difluoromethyl)-N-(9-isopropyl-1,2,3,4-tetrahydro-1,4-methanonaphthalen-5-yl)-1-methyl-1H-pyrazole-4-carboxamide [commun name: isopyrazam].

These results show that the compounds according to the invention have a better biological activity than the structurally closest compounds disclosed in WO-2004/035589.

Under the same conditions, excellent (at least 94%) protection to total protection is observed at a dose of 250 ppm and 500 ppm of active ingredient with compounds 71 and 72, whereas good (at least 70%) protection is observed with the compound of example A1.1 disclosed in patent application WO-2008/131901 as in table F3.

TABLE F3

| Example | dose (ppm) | Efficacy |
|---|---|---|
| 71 from this invention | 500 | 94 |
|  | 250 | 94 |
| 72 from this invention | 500 | 100 |
|  | 250 | 100 |
| A1.1 from WO-2008/131901 | 500 | 88 |
|  | 250 | 75 |

Example A1.1 disclosed in international patent WO-2008/131901 corresponds to N-[9-(dichloromethylene)-1,2,3,4-tetrahydro-1,4-methanonaphthalen-5-yl]-3-(difluoromethyl)-1-methyl-1H-pyrazole-4-carboxamide [commun name: hambra].

These results show that the compounds according to the invention have a better biological activity than the structurally closest compounds disclosed in WO-2008/131901.

Under the same conditions, good (at least 70%) protection to high (at least 85%) protection is observed at a dose of 250 ppm and 500 ppm of active ingredient with compound 12, whereas poor (less than 40%) protection is observed with the compound of example 1-21 disclosed in patent application WO-2003/010149 as in table F4.

TABLE F4

| Example | dose (ppm) | Efficacy |
|---|---|---|
| 12 from this invention | 500 | 86 |
|  | 250 | 71 |
| I-21 from WO-2003/010149 | 500 | 40 |
|  | 250 | 20 |

Example I-21 disclosed in international patent WO-2003/010149 corresponds to 5-fluoro-1,3-dimethyl-N-[2-(4-methylpentan-2-yl)phenyl]-1H-pyrazole-4-carboxamide [commun name: penflufen].

These results show that the compounds according to the invention have a better biological activity than the structurally closest compounds disclosed in WO-2003/010149.

Under the same conditions, high (at least 85%) protection is observed at a dose of 500 ppm of active ingredient with compounds 47 and 48, whereas average (less than 60%) protection is observed with the compound of example 2.34 disclosed in patent application WO-2003/074491 as in table F5.

TABLE F5

| Example | dose (ppm) | Efficacy |
|---|---|---|
| 47 from this invention | 500 | 86 |
| 48 from this invention | 500 | 86 |
| 2.34 from WO-2003/074491 | 500 | 57 |

Example 2.34 disclosed in international patent WO-2003/074491 corresponds to N-{2-[1,1'-bi(cyclopropyl)-2-yl]phenyl}-3-(difluoromethyl)-1-methyl-1H-pyrazole-4-carboxamide [commun name: sedaxane].

These results show that the compounds according to the invention have a better biological activity than the structurally closest compounds disclosed in WO-2003/074491.

Example G

*Puccinia* Triticina-Test (Wheat)/Preventive

Solvent: 49 parts by weight of N,N-dimethylacetamide
Emulsifier: 1 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application.

After the spray coating has been dried, the plants are sprayed with a spore suspension of *Puccinia triticina*. The plants remain for 48 hours in an incubation cabinet at approximately 20° C. and a relative atmospheric humidity of approximately 100%.

The plants are placed in the greenhouse at a temperature of approximately 20° C. and a relative atmospheric humidity of approximately 80%.

The test is evaluated 8 days after the inoculation. 0% means an efficacy which corresponds to that of the untreated control, while an efficacy of 100% means that no disease is observed.

In this test, the following compounds from table G according to the invention, show at an active compound concentration of 500 ppm, an efficacy of 70% or more:

TABLE G

| Example | Efficacy |
|---|---|
| 7 | 100 |
| 8 | 100 |
| 9 | 100 |
| 11 | 100 |
| 12 | 100 |
| 13 | 100 |
| 14 | 100 |
| 21 | 100 |
| 22 | 100 |
| 23 | 100 |
| 24 | 100 |
| 25 | 100 |
| 28 | 100 |
| 46 | 100 |
| 47 | 100 |
| 48 | 100 |
| 51 | 71 |
| 55 | 100 |
| 64 | 100 |
| 65 | 100 |
| 66 | 100 |
| 67 | 100 |
| 68 | 100 |
| 69 | 100 |
| 71 | 100 |
| 72 | 94 |
| 75 | 70 |
| 85 | 100 |
| 86 | 100 |
| 88 | 100 |
| 89 | 100 |
| 90 | 100 |
| 98 | 100 |
| 99 | 100 |
| 100 | 100 |
| 101 | 100 |
| 104 | 100 |
| 105 | 100 |
| 106 | 100 |
| 115 | 88 |
| 116 | 100 |
| 117 | 100 |
| 118 | 100 |
| 125 | 100 |
| 126 | 100 |
| 137 | 100 |
| 138 | 100 |
| 139 | 100 |
| 140 | 100 |

TABLE G-continued

| Example | Efficacy |
|---|---|
| 148 | 100 |
| 149 | 100 |
| 150 | 100 |
| 151 | 100 |
| 152 | 100 |
| 153 | 100 |
| 163 | 71 |
| 169 | 100 |
| 170 | 100 |
| 176 | 100 |
| 188 | 100 |
| 193 | 100 |
| 208 | 100 |
| 212 | 86 |
| 255 | 94 |

Example H

Pyrenophora Teres-Test (Barley)/Preventive

Solvent: 49 parts by weight of N,N-dimethylacetamide
Emulsifier: 1 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application.

After the spray coating has been dried, the plants are sprayed with a spore suspension of Pyrenophora teres. The plants remain for 48 hours in an incubation cabinet at approximately 20° C. and a relative atmospheric humidity of approximately 100%.

The plants are placed in the greenhouse at a temperature of approximately 20° C. and a relative atmospheric humidity of approximately 80%.

The test is evaluated 8 days after the inoculation. 0% means an efficacy which corresponds to that of the untreated control, while an efficacy of 100% means that no disease is observed.

In this test, the following compounds from table H according to the invention, show at an active compound concentration of 500 ppm, an efficacy of 70% or more:

TABLE H

| Example | Efficacy |
|---|---|
| 7 | 100 |
| 8 | 100 |
| 9 | 100 |
| 11 | 100 |
| 12 | 100 |
| 13 | 100 |
| 14 | 100 |
| 21 | 95 |
| 22 | 100 |
| 23 | 71 |
| 24 | 86 |
| 28 | 71 |
| 46 | 100 |
| 47 | 100 |
| 48 | 86 |
| 51 | 100 |
| 55 | 71 |
| 64 | 100 |
| 65 | 100 |
| 66 | 100 |
| 67 | 100 |
| 68 | 100 |
| 69 | 100 |
| 71 | 100 |
| 72 | 100 |
| 75 | 100 |
| 85 | 100 |
| 86 | 100 |
| 88 | 100 |
| 89 | 100 |
| 90 | 100 |
| 98 | 100 |
| 99 | 100 |
| 100 | 100 |
| 101 | 100 |
| 104 | 100 |
| 105 | 100 |
| 106 | 100 |
| 116 | 100 |
| 117 | 100 |
| 118 | 100 |
| 125 | 100 |
| 126 | 100 |
| 137 | 93 |
| 138 | 86 |
| 139 | 100 |
| 140 | 100 |
| 148 | 100 |
| 149 | 100 |
| 150 | 100 |
| 151 | 100 |
| 152 | 100 |
| 153 | 100 |
| 163 | 92 |
| 169 | 100 |
| 176 | 100 |
| 188 | 92 |
| 208 | 100 |

Example I

Septoria Tritici-Test (Wheat)/Preventive

Solvent: 49 parts by weight of N,N-dimethylacetamide
Emulsifier: 1 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application.

After the spray coating has been dried, the plants are sprayed with a spore suspension of Septoria tritici. The plants remain for 48 hours in an incubation cabinet at approximately 20° C. and a relative atmospheric humidity of approximately 100% and afterwards for 60 hours at approximately 15° C. in a translucent incubation cabinet at a relative atmospheric humidity of approximately 100%.

The plants are placed in the greenhouse at a temperature of approximately 15° C. and a relative atmospheric humidity of approximately 80%.

The test is evaluated 21 days after the inoculation. 0% means an efficacy which corresponds to that of the untreated control, while an efficacy of 100% means that no disease is observed.

In this test, the following compounds from table I according to the invention, show at an active compound concentration of 500 ppm, an efficacy of 70% or more:

TABLE I

| Example | Efficacy |
| --- | --- |
| 7 | 88 |
| 11 | 89 |
| 12 | 71 |
| 13 | 100 |
| 14 | 93 |
| 21 | 100 |
| 23 | 100 |
| 28 | 90 |
| 46 | 89 |
| 51 | 80 |
| 64 | 100 |
| 66 | 100 |
| 67 | 100 |
| 86 | 86 |
| 90 | 86 |
| 99 | 86 |
| 100 | 100 |
| 106 | 80 |
| 116 | 100 |
| 118 | 86 |
| 139 | 100 |
| 148 | 100 |
| 149 | 100 |
| 151 | 93 |
| 153 | 86 |
| 163 | 71 |
| 208 | 100 |

Example J

*Pyricularia* Test (Rice)/Protective

Solvent: 28.5 parts by weight of acetone
Emulsifier: 1.5 part by weight of alkylaryl polyglycol ether To produce a suitable preparation of active compound, 1 part by weight of active compound is mixed with the stated amount of solvent, and the concentrate is diluted with water and the stated amount of emulsifier to the desired concentration.

To test for protective activity, young rice plants are sprayed with the preparation of active compound at the stated application rate. 1 day after the treatment, the plants are inoculated with an aqueous spore suspension of *Pyricularia oryzae*. The plants are then placed in a greenhouse at a relative atmospheric humidity of 100% and a temperature of 25° C.

Evaluation is carried out 5 days after the inoculation. 0% means an efficacy which corresponds to that of the control, whereas an efficacy of 100% means that no infection is observed.

In this test, the following compounds from table J according to the invention, show at an active compound concentration of 250 ppm, an efficacy of 80% or more:

TABLE J

| Example | Efficacy |
| --- | --- |
| 7 | 97 |
| 12 | 93 |
| 13 | 97 |
| 14 | 98 |
| 21 | 85 |
| 22 | 80 |
| 24 | 98 |
| 31 | 98 |
| 46 | 96 |
| 47 | 90 |
| 66 | 100 |
| 67 | 96 |

TABLE J-continued

| Example | Efficacy |
| --- | --- |
| 116 | 97 |
| 148 | 80 |

Under the same conditions, high (at least 90%) protection to excellent (at least 95%) protection is observed at a dose of 100 ppm and 250 ppm of active ingredient with compound 116, whereas poor (less than 20%) protection to good (at least 70%) protection is observed with the compound of example 11 disclosed in patent application WO-2003/070705 as in table J2.

TABLE J2

| Example | dose (ppm) | Efficacy |
| --- | --- | --- |
| 116 from this invention | 250 | 97 |
|  | 100 | 90 |
| 11 from WO-2003/070705 | 250 | 80 |
|  | 100 | 20 |

Example 11 disclosed in international patent WO-2003/070705 corresponds to N-(3',4'-dichloro-5-fluorobiphenyl-2-yl)-3-(difluoromethyl)-1-methyl-1H-pyrazole-4-carboxamide [commun name: bixafen].

These results show that the compounds according to the invention have a better biological activity than the structurally closest compounds disclosed in WO-2003/070705.

Example K

*Rhizoctonia* Test (Rice)/Protective

Solvent: 28.5 parts by weight of acetone
Emulsifier: 1.5 part by weight of alkylaryl polyglycol ether To produce a suitable preparation of active compound, 1 part by weight of active compound is mixed with the stated amount of solvent, and the concentrate is diluted with water and the stated amount of emulsifier to the desired concentration.

To test for protective activity, young rice plants are sprayed with the preparation of active compound at the stated application rate. 1 day after the treatment, the plants are inoculated with hyphae of *Rhizoctonia solani*. The plants are then placed in a greenhouse at a relative atmospheric humidity of 100% and a temperature of 25° C.

Evaluation is carried out 4 days after the inoculation. 0% means an efficacy which corresponds to that of the control, whereas an efficacy of 100% means that no infection is observed.

In this test, the following compounds from table K according to the invention, show at an active compound concentration of 250 ppm, an efficacy of 95% or more:

TABLE K

| Example | Efficacy |
| --- | --- |
| 7 | 100 |
| 11 | 100 |
| 12 | 100 |
| 13 | 100 |
| 14 | 100 |
| 21 | 100 |
| 22 | 100 |
| 24 | 100 |
| 31 | 100 |

TABLE K-continued

| Example | Efficacy |
| --- | --- |
| 46 | 97 |
| 47 | 100 |
| 48 | 98 |
| 66 | 100 |
| 67 | 100 |
| 98 | 100 |
| 99 | 100 |
| 105 | 100 |
| 116 | 97 |
| 139 | 100 |
| 148 | 100 |

Example L

*Cochliobolus* Test (Rice)/Protective

Solvent: 28.5 parts by weight of acetone
Emulsifier: 1.5 parts by weight of polyoxyethylene alkyl phenyl ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated rate of application. One day after spraying, the plants are inoculated with an aqueous spore suspension of the causal agent of rice brown spot (*Cochliobolus miyabeanus*). The plants are then placed in an incubator at approximately 25° C. and a relative atmospheric humidity of approximately 100% for 1 day.

The test is evaluated 4 days after the inoculation. 0% means an efficacy which corresponds to that of the control, while an efficacy of 100% means that no disease is observed.

In this test, the following compounds from table L according to the invention, show at an active compound concentration of 250 ppm, an efficacy of 80% or more:

TABLE L

| Example | Efficacy |
| --- | --- |
| 7 | 80 |
| 13 | 85 |
| 14 | 90 |
| 21 | 85 |
| 31 | 80 |
| 66 | 93 |
| 67 | 90 |
| 98 | 93 |
| 99 | 95 |
| 105 | 95 |
| 116 | 90 |
| 139 | 95 |
| 148 | 95 |
| 166 | 80 |

Example M

*Phakopsora* Test (Soybeans)/Protective

Solvent: 28.5 parts by weight of acetone
Emulsifier: 1.5 parts by weight of polyoxyethylene alkyl phenyl ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated rate of application. One day after spraying, the plants are inoculated with an aqueous spore suspension of the causal agent of soybean rust (*Phakopsora pachyrhizi*). The plants are then placed in a greenhouse at approximately 20° C. and a relative atmospheric humidity of approximately 80%.

The test is evaluated 11 days after the inoculation. 0% means an efficacy which corresponds to that of the control, while an efficacy of 100% means that no disease is observed.

In this test, the following compounds from table M according to the invention, show at an active compound concentration of 250 ppm, an efficacy of 80% or more:

TABLE M

| Example | Efficacy |
| --- | --- |
| 13 | 98 |
| 14 | 98 |
| 21 | 98 |
| 46 | 85 |
| 47 | 98 |
| 48 | 99 |
| 51 | 93 |
| 64 | 97 |
| 66 | 98 |
| 83 | 94 |
| 84 | 80 |
| 116 | 85 |
| 117 | 98 |
| 148 | 98 |

The invention claimed is:

1. A 1-Methyl-3-dihalogenomethyl-5-halogenopyrazole-carboxamide of formula (I)

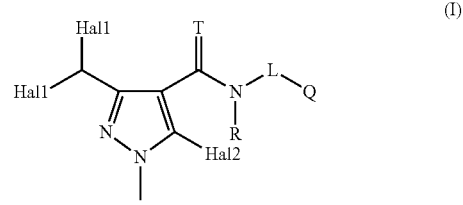

in which

T represents an oxygen or sulfur atom;

R represents hydrogen, $C_1$-$C_6$-alkylsulfonyl, $C_1$-$C_4$-alkoxy-$C_1$-$C_4$-alkyl, $C_1$-$C_4$-haloalkylsulfonyl, halo-$C_1$-$C_4$-alkoxy-$C_1$-$C_4$-alkyl or formyl;

Hal1 and Hal2 independently of one another represent chlorine or fluorine;

L represents phenyl which may be substituted by up to 4 identical or different groups $R^1$;

Q represents phenyl linked at position 3 or 4 to the phenyl ring L and which may be substituted by up to 5 identical or different groups $R^b$; or Q represents halogen; nitro; cyano; isonitrile; hydroxyl; amino; sulfanyl; pentafluoro-$\lambda$6-sulfanyl; formyl; formyloxy; formylamino; optionally substituted (hydroxyimino)-$C_1$-$C_8$-alkyl; optionally substituted ($C_1$-$C_8$-alkoxyimino)-$C_1$-$C_8$-alkyl; optionally substituted ($C_2$-$C_8$-alkenyloxyimino)-$C_1$-$C_8$-alkyl; optionally substituted ($C_2$-$C_8$-alkynyloxyimino)-$C_1$-$C_8$-alkyl; optionally substituted (benzyloxyimino)-$C_1$-$C_8$-alkyl; carboxyl; carbamoyl; N-hydroxycarbamoyl; carbamate; optionally substituted $C_1$-$C_{16}$-alkyl; optionally substituted $C_2$-$C_8$-alkenyl; optionally substituted $C_2$-$C_8$-alkynyl; optionally substituted $C_1$-$C_8$-alkylsulfanyl; optionally substituted $C_1$-$C_8$-alkylsulfinyl; optionally substituted $C_1$-$C_8$-alkylsulfonyl; optionally substituted $C_1$-$C_8$-alkylamino; optionally substituted di-$C_1$-$C_8$-alkylamino; optionally substituted $C_2$-$C_8$-alkenyloxy; optionally substituted $C_3$-$C_8$-alkynyloxy; optionally substituted $C_3$-$C_8$-cycloalkyl; optionally substituted ($C_3$-$C_8$-cycloalkyl)-$C_1$-$C_8$-alkyl; optionally substituted ($C_3$-$C_8$-cycloalkyl)-($C_3$-$C_8$-cycloalkyl; optionally substituted ($C_3$-$C_8$-cycloalkyl)-$C_2$-$C_8$-alkenyl; optionally substituted ($C_3$-$C_8$-cycloalkyl)-$C_2$-$C_8$-alkynyl; optionally substituted tri($C_1$-$C_8$)alkylsilyl; optionally substituted tri($C_1$-$C_8$)alkylsilyl-$C_1$-$C_8$-alkyl; optionally substituted $C_1$-$C_8$-alkylcarbonyl; optionally substituted $C_1$-$C_8$-alkylcarbonyloxy; optionally substituted $C_1$-$C_8$-alkylcarbonylamino; optionally substituted $C_1$-$C_8$-alkoxycarbonyl; optionally substituted $C_1$-$C_8$-alkyloxycarbonyloxy; optionally substituted $C_1$-$C_8$-alkylcarbamoyl; optionally substituted di-$C_1$-$C_8$-alkylcarbamoyl; optionally substituted $C_1$-$C_8$-alkylaminocarbonyloxy; optionally substituted di-$C_1$-$C_8$-alkylaminocarbonyloxy; optionally substituted N—($C_1$-$C_8$-alkyl)hydroxycarbamoyl; optionally substituted $C_1$-$C_8$-alkoxycarbamoyl; optionally substituted N—($C_1$-$C_8$-alkyl)-$C_1$-$C_8$-alkoxycarbamoyl; $C_1$-$C_8$-arylalkyl which is optionally substituted by up to 6 identical or different groups $R^b$; $C_2$-$C_8$-arylalkenyl which is optionally substituted by up to 6 identical or different groups $R^b$; $C_2$-$C_8$-arylalkynyl which is optionally substituted by up to 6 identical or different groups $R^b$; aryloxy which is optionally substituted by up to 6 identical or different groups $R^b$; arylsulfanyl which is optionally substituted by up to 6 identical or different groups $R^b$; arylamino which is optionally substituted by up to 6 identical or different groups $R^b$; $C_1$-$C_8$-arylalkyloxy which is optionally substituted by up to 6 identical or different groups $R^b$; $C_1$-$C_8$-arylalkylsulfanyl which is optionally substituted by up to 6 identical or different groups $R^b$; $C_1$-$C_8$-arylalkylamino which is optionally substituted by up to 6 identical or different groups $R^b$ or a bicyclo[2.2.1]heptanyl group;

$R^1$, $R^b$ independently of one another represent halogen; nitro, cyano, $C_1$-$C_{12}$-alkyl; $C_1$-$C_6$-haloalkyl having 1 to 9 identical or different halogen atoms; $C_1$-$C_6$-alkoxy; $C_1$-$C_6$-haloalkoxy having 1 to 9 identical or different halogen atoms; $C_1$-$C_6$-alkylsulfanyl; $C_1$-$C_6$-haloalkylsulfanyl having 1 to 9 identical or different halogen atoms; $C_1$-$C_6$-alkylsulfonyl; $C_1$-$C_6$-haloalkylsulfonyl having 1 to 9 identical or different halogen atoms; $C_2$-$C_{12}$-alkenyl; $C_2$-$C_{12}$-alkynyl; $C_3$-$C_7$-cycloalkyl; phenyl; tri($C_1$-$C_8$)alkylsilyl; tri($C_1$-$C_8$)alkylsilyl-$C_1$-$C_8$-alkyl;

where, unless indicated otherwise, a group or a substituent which is substituted by at least one $R^b$; or Q and $R^1$ together with the carbon atoms to which said Q and $R^1$ are attached form an optionally substituted 5-, 6- or 7-membered carbocyclic or saturated heterocyclic ring; or Q and L together form a radical of the formula ($W^1$),

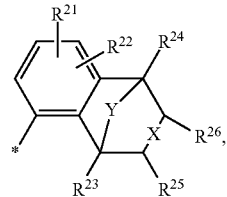

where
the bond marked by * is attached to an amide;
X represents a single bond or a double bond;
Y represents oxygen, sulfur, N($R^{27}$) or ($CR^{28}R^{29}$)($CR^{30}R^{31}$)$_m$($CR^{32}R^{33}$)$_n$;
m represents 0 or 1;
n represents 0 or 1;
$R^{21}$ and $R^{22}$ independently of one another represent hydrogen, halogen, $C_1$-$C_4$-alkyl, $C_1$-$C_4$-alkoxy or $C_1$-$C_4$-haloalkoxy;
$R^{23}$, $R^{24}$, $R^{25}$ and $R^{26}$ independently of one another represent hydrogen, halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfanyl, $C_1$-$C_4$-haloalkylsulfanyl, hydroxymethyl, $C_1$-$C_4$-alkoxymethyl, C(O)$CH_3$ or C(O)O$CH_3$;
$R^{27}$ represents hydrogen, $C_1$-$C_4$-alkyl, benzyl where the phenyl group is optionally substituted up to three times by a radical independently selected from the group consisting of halogen, $C_1$-$C_4$-alkyl, $C_1$-$C_4$-haloalkyl and $C_1$-$C_4$-alkoxy, formyl, C(O)$C_1$-$C_4$-alkyl optionally substituted by halogen or $C_1$-$C_4$-alkoxy, C(=O)O—$C_1$-$C_6$-alkyl optionally substituted by halogen, $C_1$-$C_4$-alkoxy or cyano or $C_1$-$C_4$-alkoxy-($C_1$-$C_4$)-alkylene;
$R^{28}$, $R^{29}$, $R^{30}$, $R^{31}$, $R^{32}$ and $R^{33}$ independently of one another represent hydrogen, halogen, hydroxyl, $C_1$-$C_4$-alkoxy, $C_1$-$C_6$-alkyl optionally substituted by halogen, hydroxyl, $C_1$-$C_4$-alkoxy, =O, aryl, O—C(O)—$C_1$-$C_4$-alkyl or a 3-7-membered carbocyclic ring which is itself optionally substituted by up to three methyl groups or $C_2$-$C_6$-alkenyl optionally substituted by halogen, hydroxyl, $C_1$-$C_4$-alkoxy, =O, aryl, O—C(O)—$C_1$-$C_4$-alkyl or a 3-7-membered carbocyclic ring which is itself optionally substituted by up to three methyl groups or a 3-7-membered saturated ring which is optionally substituted by up to three methyl groups and optionally contains a heteroatom selected from the group consisting of nitrogen and oxygen; or
$R^{28}$ and $R^{29}$ together with the carbon atom to which said $R^{28}$ and $R^{29}$ are attached form a group C=O or a three- to five-membered carbocyclic ring which is optionally substituted by up to three methyl groups and optionally contains up to two heteroatoms independently selected from the group consisting of nitrogen and oxygen; or
$R^{28}$ and $R^{29}$ together form a $C_1$-$C_6$-alkylidene which is optionally substituted by up to four groups that can be the same or different and that can be selected from the group consisting of fluorine, chlorine, bromine and methyl, or a $C_3$-$C_6$-cycloalkylidene group which is optionally substituted by up to three methyl groups.

2. A compound according to claim 1, wherein T represents an oxygen atom.

3. A compound according to claim 1, wherein R represents hydrogen, methylsulfonyl, ethylsulfonyl, n- or isopropylsulfonyl, n-, iso-, sec- or tert-butylsulfonyl, methoxymethyl, methoxyethyl, ethoxymethyl, ethoxyethyl, trifluoromethylsulfonyl, trifluoromethoxymethyl or formyl.

4. A compound according to claim 1, wherein R represents hydrogen, methoxymethyl, or formyl.

5. A compound according to claim 1, wherein L represents

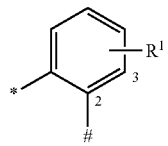

L-1

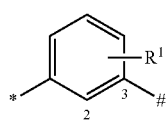

L-2 where the bond marked by * is attached to the amide while the bond marked # is attached to Q; and optionally $R^1$ and Q together with the carbon atoms to which said $R^1$ and Q are attached can form an optionally substituted 5- or 6-membered carbocyclic or heterocyclic ring.

6. A compound according to claim 1, wherein $R^1$ represents hydrogen, fluorine, chlorine, methyl or trifluoromethyl.

7. A compound according to claim 1, wherein Q and $R^1$ together with the carbon atoms to which said Q and $R^1$ are attached represent a 5- or 6-membered carbocyclic ring which is optionally mono-, di- or trisubstituted by methyl or a 5- or 6-membered saturated heterocyclic ring containing one oxygen atom and which is optionally mono-, di- or trisubstituted by methyl.

8. A compound according to claim 1, wherein Q represents $Q^1$

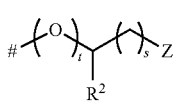

$Q^1$ where the bond marked # is attached to L;
$R^2$ represents hydrogen, halogen, $C_1$-$C_4$-alkyl or $C_1$-$C_4$-haloalkyl;
Z represents —$CR^3R^4R^5$ or —$SiR^3R^4R^5$;
s represents 0, 1, 2 or 3;
t represents 0 or 1;
$R^3$, $R^4$, $R^5$ independently of one another represent hydrogen, $C_1$-$C_8$-alkyl or $C_1$-$C_6$-haloalkyl;
or $R^3$ and $R^4$ together with the carbon atom to which said $R^3$ and $R^4$ are attached form a 3- to 6-membered carbocyclic saturated or unsaturated ring,
provided that $R^2$ is not hydrogen, methyl or ethyl when Z is —$CR^3R^4R^5$ and s represents 1 and t represents 0.

9. A compound according to claim 1, wherein Q represents $Q^2$

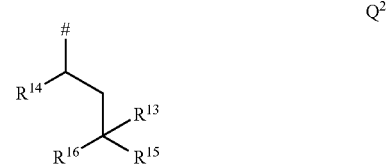

where the bond marked # is attached to L;
$R^{13}$ represents hydrogen, halogen, $C_1$-$C_8$-alkyl or $C_1$-$C_8$-haloalkyl;
$R^{14}$, $R^{15}$ and $R^{16}$ independently of one another represent hydrogen, methyl or ethyl.

10. A compound according to claim 1, wherein Q represents $Q^3$

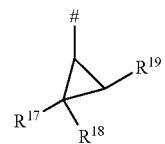

$Q^3$ where the bond marked # is attached to L;
$R^{17}$ represents hydrogen or halogen;
$R^{18}$ represents hydrogen or halogen;
$R^{19}$ represents optionally substituted $C_2$-$C_{12}$-alkyl, optionally substituted $C_2$-$C_{12}$-alkenyl, optionally substituted $C_2$-$C_{12}$-alkynyl, optionally substituted $C_3$-$C_{12}$-cycloalkyl, optionally substituted phenyl or heterocyclyl.

11. A compound according to claim 1, wherein Q represents $Q^4$

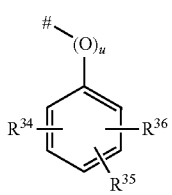

$Q^4$ where the bond marked # is attached to L,
$R^{34}$, $R^{35}$ and $R^{36}$ independently of one another represent halogen, cyano, nitro, $C_1$-$C_6$-alkyl, $C_2$-$C_6$-alkenyl, $C_1$-$C_4$-alkoxy, $C_1$-$C_4$-alkylsulfanyl, $C_1$-$C_4$-alkylsulfonyl, $C_3$-$C_6$-cycloalkyl, or represent $C_1$-$C_4$-haloalkyl, $C_1$-$C_4$-haloalkoxy, $C_1$-$C_4$-haloalkylsulfanyl or $C_1$-$C_4$-haloalkylsulfonyl having in each case 1 to 5 halogen atoms;
u represents 0 or 1.

12. A compound according to claim 1, wherein
Q represents $Q^5$

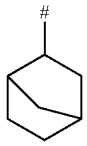

$Q^5$ where the bond marked # is attached to L.

13. A compound according to claim 1, wherein
Q represents $Q^6$

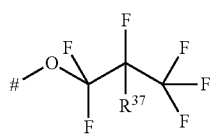

$Q^6$ where $R^{37}$ represents hydrogen or fluorine and where the bond marked # is attached to L.

14. A compound according to claim 1, wherein Q and L together form a radical of the formula (W1) and wherein
X represents a single bond.

15. A compound according to claim 1, wherein Q and L together form a radical of the formula (W1) and wherein
Y represents oxygen, sulfur, $N(R^{27})$, $CH_2$, $CH_2CH_2$, $CH_2CH_2CH_2$, $C(CH_3)_2$, $CH(CH_3)$, $CH(C_2H_5)$, $C(CH_3)(C_2H_5)$, $CH(OCH_3)$ or $C(OCH_3)_2$.

16. A compound according to claim 14, wherein
n represents 0.

17. A compound according to claim 14, wherein
m represents 0.

18. A compound according to claim 5, wherein
T represents oxygen;
R represents hydrogen;
Hal1 represents fluorine;
L represents L-1 or L-2;
Q represents $Q^1$, $Q^2$, $Q^3$, $Q^4$, $Q^5$, or $Q^6$;
$R^1$ represents hydrogen or fluorine;
$Q^1$ represents

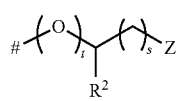

where the bond marked # is attached to L,
$R^2$ represents hydrogen, methyl or ethyl,
Z represents $—CR^3R^4R^5$ or $—SiR^3R^4R^5$;
s represents 0, 1, 2 or 3;
t represents 0,
$R^3$, $R^4$, $R^5$ independently of one another represent hydrogen or methyl;

$Q^2$ represents

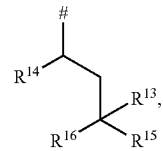

where the bond marked # is attached to L;
$R^{13, 15, 16}$ independently of one another represent hydrogen or methyl;
$R^{14}$ represents hydrogen, methyl or ethyl,
$Q^3$ represents

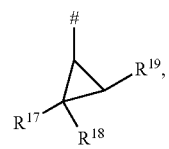

where the bond marked # is attached to L;
$R^{17, 18}$ represents hydrogen;
$R^{19}$ represents cyclopropyl;
$Q^4$ represents

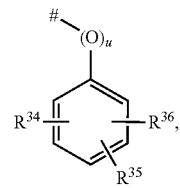

u represents 0,
$R^{34}$, $R^{35}$ and $R^{36}$ independently of one another represent F, Cl, Br or trifluoromethyl,
where the bond marked # is attached to L;
$Q^5$ represents

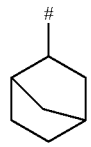

$Q^6$ represents

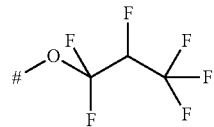

or Q and L together form a radical of the formula ($w^{1-A}$), where the bond marked * is attached to the amide,

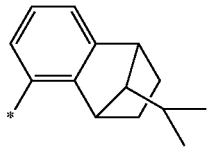
($W^{1-A}$)

or Q and L together form a radical of the formula ($W^{1-B}$), where the bond marked * is attached to the amide,

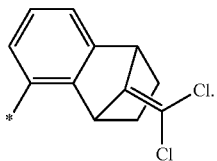
($W^{1-B}$)

19. A fungicide composition comprising, as an active ingredient, an effective amount of a compound of formula (I) according to claim 1, and an agriculturally acceptable support, carrier and/or filler.

20. A method for controlling phytopathogenic fungi of crops, comprising applying an agronomically effective and substantially non-phytotoxic quantity of a compound according to claim 1, to soil where a plant grows and/or is capable of growing, to leaves and/or fruit of a plant and/or to seeds of a plant.

21. A compound of formula

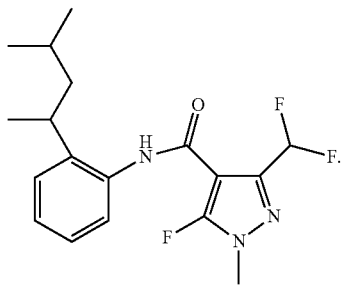 [SMILES: CC(C)CC(C)c1ccccc1NC(=O)c1c(C(F)F)nn(C)c1F]

* * * * *